(12) United States Patent
Bachiller Pérez et al.

(10) Patent No.: US 12,338,453 B2
(45) Date of Patent: Jun. 24, 2025

(54) METHOD FOR THE INTRODUCTION OF GENETIC INFORMATION IN CELL BY SITE-SPECIFIC INTEGRATION SYSTEM

(71) Applicant: CONSEJO SUPERIOR DE INVESTIGACIONES CIENTÍFICAS (CSIC), Madrid (ES)

(72) Inventors: Daniel Bachiller Pérez, Esporles (ES); Esther Palomino Lago, Esporles (ES)

(73) Assignee: CONSEJO SUPERIOR DE INVESTIGACIONES CIENTÍFICAS (CSIC), Madrid (ES)

( * ) Notice: Subject to any disclaimer, the term of this patent is extended or adjusted under 35 U.S.C. 154(b) by 1022 days.

(21) Appl. No.: 17/414,292

(22) PCT Filed: Dec. 17, 2019

(86) PCT No.: PCT/EP2019/085737
§ 371 (c)(1),
(2) Date: Jun. 15, 2021

(87) PCT Pub. No.: WO2020/127332
PCT Pub. Date: Jun. 25, 2020

(65) Prior Publication Data
US 2022/0025406 A1    Jan. 27, 2022

(30) Foreign Application Priority Data
Dec. 17, 2018   (ES) ................................. 201831227

(51) Int. Cl.
C12N 15/90   (2006.01)
(52) U.S. Cl.
CPC ................................. C12N 15/902 (2013.01)
(58) Field of Classification Search
None
See application file for complete search history.

(56) References Cited

U.S. PATENT DOCUMENTS

2018/0249688 A1*  9/2018  Ayares ................ A01K 67/0275

FOREIGN PATENT DOCUMENTS

| WO | 2015073703 | 5/2015 |
| WO | 2015160683 | 10/2015 |

OTHER PUBLICATIONS

International Search Report and Written Opinion for International Application No. PCT/EP2019/085737 mailed Feb. 21, 2020, 18 pages.
Palomino Lago, Esther, "Establishing a Safe Harbor Site for the Introduction of Genetic Information in the Human Cells By the Recombination System attP/attB," Doctoral Thesis Universitat de les Illes Balears, Jan. 1, 2018, 160 pages.
Duportet, Xavier, "Developing new tools and platforms for mammalian synthetic biology: From the assembly and chromosomal integration of complex DNA circuits to the engineering of artificial intercellular communication systems," Internet Citation <https://hal.archives-ouvertes.fr/tel-01108520>, Nov. 14, 2014, 171 pages.
Murray, James D., et al., Program and Abstracts of the 12th Transgenic Technology Meeting (TT2014) ED, Transgenic Research, Spring Netherlands, NL, vol. 23, No. 5, Aug. 26, 2014, 83 pages.
Burnight, Erin Rae, "Targeting therapeutic vector expression and integration for gene therapy applications," University of Iowa, Iowa Research Online, May 1, 2011, 135 pages.
Guye, Patrick, et al., "Rapid, modular and reliable construction of complex mammalian gene circuits," Nucleic Acids Research, 2013, vol. 41, No. 16, Jul. 11, 2013, 13 pages.
Watanabe, Kiichi, et al., "A Rock inhibitor permits survival of dissociated human embryonic stem cells," Nature Biotechnology, vol. 25, No. 6, Jun. 2007, 6 pages.
Aasen, Trond, et al., "Efficient and rapid generation of induced pluripotent stem cells from human keratinocytes," Nature Biotechnology, vol. 26, No. 11, Nov. 2008, 9 pages.
Cai, Liuhong, et al., "Promoting human embryonic stem cell renewal or differentiation by modulating Wnt signal and culture conditions," Cell Research 2007, Jan. 9, 2007, 11 pages.
Dravid, Gautam, et al., "Defining the Role of Wnt/ß-Catenin Signaling in the Survival, Proliferation, and Self-Renewal of Human Embryonic Stem Cells," Stem Cells 2005, Jul. 7, 2005, 13 pages.
Dravid, Gautam, et al., "Culture of Human Embryonic Stem Cells on Human and Mouse Feeder Cells," Methods in Molecular Biology, vol. 331: Human Embryonic Stem Cell Protocols, 2006, 14 pages.
Fleischer, Aarne, et al., "Generation of two induced pluripotent stem cell (iPSC) lines from p. F508del Cystic Fibrosis patients," Stem Cell Research, Mar. 11, 2018, 5 pages.
Lorenzo, I.M., et al., "Generation of Mouse and Human Induced Pluripotent Stem Cells (iPSC) from Primary Somatic Cells," Stem Cell Rev and Rep, Oct. 27, 2021, 16 pages.
Normand, J., et al., "A Method for the Isolation and Serial Propagation of Keratinocytes, Endothelial Cells, and Fibroblasts from a Single Punch Biopsy of Human Skin," In Vitro Cellular & Development Biology. Animal, vol. 31, No. 6, Jun. 1995, 10 Pages.

(Continued)

*Primary Examiner* — Jennifer Dunston
*Assistant Examiner* — Tiffany Nicole Grooms
(74) *Attorney, Agent, or Firm* — Hayes Soloway P.C.

(57) ABSTRACT

The present invention relates to a method for integrating one or more recombinant sites in a sole target gene of a cell genome comprising carrying out sequentially multiple site-specific recombination by using alternatively two different serine-integrases, wherein the selection marker is removed after each site-specific recombination by different transposases: An in vitro method for inserting at least one recombinant site in a target gene/locus from an isolated cell genome, said method comprising integrating a nucleotide sequence A into the target gene from an isolated cell genome by homologous recombination, wherein said nucleotide sequence A comprises a recombination cassette, flanked at 5' and 3' by target gene homology arms, and removing the selection marker by using the second transposase, thus obtaining a cell genome A comprising (i), (ii) and (iii) of nucleotide sequence A.

15 Claims, 23 Drawing Sheets

Specification includes a Sequence Listing.

(56) References Cited

OTHER PUBLICATIONS

Park, In-Hyun, et al., "Reprogramming of human somatic cells to pluripotency with defined factors," Nature, vol. 451, Jan. 10, 2008, 7 pages.
Scherer, William F., et al., "Studies on the Propagation In Vitro of Poliomyelitis Viruses," J Exp Med., May 1953, 21 pages.
Sengupta, Ranjita, et al., "Viral Cre-LoxP tools aid genome engineering in mammalian cells," Journal of Biological Engineering, 2017, 9 pages.

\* cited by examiner

A

B

C

A pmCherry C1     pEP46

B

A

B

C

D

A

B

METHOD FOR THE INTRODUCTION OF GENETIC INFORMATION IN CELL BY SITE-SPECIFIC INTEGRATION SYSTEM

CROSS-REFERENCE TO RELATED APPLICATIONS

The present patent application is a U.S. national phase application of International Application No. PCT/EP2019/085737, filed Dec. 17, 2019, which claims priority to Spanish Patent Application No. P201831227, filed Dec. 17, 2018, the disclosures of which are incorporated herein by reference.

INCORPORATION BY REFERENCE

The content of the ASCII text file of the sequence listing named "Sequence_Listing", which is 12 kb in size, was created on and electronically submitted via EFS-Web Jun. 15, 2021, is incorporated herein by reference in its entirety.

The present invention relates to a stable docking platform for secure and easy loading of genetic information into the genome of living cells. To build this safe harbor system, a complex strategy combining different molecular tools has been designed. Thus, the present invention relates to biotechnological field, particularly, genetic engineering field.

STATE OF THE ART

Genome editing is a type of genetic engineering in which DNA is modified in the genome of single cells or organisms. Recent advances in genome editing technologies have improved the ability to make specific and easy changes in the genomes of cells and, therefore, to create new applications into all areas of biotechnology, including biopharmaceutical production, construction of complex gene circuits for synthetic biology, environment, studies of genome structure, regulation, and function, as well as clinical applications.

An ideal gene editing tool should present easy production, efficiency, targeting at multiple sites, high frequency of desired sequence changes in the target cell population and low toxicity. In addition, genome modifications should be heritable, and amenable to simple reading and testing the edition. In eukaryotic cells, the most frequently used genome editing technologies are based on programmable nucleases. These enzymes enable precise genome editing by introducing DNA Double-Strand Breaks (DSBs) at specific genomic locations. The most important programmable nucleases are Zinc Finger Nuclease (ZFN), Transcription Activator-Like Effector Nucleases (TALENs) and Clustered Regularly Interspaced Short Palindromic Repeats (CRISPR/Cas9). Creating double-strand breaks may have undesired side effects, so an important limitation for the use of programmable nucleases is their potential off-target activity.

Other molecular tools that are able to perform specific modifications in the genome are Site-Specific Recombinases (SSRs) and Transposons. SSRs have been used by the research community to induce reproducible site-specific genomic integration with high efficiency. Some site-specific recombination methods relay on recombination of two non-identical DNA sequences called, attachment sites (att), catalyzed by a phage-encoded integrase protein (Int), that generates new, hybrid attachment sites as products of the reaction. In order to use this system in genome editing, an attachment site must already exist in the genome and a complementary attachment site in the DNA to be integrated into that locus.

Transposable elements are DNA sequences that move from one location on the genome to another. Transposon DNA has Inverted Terminal Repeats (ITRs) that are recognized by specific transposases and moved by cut and paste mechanism in which the transposon is excised from one location and reintegrated elsewhere. Neither SSRs or transposases require DNA synthesis or degradation, nor any cofactors such as ATP.

Apart from the above-mentioned molecular tools, other critical parameters such as cell type, genome loci and delivery methods that profoundly affect the outcome of gene editing processes, have to be considered when dealing with genome editing.

Among the different cell lines currently used in genome engineering, induced Pluripotent Stem (iPS) cells hold the biggest promise for their use in disease modeling, therapeutic screens or clinical applications. The iPS cells derived from somatic cells and transformed to an embryonic-like state by the addition of reprogramming factors show similar molecular and functional features as Embryonic Stem Cells (ESCs).

Stable and safe chromosomal integration of genetic payloads can help achieve long-term expression of transgenes. Genome Safe Harbors (GSHs) are secure locations in the genome where the newly integrated genetic material keeps their intended activity without adversely altering cellular functions. Their location in selected genes assumes that certain non-essential genes can be disrupted without pathological consequences. The most commonly GSHs used for targeted transgene addition in the human genome are the adeno-associated virus site 1 (AAVS1), the chemokine (CC motif) receptor 5 gene (CCR5), the human orthologue of the mouse ROSA26 locus and the H11 locus.

The latest docking platform to be described in the literature is based on the integration of single attachment sites into several locations of the genome (Sengupta, R., et al. 2017, Journal of Biological Engineering, 11 (1): 45). The authors identified new, putative safe harbor sites in the human genome, among them, a Rosa26 homolog that could potentially support long-term expression of transgenes. They integrated single Bxb1-specific attP sites simultaneously at three selected loci in CHO cells by CRISPR/Cas9-assisted HR. The system generated a functional platform for site-specific integration into three distinct chromosomal locations. However, the assembly of the platform required the use of CRISPR/Cas9-assisted HR for the establishment of each one of the docking sites, therefore, multiplying by three the possibility of off-targets events.

In many instances, it is desirable to insert a nucleic acid sequence into the human genome such that the inserted nucleic acid may be expressed while causing no disruption of the regulatory elements or genes in the genome at or near the insertion site. However, the currently available technologies for inserting a transgene into the human genome have serious drawbacks. For example, gene insertion mediated by retroviruses, lentiviruses, transposons, and non-homologous end-joining result in random integration. The consequent lack of control over transgene insertion site, copy number, and orientation compromises the precision of experiments. Moreover, these methods often have limits on the size of the DNA that can be inserted.

The international application WO2015/073703A1 discloses a method for inserting a polynucleotide sequence into the genome of a human cell. The method results in insertion of a polynucleotide sequence of interest into the H11 locus in the genome of a human cell. However, this method does not allow the integration into the genome of multiple polynucleotide sequences in the same locus.

The methods, nucleic acids, and transgenic cells disclosed herein address the above limitations and fulfill other needs.

DESCRIPTION OF THE INVENTION

The present invention provides a stable docking platform for secure and easy loading of genetic information into the genome of living cells. To build this safe harbor system, a complex strategy combining different molecular tools has been designed. The strategy provides a serial mechanism by which multiple docking modules, each comprised of one or more docking sites (also called recombinant site), can be assembled into the a locus of a cell genome. Once the core of the recombinant site has been stablished, the method disclosed in the present invention does not require the use of nucleases for adding genetic material into cells, and allows the serial addition of new docking sites, at the same time that the integration is stable in the human cell line, reducing significantly the risk of off-targets events.

Thus, the method disclosed in this description allows for simultaneous integration of various transgenes which can be identical or different each other. These integrations are performed at the same chromosomal location, which could be useful to study metabolic routes or gene interactions that require close transgene positions. In addition, multiple docking units can be incorporated into the genome after the initial single homologous recombination event, thus, reducing the possibility of off-target effects when compared to several independent integrations at different locations. The method disclosed herein generates a recombinant site in the genome of human cells.

In order to achieve this, the method uses two recombination systems, homologous recombination (for example, TALEN-assisted homologous recombination), and site-specific recombination mediated by two different integrases (for example, the phiC31 and Bxb1 integrases). One integrase (for example phiC31) is used during the insertion of at least one recombinant site in a target gene/locus, and the other one (for example, Bxb1) is used in a posterior phase for uploading the gene of interest into the recombinant site. Additionally, two transposon systems (for example, Sleeping-Beauty and piggyBac) are used to eliminate selection markers, vector fragments and any other left-over DNA residue that could interfere with the efficiency of the cargo loading steps or the posterior expression of the newly incorporated gene/s of interest. As a proof of concept, the recombinant site was assembled in Hela cells and later demonstrated to work also in human iPS cells.

Recombinase phiC31 is an integrase used by phages to establish the lysogenic life cycle. During integration, phiC31 drives recombination between the attP and the attB attachment sites on the phage and host genome, respectively. In naturally occurring phage infestations, the end result is an integrated phage genome flanked by new attL and attR sites, generated by recombination between the original, attP and attB sites. As it is shown in the examples of the present description, the phage genome is substituted by the acceptor sites that will constitute the core of the safe harbor locus of the method disclosed herein. Under inducing conditions widely known in the state of the art, the phage genome is excised via integrase-mediated recombination between attL and attR regenerating the attP and attB attachment sites. The excision is directed by phiC31 in the presence of an accessory protein (the Recombination Directionality Factor, RDF). The alternative use of phiC31, alone or together with RDF, allows for the indefinite repetition of the cycle and the subsequent incorporation into the targeted locus of as many attachment sites as needed. The whole mechanism is made possible by the coordinated and alternative use of piggyBac and Sleeping Beauty transposons that, at each step, remove residual DNA fragments (plasmid sequences, selection elements, etc.). Once the final configuration of the recombinant site is reached, the Bxb1 recombinase is used to upload the desired genetic information: markers, therapeutic genes, inducible system or even complete regulatory routes.

The present invention relates to a method for the incorporation one or more safe integration sites (recombinant site/s) into a targeted locus of a living cell genome. The method uses an initial step of site directed homologous recombination followed by insertion/excision cycles catalyzed by a serine-integrase. In each cycle selection markers and undesired DNA remnants are eliminated by the alternative use of different transposases. The incorporation of genes of interest to the safe site is catalyzed by another serine-integrase. The method guaranties simultaneous and/or sequential uploading of multiple genetic elements into the safe harbor locus (target gene). In addition, it allows for the incorporation of new docking sites into the same locus even after all the pre-existing ones have been occupied. This method is disclosed in detailed below.

Method of the Invention

Thus, in view of the foregoing development, in one aspect the present invention relates to an in vitro method for inserting at least one recombinant site in a target gene/locus from an isolated cell genome, hereinafter "method of the invention", said method comprising:
  (a) integrating a nucleotide sequence A into the target gene from an isolated cell genome by homologous recombination, wherein said nucleotide sequence A comprises a recombination cassette, flanked at 5' and 3' by target gene homology arms, comprising
    (i) a serine-integrase attB or attP attachment site,
    (ii) a right-ITR element specific for a first transposase,
    (iii) a genetic construction comprising, at least one, first recombinant site and
    (iv) a selection marker flanked by ITR elements specific for a second transposase different from the first transposase, and
  (b) removing the selection marker by using the second transposase, thus obtaining a cell genome A comprising (i), (ii) and (iii) of nucleotide sequence A.

Hereinafter, for the shake of clarity, the method of the invention, as well as other inventive aspects derived therefrom (such as the second method of the invention, nucleotide sequences of the invention, and genetically engineering cells of the invention), is disclosed regarding the presence of a serine-integrase attB attachment site in element (i) of nucleotide sequence A. However, as the skilled person in the art understands, the method of the invention also works if the attB site of element (i) is replaced with attP attachment site as long as the complementarity between the attB/attP, attP/attB, attL/attR and attR/attL is maintained throughout all the steps of the method of the invention disclosed below. For example, a attP site in nucleotide sequence A can be used instead of the attB site if the inverse substitution, attP by attB, is also done in the nucleotide sequence B (see below) whose integration is catalyzed by phiC31.

The method of the invention relates to a method for inserting at least one recombinant site in a target gene/locus from an isolated cell genome.

As used herein, the term "recombinant site" refers to nucleotide sequence comprising not only an attB or attP site which serves a substrate for a recombinase, in particular, a serine-integrase, to provide for unidirectional site-specific recombination and to integrate a gene of interest into the DNA of a cell, but also the necessary elements to promote the expression of said gene of interest. In the present invention, the terms "recombinant site", "integration site" and "docking site" are equivalents and can be used interchangeably throughout the present description.

As used herein, the term "safe harbor locus" refers to a region of DNA within the genome where the newly integrated genetic material keeps their intended activity without adversely altering cellular functions. In the present invention, "a safe harbor locus" is the "target gene" or "target locus" in which a recombinant site in going to be integrated. Currently, there are several target loci (target genes) that can be safely used for transgene insertion in human cells including, but not limited to, adeno-associated virus site 1 (AAVS1), H11, human orthologue of the mouse ROS26 or the chemokine (C-C motif) receptor 5 (CCR5) gene, all of which are in exons or introns of endogenous cells and are differentially expressed in different tissue. In a particular embodiment of the method of the invention, the target gene is the CCR5 gene.

The AAVS1 locus on chromosome 19 (position 19q13.42) is a well characterized site for transgene expression in human pluripotent stem cells. Gene targeting at AAVS1 supports stable transgene expression without significant silencing during in vitro and in vivo differentiation.

The H11 locus is a safe, intergenic, transcriptionally active region on chromosome 22 which can support expression of multiple transgenes in hiPS cells and is a reliable option for genomic editing.

The human ROSA26 locus is on chromosome 3 (position 3p25.3). The human ROSA26 locus is also located near genes that can potentially be dysregulated by transgene targeting into this location. This safe harbor locus has thus far not been routinely used to express transgenes.

CCR5 is a co-receptor involved in HIV-1 infection of macrophages and T cells. Preliminary studies have shown that the homozygous deletion of the CCR5 gene, located on chromosome 3 (3p21.31 position), does not have any effect in humans. For this reason, modifying the CCR5 gene by genetic engineering methods will not have any damaging effect for the cell.

Any cell can be used in the method of the invention. Examples of cells include, without limited to, insect cells, vegetal cells, and mammal cells. These cells can be somatic cells, adult tissue specific stem cells, pluripotente stem cells embryonic stem cells, and induced pluripotent stem cells and their derivatives. In a particular embodiment, the mammal cell is a human cell, a CHO cell (Chinese hamster ovary cell) or a 3T3 cell (primary mouse embryonic fibroblast cell). Examples of human cells include, without limiting to, cell lines, such as Hela cells, somatic cells, adult tissue specific stem cells, pluripotent stem cells embryonic stem cells, and induced pluripotent stem cells and their derivatives. In a particular embodiment, the cell used in the method of the invention is an induced pluripotent stem cell.

By "pluripotent stem cell" or "pluripotent cell" it is meant a cell that has the ability under appropriate conditions of producing progeny of several different cell types that are derivatives of all of the three germinal layers (endoderm, mesoderm, and ectoderm). Pluripotent stem cells are capable of forming teratomas. Examples of pluripotent stem cells are embryonic stem (ES) cells, embryonic germ stem (EG) cells, induced pluripotent stem (iPS) cells and somatic stem cells. PS cells may be from any organism of interest, including, e.g., human.

By "embryonic stem cell" or "ES cell" it is meant a cell that a) can self-renew, b) can differentiate to produce all types of cells in an organism, and c) is derived from a developing organism or is an established ES cell line which was derived from a developing organism. ES cell may be derived from the inner cell mass of the blastula of a developing organism. ES cell may be derived from a blastomere generated by single blastomere biopsy (SBB) involving removal of a single blastomere from the eight cell stage of a developing organism. In general, SBB provides a non-destructive alternative to inner cell mass isolation. ES cells can be cultured over a long period of time while maintaining the ability to differentiate into all types of cells in an organism. In culture, ES cells typically grow as flat colonies with large nucleo-cytoplasmic ratios, defined borders and prominent nuclei. In addition, ES cells express SSEA-3, SSEA-4, TRA-1-60, TRA-1-81, and Alkaline Phosphatase, but not SSEA-1.

By "embryonic germ stem cell", embryonic germ cell" or "EG cell" it is meant a cell that a) can self-renew, b) can differentiate to produce all types of cells in an organism, and c) is derived from germ cells and germ cell progenitors, e.g. primordial germ cells, i.e. those that would become sperm and eggs. Embryonic germ cells (EG cells) are thought to have properties similar to embryonic stem cells as described above.

By "induced pluripotent stem cell" or "iPS cell" it is meant a cell that a) can self-renew, b) can differentiate to produce all types of cells in an organism, and c) is derived from a somatic cell. iPS cells have an ES cell-like morphology, growing as flat colonies with large nucleo-cytoplasmic ratios, defined borders and prominent nuclei. iPS cells are produced from somatic cells which are abundant and are not associated to ethical restrictions. In addition, iPSCs permit autologous transplantation in regenerative therapies thus eliminating the need for immunosuppressive treatment. In addition, iPS cells express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26al, TERT, and zfp42. iPS cells may be generated by providing the cell with "reprogramming factors", i.e., one or more, e.g., a cocktail, of biologically active factors that act on a cell to alter transcription, thereby reprogramming a cell to pluripotency.

By "somatic cell" it is meant any cell in an organism that, in the absence of experimental manipulation, does not ordinarily give rise to all types of cells in an organism. In other words, somatic cells are cells that have differentiated sufficiently that they will not naturally generate cells of all three germ layers of the body, i.e., ectoderm, mesoderm and endoderm. For example, somatic cells would include both neurons and neural progenitors, the latter of which may be able to self-renew and naturally give rise to all or some cell types of the central nervous system but cannot give rise to cells of the mesoderm or endoderm lineages.

As used herein, the term "integration" means that a nucleotide sequence is stably inserted into the cellular genome, i.e., covalently linked to the nucleic acid sequence within the cell's chromosomal DNA. By "targeted integration" it is meant that the nucleotide sequence is inserted into the cell's chromosomal or mitochondrial DNA at a specific site.

In order to insert at least one recombinant site in a target gene/locus from an isolated cell genome, the method of the invention comprises in a first step integrating a nucleotide sequence A into the target gene from an isolated cell genome by homologous recombination. By "recombination" it is meant a process of exchange of genetic information between two polynucleotides. As used herein, "homologous recombination" or "HR" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and leads to the transfer of genetic information from the donor to the target. Homologous recombination may result in an alteration of the sequence of the target molecule, if the donor polynucleotide differs from the target molecule and part or all of the sequence of the donor polynucleotide is incorporated into the target polynucleotide. Thus the nucleotide sequence A comprises a recombination cassette, also called herein "docking platform" or "landing pad", flanked by 5' and 3' target gene homology arms. In particular embodiment, since the target gene is the CCR5 gene, the recombination cassette is flanked by 5' and 3' CCR5 homology arms.

Any recombinant endonuclease may be used for carrying out the homology recombination and to integrate the nucleotide sequence A into the target gene, such as the CCR5 gene. Examples of endonucleases include, but without limiting to, zinc finger nuclease or "ZFN", CRISPR/Cas9 endonuclease, and TAL Nuclease or "TALEN". In a particular embodiment, the endonuclease used in step (a) from the method of the invention is TALEN nuclease.

TAL Nuclease ("TALN", TAL effector nuclease, or "TALEN") is a targeted nuclease comprising a nuclease fused to a TAL effector DNA binding domain. By "transcription activator-like effector DNA binding domain", "TAL effector DNA binding domain", or "TALE DNA binding domain" it is meant the polypeptide domain of TAL effector proteins that is responsible for binding of the TAL effector protein to DNA.

The endonuclease(s) may be provided to the cells prior to, simultaneously with, or subsequent to, contacting the cells with the nucleotide sequence A. If transiently expressed by the cells, the targeted nuclease(s) may be provided to cells as DNA, e.g. plasmid or vector, as described herein, e.g., by using transfection, nucleofection, or the like. Alternatively, endonuclease(s) may be provided to cells as mRNA encoding the targeted nuclease(s), e.g. using well-developed transfection techniques; or the commercially available TransMessenger® reagents from Qiagen, Stemfect™ RNA Transfection Kit from Stemgent, and TransIT®-mRNA Transfection Kit from Minis Bio LLC. Alternatively, the endonuclease(s) may be provided to cells as a polypeptide.

The step of introducing a nucleic acid into the human cell may be carried out by any method known in the art. For example, a nucleic acid may be introduced into a human cell by injection (into the nucleus or cytoplasm), transfection, viral infection, nucleofection, electroporation, calcium chloride transfection, and lipofection, and the like. A nucleic acid can be introduced as a naked nucleic acid or as a nucleic acid complexed with an agent such as a liposome or a stabilizing agent, and the like.

The method of the invention comprises in step (a) the use of a nucleotide sequence A comprising a recombination cassette comprising, in this order (i.e. in the 5'-end to 3'-end direction),
(i) a serine-integrase attB attachment site,
(ii) a right-ITR element specific for a first transposase,
(iii) a genetic construction comprising, at least one, first recombinant site and
(iv) a selection marker flanked by ITR elements specific for a second transposase different from the first transposase.

The elements present in the nucleotide sequence A are the basis for inserting multiple recombinant sites in successive steps of the method.

The first element is a serine-integrase attB attachment site, also known as attB site. As used herein, a serine-integrase attachment site is a DNA sequence which works as "recognition site" which serves a substrate for a recombinase, in particular, a serine-integrase, so that to provide for unidirectional site-specific recombination. The integrases catalyze the site-specific recombination between phage attachment sites (attP) and bacterial attachment site (attB). The attP and attB are relatively short, yet long enough to be specific on a genomic scale. Example of serine-integrase include, without limiting to, phiC31 (177), Bxb1 (186; 187), Rv1, A118, TP901-1, φBT1, φC1, MR11, TP901-1, R4, A118, φRV, TG1, φ370.1, WB, BL3, SPBc and K38. Any of them can be used in the present invention. However, in a particular embodiment of the method of the invention, the integrase is PhiC31. The terms "integrase" and "recombinase" are equivalent and are used interchangeably herein. Integrase is required for both integration an excision, but excision requires a phage-encoded accessory protein named recombination directionality factor (RDF), to control de activity of the integrase. In the absence of RDF, all phage integrases are unidirectional, mediating only integration.

PhiC31 is the most studied integrase. It is active in human cells, catalyzing both intramolecular and intermolecular recombination. PhiC31 integrases consist of a conserved N-terminal domain essential for DNA cleavage, strand exchange, and protein-protein interactions and a large C-terminal domain, which is required for DNA binding. In an attempt to improve phiC31 recombination efficiency, distinct mutations are introduced in the N-terminal and the C-terminal domains. Integrase is required for both integration an excision, but excision requires a phage-encoded accessory protein named recombination directionality factor (RDF), to control de activity of the integrase. In the absence of RDF, all phage integrases are unidirectional, mediating only integration. As explained above, RDFs are involved in the excision reaction of integrases. The phiC31 RDF is a 27.5 kDa protein encoded by the gp3 gene. Gp3 induces attL/attR recombination and inhibits attP/attB recombination in a stoichiometric rather than a catalytic manner.

The serine-integrase attachment site used in nucleotide sequence A will be an attB site specific for a serine-integrase, in particular, specific for PhiC31, so that it could be used as an integration site for other nucleotide sequences in successive steps of the method of the invention, when a second or more recombinant sites are to be inserted in the target gene.

Another element of nucleotide sequence A is (ii) a right-ITR element specific for a first transposase. As used herein, a DNA transposase is an enzyme which performs excision and insertion process of a DNA sequence flanked by inverted terminal repeats (ITRs) in their original orientation. Any transposase can be used in the method of the invention as long as they belong to non-replicative DNA transposons (Class II, Subclass I, of transposons). Examples of transposons/transposases include, without limited to, Tc1/mariner, PIF/Harbinger, hAT, Mutator, Merlin, Transib, P, Sleeping Beauty, piggyBac and CACTA. In a particular embodiment of the method of the invention, the first DNA transposase is a Sleeping Beauty transposase. The ITR element specific for a first DNA transposase will be used in successive steps of the method of the invention for removing the selection marker from the cell genome.

Another element of the nucleotide sequence A is a genetic construction comprising, at least one, first recombinant site. As used herein, "genetic construction" refers to a nucleotide sequence comprising one or more functional units not found in nature. In the present document, the terms "genetic construction" and "docking module" are equivalent and can be used interchangeably throughout the document. In a particular embodiment, the genetic construct comprises 1, 2, 3 or 4 first recombinant sites. As used herein, a "recombinant site" is a DNA region which serves a substrate for a recombinase, in particular, a serine-integrase, to provide for unidirectional site-specific recombination and to integrate a gene of interest (or a polynucleotide of interest or a transgene or a heterologous nucleotide sequence of interest) into the DNA. As used herein, the terms "recombinant site" and "docking site" are equivalent and can be used interchangeably throughout the document. In a particular embodiment, the recombinant site comprises a serine-integrase attB attachment site specific for a serine-integrase enzyme, wherein said serine-integrase enzyme is different from the serine-integrase enzyme used during the insertion of the at least one recombinant site in a target gene/locus. In a particular embodiment, the serine-integrase enzyme specific for uploading the gene of interest into the recombinant site is a Bxb1 enzyme.

Bxb1 recombinase has been used to insert a wide variety of genes into mammal cells. The integration is catalyzed by a 500 aa serine integrase that is composed of two domains, an N-terminal 150 aa catalytic domain, and a 350 aa C-terminal domain that confers DNA binding activity. The Bxb1 RDF, gp47, is a 30.6 kDa protein (255 aa) and contains a conserved domain of the protein phosphatase family. The biochemical mechanism of action of gp47 indicates that this protein does not directly bind to DNA, but instead controls integrase directionality through protein-protein interaction, similarly to gp3 function in the phiC31 system. Despite the weak interaction between gp47 and the attL/attR-bound integrase, gp47 can stimulate formation of the integrase: attL: attR synapse and the regeneration of attB and attP sites. When using phiC31 and Bxb1 in the same system, it is important to ensure that both recombinases cannot interact with each other. There are several studies showing that phiC31 does not recognize the Bxb1 attachment sites; conversely, Bxb1 does not interact with phiC31 attachment sites, regardless of whether they are isolated or present in the same integration plasmid. As explained in the beginning of the present description, the method of the invention is based on the use of two different serine-integrases: one integrase (for example phiC31) is used during the insertion of at least one recombinant site in a target gene/locus, and the other one (for example, Bxb1) is used in a posterior phase for the uploading of gene of interest into the recombinant site.

Finally, another element of the nucleotide sequence A is a selection marker flanked by ITR elements specific for a second DNA transposase different from the first transposase. The terms "ITR elements" and "DNA transposase" has been defined previously in the present description. Any transposase can be used as second transposase as long as it is different form the first transposase. Examples of transposons/transposases include, without limited to, Tc1/mariner, PIF/Harbinger, hAT, Mutator, Merlin, Transib, P, Sleeping Beauty, piggyBac and CACTA. In a particular embodiment of the method of the invention, the second DNA transposase is a piggyBac transposase.

The selection marker may be an "imaging marker". An imaging marker may be a non-cytotoxic agent that can be used to locate and, optionally, visualize cells, e.g. cells that have been targeted by nucleic acid compositions of the subject application. An imaging marker may require the addition of a substrate for detection, e.g., horseradish peroxidase (HRP), β-galactosidase, luciferase, and the like. Alternatively, an imaging marker may provide a detectable signal that does not require the addition of a substrate for detection, e.g. a fluorophore or chromophore dye, e.g. Alexa Fluor 488@ or Alexa Fluor 647®, or a protein that comprises a fluorophore or chromophore, e.g. a fluorescent protein. As used herein, a fluorescent protein (FP) refers to a protein that possesses the ability to fluoresce (i.e., to absorb energy at one wavelength and emit it at another wavelength). For example, a green fluorescent protein (GFP) refers to a polypeptide that has a peak in the emission spectrum at 510 nm or about 510 nm. A variety of FPs that emit at various wavelengths are known in the art. FPs of interest include, but are not limited to, a green fluorescent protein (GFP), yellow fluorescent protein (YFP), orange fluorescent protein (OFP), cyan fluorescent protein (CFP), blue fluorescent protein (BFP), red fluorescent protein (RFP), far-red fluorescent protein, or near-infrared fluorescent protein and variants thereof.

By a "selection marker" or "selectable marker" it is meant an agent that can be used to select cells, e.g., cells that have been targeted by the nucleotide sequences of the invention. In some instances, the selection may be positive selection; that is, the cells are isolated from a population, e.g. to create an enriched population of cells comprising the genetic modification. In other instances, the selection may be negative selection; that is, the population is isolated away from the cells, e.g. to create an enriched population of cells that do not comprise the genetic modification. Any convenient selectable marker may be employed, for example, a drug selectable marker, e.g. a marker that prevents cell death in the presence of drug, a marker that promotes cell death in the presence of drug, an imaging marker, etc.; an imaging marker that may be selected for using imaging technology, e.g. fluorescence activated cell sorting; a polypeptide or peptide that may be selected for using affinity separation techniques, e.g. fluorescence activated cell sorting, magnetic separation, affinity chromatography, "panning" with an affinity reagent attached to a solid matrix, etc.; and the like. In a particular embodiment of the method of the invention, the selection marker is puroΔTK (Puromycin-delta thymidine kinase).

To induce DNA integration in vitro, the culture under conditions that facilitate recombination may be carried out for 16-48 hours, after which time the media may be replaced with fresh media and the cells may be cultured further. Contacting the cells with the nucleotide sequences may occur in any culture media and under any culture conditions that promote the survival of the cells. For example, cells may be suspended in any appropriate nutrient medium, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Conditions that promote the survival of cells are typically permissive of nonhomologous end joining and homologous recombination.

Once that the nucleotide sequence A as disclosed above has been integrated into the target gene by homologous recombination, the method of the invention comprises a step (b) comprising the removal of the selection marker by using the second transposase, thus obtaining a cell genome A comprising elements (i), (ii) and (iii) of nucleotide sequence A, i.e. (i) a serine-integrase attB attachment site, (ii) a right-ITR element specific for a first DNA transposase, and (iii) a genetic construction comprising at least one first recombinant site.

The nucleotide sequence A of step (a) of the method of the invention allows, if desired, to integrate additional recombinant sites within the same target gene. Thus, in another aspect, the present invention also encompasses a nucleotide sequence comprising a recombination cassette flanked at 5' and 3' by target gene homology arms, comprising
  (i) a serine-integrase attB attachment site,
  (ii) a right-ITR element specific for a first transposase,
  (iii) a genetic construction comprising, at least one, first recombinant site and
  (iv) a selection marker flanked by ITR elements specific for a second transposase different from the first transposase.

Explanation, definitions and particular embodiments of the components of this nucleotide sequence have been explained above in the present description. As the skilled person understands, plasmids, vectors, cells and compositions comprising this nucleotide sequence are also encompassed in the present invention.

At this point, (1) a gene of interest (or a polynucleotide of interest or a transgene or a heterologous nucleotide sequence of interest) can be integrated into the cell genome A by site-specific recombination using a serine-integrase specific for the serine-integrase att site of the recombinant site (for example, a Bxb1 integrase), or alternatively, (2) a second recombinant site can be integrated in the cell genome A into the same target gene by additional site-specific recombination.

If a second recombinant site is going to be integrated into the same targeted locus of the cell genome A, the method of the invention further comprises the following steps
  (c) integrating a nucleotide sequence B into the cell genome A by the action of a serine-integrase recognizing both att sites of cell genome A and nucleotide sequence B, wherein said nucleotide sequence B comprises
    (i) a serine-integrase attP attachment site complementary to the serine-integrase attB site of step (a) (i) [which is present in the cell genome A],
    (ii) a right-ITR element specific for a transposase different from the first transposase of nucleotide sequence A,
    (iii) a genetic construction comprising, at least one, second recombinant site and
    (iv) a selection marker comprising in its 5' end a left-ITR element specific for the first transposase of nucleotide sequence A, and
  (d) removing the selection marker and the newly created hybrid attR attachment site by the use of the first transposase of nucleotide sequence A, thus obtaining a cell genome B comprising (i) a hybrid attL attachment site, elements (ii) and (iii) of the nucleotide sequence B, and element (iii) of the nucleotide sequence A.

Step (c) of the method of the invention comprises integrating a nucleotide sequence B into the cell genome A by the action of a serine-integrase recognizing both att sites of cell genome A and nucleotide sequence B. In order to do that, nucleotide sequence B comprises a serine-integrase attP attachment site complementary to the serine-integrase attB attachment site nucleotide sequence A (i) which, by carrying out steps (a) and (b), has been integrated into the cell genome. In a particular embodiment, serine-integrase which carries out the site-specific recombination is a PhiC31 integrase. The site-specific integration results in two new attachment sites: attL and attR. After integration, left- and right-ITRs first transposase recognition sites appear flanking a section of the newly incorporated DNA fragment that comprises the selection marker, the attR, and a portion of the recombination vector. This configuration facilitates the first transposase of nucleotide sequence A (specific for element (ii) of the cell genome A) to remove all the unnecessary elements after the right clones have been selected. The removal of the attR attachment site is critical to avoid interferences during the third recombination step.

Thus, nucleotide sequence B of step (c) of the method comprises
  (i) a serine-integrase attP attachment site complementary to the serine-integrase attachment site of nucleotide sequence A [element (i) of nucleotide sequence A],
  (ii) a right-ITR element specific for a transposase different from the first transposase of nucleotide sequence A,
  (iii) a genetic construction comprising at least one second recombinant site and
  (iv) a selection marker comprising at 5' a left-ITR element specific for the first transposase of nucleotide sequence A.

Component (i) of nucleotide sequence B is a serine-integrase attP attachment site complementary to the serine-integrase attB attachment site of nucleotide sequence A (element (i)). As explained previously, serine-integrase enzymes are enzymes which catalyze the site-specific recombination between phage attachment sites (attP) and bacterial attachment site (attB). Consequently, if the serine-integrase attachment site of nucleotide sequence A (i) (which is incorporated into the cell genome A) is an attB site, the serine-integrase attachment site of the nucleotide sequence B is an attP site so that the nucleotide sequence B is integrated into cell genome A by site-specific recombination. In a particular embodiment, the serine-integrase attachment site of nucleotide sequence B is specific of the PhiC31 integrase enzyme.

Component (ii) of nucleotide sequence B is a right-ITR element specific for a transposase different from the first transposase of nucleotide sequence A. The terms "ITR element" and "transposase" have been explained previously in the present description. In a particular embodiment, the right-ITR element is specific for a piggyBac transposase.

Component (iii) of nucleotide sequence B is a genetic construction comprising, at least one, second recombinant site. The terms "genetic construction" and "recombinant site" have been defined above in the present description together with the particular embodiments thereof.

Component (iv) of nucleotide sequence B is a selection marker comprising at 5' a left-ITR element specific for the first transposase of nucleotide sequence A. The purpose of this ITR element is to remove the selection marker and the attR attachment site after the site-specific recombination between cell genome A and nucleotide sequence B. Once the site-specific recombination has occurred between cell genome A and nucleotide sequence B, the selection marker and the attR site are flanked by the left-ITR element of nucleotide sequence A [element (a) (ii)] at its 5' end and by the right-ITR element of nucleotide sequence B at its 3' end.

Next, in step (d), the genetic material comprised within these ITR elements is removed by a transposase specific for the ITR elements, i.e. the first transposase of nucleotide sequence A, obtaining a cell genome B comprising (i) a hybrid attL attachment site for a serinee-integrase, elements (ii) and (iii) of the nucleotide sequence B, and element (iii) of the nucleotide sequence A. In a particular embodiment of the method of the invention, the first transposase of nucleotide sequence A is the Sleeping Beauty transposase.

Additionally, in case that another recombinant site is wanted to be integrated within the same targeted locus of the cell genome, the method of the invention comprises further steps (e) and (f).

Step (e) comprises integrating a nucleotide sequence C into the cell genome B, by the action of a serine-integrase recognizing the hybrid attL attachment site of the cell genome B and the hybrid attR attachment site of the nucleotide sequence C, being the last complementary to the hybrid attachment site of the cell genome B, wherein the action of the serine-integrase comprises the presence of a recombination directionality factor. In a particular embodiment, the serine-integrase enzyme used for carrying out step (e) is phiC31. In this step of the method of the invention, this integrase exert its activity together with a recombination directionality factor which, in a particular embodiment, is gp3. The phiC31 RDF is a 27.5 kDa protein encoded by the gp3 gene. Gp3 induces attL/attR recombination and inhibits attP/attB recombination in a stoichiometric rather than a catalytic manner.

Site-specific integration resulted in recombination between the attL and attR sites, thus regenerating the attB and attP sites. After integration, the right-ITR specific for the transposase of the nucleotide sequence B is located at the 3'end of the selection marker in the correct orientation to allow the activity of the transposase which leads to the removal of the attP site as well as vector fragments and the selection marker. In a particular embodiment, the transposase is the piggyBac transposase.

Thus, nucleotide sequence C comprises
(i) a serine-integrase hybrid attR attachment site complementary to the hybrid attL attachment site of cell genome B,
(ii) a right-ITR element specific for the first transposase of nucleotide sequence A,
(iii) a genetic construction comprising at least one, third recombinant site and
(iv) a selection marker comprising in its 5' end a left-ITR element specific for the transposase of the nucleotide sequence B integrated into the cell genome B.

The terms "serine-integrase", "transposase", "ITR-element", "genetic construction" and "selection marker" have been defined above in previous embodiments of the method of the invention. Said definitions, as well as the particular embodiments of each term, are applicable to the present embodiment.

Next, step (f) comprises removing the selection marker and the newly created attP attachment site by the use of the transposase of nucleotide sequence B, thus obtaining a cell genome C comprising (i) serine-integrase attB attachment site, elements (ii) and (iii) of nucleotide sequence C, element (iii) of nucleotide sequence B, and element (iii) of nucleotide sequence A. In a particular embodiment, the transposase of nucleotide sequence B is piggyBac transposase.

As can be appreciated, the sequential implementation of the steps described above [steps (a) to (f)] constitutes a complete cycle of integration and after the cycle of the method of the invention, the cell genome obtained (cell genome C) comprises the same structural elements that the cell genome resulting from steps (a) and (b), i.e. cell genome A, but with two additional recombinant sites. This common structure makes it possible to continue adding as many new recombinant sites as needed by simply repeating steps (c) to (f) of the method of the invention.

Therefore, in another particular embodiment, the method of the invention additionally comprises
(g) Carrying out step (c) and (d) if one additional recombinant site is going to be inserted into the same target gene of the cell genome, or
(g') Carrying out steps (c), (d), (e) and (f) if two additional recombinant sites are going to be inserted into the target gene of the cell genome,
wherein steps (g) or (g') are repeated as many times as recombinant sites are to be inserted into the target gene from the cell genome.

Nucleotide sequences A, B and C of the method of the invention comprise a genetic construction comprising at least one recombinant site. In a particular embodiment, the genetic construction comprises 1, 2, 3 or 4 recombinant sites. Each recombination site comprises not only an attB site which serves a substrate for a recombinase, in particular, a serine-integrase, to provide for unidirectional site-specific recombination and to upload a gene of interest into the DNA of a cell, but also the necessary elements to promote the expression of said gene of interest.

Thus, in another particular embodiment, the recombination site (also called "docking site" in the present invention) of the genetic construction (also called "docking module" in present invention) comprises a transcriptional unit comprising, in this order (i.e. in the 5'-end to 3'-end direction),
(a) an insulator,
(b) a promoter, and
(c) a serine-integrase att site specific for a serine-integrase different from the serine-integrase used during the insertion of the recombinant site in the target gene/locus of the cell genome.

As used herein "Insulators" are a class of DNA elements that possess a common ability to protect genes from inappropriate signals emanating from their surrounding environment. Insulators can act as a positional enhancer blocker; if the insulator is situated between an enhancer and a promoter, then enhancer-mediated activation of the promoter is impaired by the insulator. If the insulator lies outside the region between enhancer and promoter little or no effect is observed. Insulators also have the ability to protect against position effects by acting as barriers, preventing the advance of nearby condensed chromatin that might otherwise silence expression. Transgene activity is often affected by chromosomal position effects. In conclusion, it is crucial to use insulators between the single loading sites in order to prevent silencing of transgenes integrated in the docking module or run off effects from one promoter over neighboring ones. In addition, insulator may also protect the genome from the insertional activation of surrounding proto-oncogenes, a very important consideration for cell therapy applications. Any insulator can be used in the context of the present invention. However, in a particular embodiment, the insulator is cHS4, derived from the chicken β-globin locus. The cHS4 element is the best characterized, flanking transgene, already tested in many cell lines. Besides the insulator type it is important to determine the number and position of the insulator elements in the docking module. This is routine practice for the skilled person in the art. The cHS4 insulator alleviates transcriptional interference occurring between two neighboring transgenes positioned at both sides of the transgenes and it has been described that a single element is enough to achieve higher and long-term transgenes expression levels. In a particular embodiment of the present invention, only one cHS4 insulator element was placed 5' upstream of promoter to guarantee the function of each transcriptional unit while minimizing the size of the docking vector.

As used herein, the term "promoter" refers a region of DNA that initiates transcription of a particular gene. Promoters are located near the transcription start sites of genes, on the same strand and upstream on the DNA. Promoters can be about 100-1000 base pairs long. The choice of promoter has a great impact on both the level and the duration of transgene expression. Examples of promoters include, but without limiting to, an androgen or estrogen-responsive promoter, a doxycicline-responsive promoter, a metallothionein promoter, or a promoter responding to ecdysone cytomegalovirus (CMV) immediate-early promoter, and the Rous sarcoma virus promoter. In a particular embodiment of the present invention, the recombinant site was designed and constructed with the small but strong SV40 promoter, which is frequently used to achieve high levels of expression in a variety of mammal cell and tissue types. The SV40 promoter was cloned 5' upstream of the Bxb1 attachment site, so that only successful recombination events could give rise to cell clones with correct transgene expression. As the loading vector lacks a promoter element, randomly integrated transgenes will not be expressed in the cells. In another particular embodiment, the promoter is the human eukaryotic translation elongation factor 1 alpha 1 (EEF1A1) promoter. This promoter improves transgene expression and prevents potential silencing events.

Finally, the recombination site comprises a serine-integrase att site specific for a serine-integrase different from the serine-integrase used during the insertion of the recombinant site in the target gene/locus of the cell genome. The term "serine-integrase" has been defined previously in the present description. In a particular embodiment, the serine-integrase att site is a serine-integrase specific attB site. In a more particular embodiment, the serine-integrase attB site is the bxb1 serine-integrase specific attB site.

In a particular embodiment of the method of the invention, the nucleotide sequences A, B and C are integrating circular plasmids or vectors.

As can be seen FIG. 1, in a more particular embodiment resulting from combining all the particular embodiments herein disclosed, the present invention relates to an in vitro method for inserting at least one recombinant site in the CCR5 gene from a mammal cell genome, said method comprising
(a) integrating a nucleotide sequence A into the CCR5 gene from an isolated mammal cell genome by homologous recombination, wherein said nucleotide sequence A comprises a recombination cassette, flanked at 5' and 3' by CCR5 homology arms, comprising
    (i) a PhiC31 attB attachment site,
    (ii) a right-ITR element specific for a Sleeping Beauty transposase,
    (iii) a genetic construction comprising, at least one, first Bxb1-specific attB site, and
    (iv) a puroΔTK selection marker flanked by ITR elements specific for a piggyBac transposase, and
(b) removing the selection marker by using the piggyBac transposase, thus obtaining a cell genome A comprising (i), (ii) and (iii) of nucleotide sequence A, and/or
(c) integrating a nucleotide sequence B into the cell genome A by the action of a serine-integrase recognizing both att sites of cell genome A and nucleotide sequence B, wherein said nucleotide sequence B comprises
    (i) a PhiC31 attP attachment site complementary to the serine-integrase attachment site of nucleotide sequence A (i),
    (ii) a right-ITR element specific for a piggyBac transposase,
    (iii) a genetic construction comprising, at least one, second Bxb1-specific attB site, and
    (iv) a puroΔTK selection marker comprising in its 5' end a left-ITR element specific for the sleeping beauty transposase, and
(d) removing the selection marker by the use of the sleeping beauty transposase, thus obtaining a cell genome B comprising (i) a phiC31 attL attachment site, elements (ii) and (iii) of the nucleotide sequence B, and element (iii) of the nucleotide sequence A, and/or
(e) integrating a nucleotide sequence C into the cell genome B, by the action of PhiC31 integrase in combination with gp3, recognizing the attL attachment site of the cell genome B and the attR attachment site of the nucleotide sequence C, wherein nucleotide sequence C comprises
    (i) a PhiC31 hybrid attR attachment site complementary to the PhiC31 attL attachment site of cell genome B,
    (ii) a right-ITR element specific for the sleeping beauty transposase,
    (iii) a genetic construction comprising at least one, third Bxb1-specific attB site, and
    (iv) a puroΔTK selection marker comprising in its 5' end a left-ITR element specific for the piggyBac transposase of the nucleotide sequence B integrated into the cell genome B, and
(f) removing the selection marker by the use of the piggyBac transposase, thus obtaining a cell genome C comprising (i) PhiC31 attB attachment site, elements (ii) and (iii) of nucleotide sequence C, element (iii) of nucleotide sequence B, and element (iii) of nucleotide sequence A, and/or
(g) Carrying out step (c) and (d) if one additional recombinant site is going to be inserted into the same target gene of the cell genome, or
(g') Carrying out steps (c), (d), (e) and (f) if two additional recombinant sites are going to be inserted into the target gene of the cell genome, wherein steps (g) or (g') are repeated as many times as recombinant sites are to be inserted into the CCR5 gene from the iPS cell genome, and
wherein the genetic construction of nucleotide sequences A, B y C comprises 1, 2, 3 or 4 recombinant sites, each recombinant site comprising
    (a) a CHS4 insulator,
    (b) a SV40 promoter, and
    (c) a BxB1 integrase attB site.

After putting into practice the method of the invention, it is obtained a cell whose genome comprises at least one recombinant site which can be used for inserting a gene of interest or transgene.

Thus, in another aspect, the present invention relates to an in vitro method for loading a gene of interest into a cell genome, hereinafter "second method of the invention", comprising
(a) inserting a recombinant site into the cell genome by the method of the invention, and
(b) introducing the gene of interest by means of a serine-integrase specific for the serine-integrase attB attachment site comprised within the recombinant site inserted into the cell genome according to step (a).

As used herein, a "gene of interest" or "a polynucleotide sequence of interest" is a DNA sequence that is transcribed into RNA and in some instances translated into a polypeptide in vivo when placed under the control of appropriate regulatory sequences. A gene or polynucleotide of interest can include, but is not limited to, prokaryotic sequences, cDNA from eukaryotic mRNA, genomic DNA sequences from eukaryotic (e.g., mammal) DNA, and synthetic DNA sequences. For example, a gene of interest may encode an miRNA, an shRNA, a native polypeptide (i.e. a polypeptide found in nature) or fragment thereof; a variant polypeptide (i.e. a mutant of the native polypeptide having less than 100% sequence identity with the native polypeptide) or fragment thereof; an engineered polypeptide or peptide fragment, a therapeutic peptide or polypeptide, an imaging marker, a selectable marker, and the like.

Any gene of interest can be loaded into the target locus, for example, any gene encoding a siRA, shRA, miRNA, CRISPRi element, peptide, or polypeptide may be integrated. Additionally, as discussed above, more than one gene of interest may be integrated, for example, two or more genes of interest may be integrated, three or more genes may be integrated, four or more genes may be integrated, e.g. five or more genes may be integrated. Thus, for example, in embodiments where the genetically modified cell is a ES or PS or iPS cell, the one of more polynucleotide sequences/ genes of interest may be transcription factors that promote the differentiation of these cells into a particular cell lineage. For example, the subject methods may be used to convert iPS generated from a somatic cell isolated from a subject in need of a particular cell type into the particular cell type. Since the cells to be transplanted into the subject are derived from the subject's cells, any immune response to the transplanted cells may be reduced or avoided. Other genes of interest may be those encoding for a therapeutic agent or for proteins to be tested or produced in the targeted cell. More details about genes of interest which can be inserted in a cell, preferably, a mammal cell, more preferably, a human cell, will be provided bellow together with the utilities thereof.

Step (a) of the second method of the invention comprises inserting a recombinant site into the cell genome by the method of the invention. The method of the invention and the particular embodiments thereof has been disclosed above. As a result of putting into practice step (a), it is obtained a cell whose genome comprises at least one recombinant site comprising a serine-integrase attB site. Next, step (b) of the second method of the invention, comprises introducing the gene of interest by means of a serine-integrase specific for the serine-integrase attB attachment site comprised within the recombinant site inserted into the cell genome according to step (a). In order to this, the gene of interest is comprised in a vector or plasmid.

As used herein, the term "vector" or "plasmid" refers to any vehicle used to transfer foreign genetic material into another cell. Said vector can be a viral vector or a non-viral vector, such as a plasmid. By way of a non-limiting illustration, said vectors can be viral vectors based on retroviruses, adenoviruses, alphaviruses, etc., or in case of non-viral vectors, the vectors can be DNA-liposome, DNA-polymer, DNA-polymer-liposome complexes, pSilencer 4.1-CMV (Ambion), pcDNA3, pcDNA3.1/hyg pHCMV/ Zeo, pCR3.1, pEFI/His, pIND/GS, pRc/HCMV2, pSV40/ Zeo2, pTRACER-HCMV, PUB6/V5-His, pVAXI, pZeoSV2, pCI, pSVL and pKSV-10, pBPV-1, pML2d, pTDTI, etc. Said viral and non-viral vectors comprising the polynucleotide encoding in its natural state a fluorescent protein can be administered to the cell by the conventional methods previously cited.

The vector can contain, among others, multiple cloning sites, expression regulating sequences, suitable replication origins for the host cell in which the vector is introduced, selection markers, etc. In a particular embodiment, the vector is an expression vector which allows the expression of the polynucleotide in the target cell and generally has a promoter sequence (or expression regulating sequences) that drives expression thereof. The promoter sequence preceding the polynucleotide is operatively bound to the said polynucleotide. As used in this description, the expression "operatively bound" means that the polynucleotide is within the correct reading frame for their expression under the control of said regulating sequences. The regulating sequences useful for the present invention can be nuclear promoting sequences or, alternatively, enhancer sequences and/or other regulating sequences increasing the expression of the polynucleotide. The promoter can be constitutive or inducible. If the constant expression of the polynucleotide is desired, then a constitutive promoter is used. Examples of well-known constitutive promoters include the cytomegalovirus (CMV) immediate-early promoter, the Rous sarcoma virus promoter, and the like. A number of other examples of constitutive promoters are well known in the art and can be used in implementing the invention. If the controlled expression of the polynucleotide is desired, then an inducible promoter must be used. In a non-induced state, the inducible promoter must be "silent". "Silent" is understood to mean that in the absence of an inducer, little or no expression of the polynucleotide is detected; in the presence of an inducer, however, the expression of the polynucletide occurs. The expression level can frequently be controlled by varying the concentration of the inducer so that the inducible promoter is stimulated more strongly or weakly and consequently, the concentration of the polynucletido transcribed product is affected. Examples of well-known inducible promoters are: an androgen or estrogen-responsive promoter, a doxycicline-responsive promoter, a metallothionein promoter, or a promoter responding to ecdysone. Other various examples are well known in the art and can be used for implementing the invention.

In a particular embodiment, the gene of interest is comprised within a genetic construction comprising, in this order,
(i) a serine-integrase attP attachment site specific for a serine-integrase which recognizes the serine-integrase attB attachment site comprised within the recombinant site,
(ii) the gene of interest, and
(iii) a selection marker flanked by two ITR elements specific for a non-replicative DNA transposase. The terms used in this particular embodiment has been defined and explained above in previous paragraphs. In another embodiment, the gene construction is comprised within an integrating circular plasmids or vectors.

In a more particular embodiment of the second method of the invention, the serine integrase is a Bxb1 serine-integrase, the selection marker is puroΔTK, and/or the gene of interest encodes for a protein selected from
fluorescent proteins including, but not limited to, EGFP and mCherry, among others,
transcription or growth factors including, but not limited to, Wnt-3A, Noggin or Activin-A,
cytokines including, but not limited to, IL-2, and
antibodies including, but not limited to monoclonal antibodies, such as IgE mAb, IgG mAb, IgM mAb, IgD mAb, etc.

In another particular embodiment, the second method of the invention comprises a further step (c) comprising removing the selection marker by the action of a transposase specific for the ITR elements flanking the selection marker. As explained for previous embodiments of the present invention, any non-replicative DNA transposase. Examples of non-replicative DNA transposase has been cited previous paragraphs. Nevertheless, in a more particular embodiment, the transposase is the piggyBac transposase.

As can be seen in FIG. 2, in a more particular embodiment of the second method of the invention resulting from combining all the particular embodiments herein disclosed, the present invention relates to an in vitro method for loading a gene of interest into a iPS cell genome, comprising
(a) inserting an Bxb1 attB recombinant site into the cell genome by the method of the invention, and
(b) introducing the gene of interest by means of a Bxb1 integrase,
wherein the gene of interest is comprised within a genetic construction comprising, in this order,
(i) a Bxb1 attP attachment site specific for Bxb1 integrase,
(ii) the gene of interest, and
(iii) a puroΔTK selection marker flanked by two ITR elements specific for piggyBac transposase.

The terms used in this particular embodiment has been defined and explained above in previous paragraphs.

In a particular embodiment of the second method of the invention, the nucleotide sequences A, B and C are integrating circular plasmids or vectors, as explained above.

Nucleotide Sequences of the Invention

In order to develop the method of the invention, the inventor designed a set of nucleotide sequences whose elements are organized in such a way that multiple recombinant sites can be integrated into a sole target gene in the cell genome. As can be seen in the disclosure of the method of the invention, these sequences are nucleotide sequences A, B and C.

As pointed out in the beginning of the present description, for the shake of clarity, the nucleotide sequences of the invention disclosed herein refers to a serine-integrase attB attachment site in element (i) of nucleotide sequence A of the invention. However, as the skilled person in the art understands, the attB site of element (i) can be replaced with attP attachment site as long as the complementarity between the attB/attP, attP/attB, attL/attR and attR/attL is maintained throughout nucleotide sequences B and C of the invention as disclosed below. For example, a attP site in nucleotide sequence A can be used instead of the attB site if the inverse substitution, attP by attB, is also done in the nucleotide sequence B (see below).

Thus, in one aspect, the present invention relates to a nucleotide sequence, hereinafter nucleotide sequence A of the invention, comprising a recombination cassette, flanked at 5' and 3' by target gene homology arms, comprising
(i) a serine-integrase attB attachment site,
(ii) a right-ITR element specific for a first transposase,
(iii) a genetic construction comprising, at least one, recombinant site, and
(iv) a selection marker flanked by ITR elements specific for a second transposase different from the first transposase.

In a particular embodiment, nucleotide sequence A of the invention comprises a recombination cassette, flanked at 5' and 3' by target gene homology arms, wherein
(i) the serine-integrase attB attachment site is a PhiC31-specific attB attachment site, and/or
(ii) the first transposase is a sleeping Beauty transposase, and/or
(iii) the recombinant site of the genetic construction comprises a Bxb1 integrase attB attachment site, and/or
(iv) the second transposase is a piggyBac transposase.

Nucleotide sequence A of the invention allows integrating at least one recombinant site within the same target gene.

In another aspect, the present invention relates to a nucleotide sequence, hereinafter nucleotide sequence B of the invention, comprising
(i) a serine-integrase attP attachment site complementary to the serine-integrase attachment site of nucleotide sequence A (i) of the method of the invention,
(ii) a right-ITR element specific for a transposase different from the first transposase of nucleotide sequence A,
(iii) a genetic construction comprising, at least one, recombinant site, and
(iv) a selection marker comprising at 5' a left-ITR element specific for the first transposase of nucleotide sequence A.

In a particular embodiment, nucleotide sequence B of the invention comprises a recombination cassette, wherein
(i) the serine-integrase attP attachment site is a PhiC31 attP attachment site, and/or
(ii) the transposase different from the first transposase is a piggyBac transposase, and/or
(iii) the recombinant site of the genetic construction is a Bxb1 integrase attB attachment site, and/or
(iv) the first transposase is a sleeping Beauty transposase.

In another aspect, the present invention relates to a nucleotide sequence, hereinafter nucleotide sequence C of the invention, comprising
(i) a serine-integrase hybrid attR attachment site complementary to the hybrid attL attachment site of cell genome B,
(ii) a right-ITR element specific for the first transposase of nucleotide sequence A,
(iii) a genetic construction comprising at least one, third recombinant site, and
(iv) a selection marker comprising in its 5' end a left-ITR element specific for the transposase of the nucleotide sequence B integrated into the cell genome B.

In a particular embodiment, nucleotide sequence C of the invention comprises a recombination cassette, wherein
(i) the serine-integrase hybrid attR attachment site is a PhiC31 hybrid attR attachment site, and/or
(ii) the first transposase is a sleeping Beauty transposase, and/or
(iii) the recombinant site of the genetic construction comprises a Bxb1 integrase attB attachment site, and/or (iv) the transposase of the nucleotide sequence B integrated into the cell genome B is a piggyBac transposase.

Nucleotide sequences A, B and C of the invention are used throughout the different steps of the method of the invention.

Explanations, definitions and particular embodiments of the components of the nucleotide sequences of the invention have been explained above for the method of the invention, and are applicable to the nucleotide sequences of the invention. As the skilled person understands, plasmids, vectors, cells and compositions comprising these nucleotide sequences are also encompassed in the present invention.

Additionally, in order to integrate a gene of interest into the recombinant site introduced in the cell genome by the method of the invention, the inventors have developed another nucleotide sequence harboring the gene of interest. Thus, in another aspect, the present invention relates to a nucleotide sequence, hereinafter "nucleotide sequence D of the invention", comprising a genetic construction comprising, in this order,
(i) a serine-integrase attP attachment site specific for a serine-integrase which recognizes the serine-integrase attB attachment site comprised within the recombinant site,
(ii) the gene of interest, and
(iii) a selection marker flanked by two ITR elements specific for a non-replicative DNA transposase.

The terms used in this aspect of the invention have been defined and explained above in previous paragraphs, as well as all the particular embodiments thereof.

In a particular embodiment, the nucleotide sequence comprising the gene of interest comprises
(i) a Bxb1 attP attachment site,
(ii) the gene of interest, and
(iii) a selection marker flanked by two ITR elements specific for a piggyBac transposase.

The terms used in this aspect of the invention have been defined and explained above in previous paragraphs, as well as all the particular embodiments thereof.

The nucleotide sequences provided by this invention can be inserted into an appropriate vector. Thus, in another aspect, the present invention relates to a circular vector or plasmid, hereinafter "vector of the invention", comprising one or more of the nucleotide sequences of the invention as disclosed in previous paragraphs of the present description. As the skilled person in the art knows, the vector of the invention can comprise several elements such as, without limiting to, regulatory sequences (enhancers, promoters, etc.) functional in the cell to be transformed, a replication origin functional in the cell to be transformed, and genetic markers (such as genes which confer resistance to antibiotics, for example, ampicillin, tetracycline, kanamycin, hygromycin, gentamicin, etc.).

In another aspect, the present invention relates to a cell comprising one or more of the nucleotide sequences of the invention and/or the vector of the invention.

In another aspect, the present invention relates to a composition comprising one or more of the nucleotide sequences of the invention, the vector of the invention, and/or the cell comprising one or more of the nucleotide sequences of the invention and/or the vector of the invention.

Genetically Modified Cells of the Invention

After putting into practice the method of the invention, it is obtained a cell whose genome comprises at least one recombinant site. Thus the present invention also provides genetically modified cells.

In another aspect, the present invention relates to a genetically modified cell obtained by the method of the invention, hereinafter "cell obtained by the first method of the invention". In another aspect, the present invention relates to a genetically modified cell obtained by the second method of the invention, hereinafter "cell obtained by the second method of the invention".

In another aspect, the present invention relates to a cell, hereinafter "cell of the invention", comprising integrated into its genome a nucleotide sequence comprising, in this order,
(i) serine-integrase attB attachment site,
(ii) a right-ITR element specific for a non-replicative DNA transposase, and
(iii) at least one genetic construct (also called "docketing module") comprising at least one recombinant site (also called "docketing site").

In a particular embodiment, the cell of the invention comprises 2 or 3 genetic constructions and/or each genetic construction comprises 2, 3, or 4 recombinant sites.

In another particular embodiment, the recombinant site comprises transcriptional unit comprising, in this order,
(a) an insulator,
(b) a promoter, and
(c) a serine-integrase attB site specific for a serine-integrase different from the serine-integrase used during the insertion of the recombinant site in the target gene/locus of the cell genome.

In another particular embodiment, the recombinant site of the cell of the invention comprises a gene of interest.

The present invention also encompasses cells comprising the nucleotide sequences of the invention, i.e. nucleotide sequence A, B, C and D of the invention as disclosed above. Thus, in another aspect, the present invention relates to a cell comprising the nucleotide sequence A of the invention, the nucleotide sequence B of the invention, or the nucleotide sequence C of the invention. In another aspect, the present invention relates to a cell comprising a vector comprising one or more of the nucleotide sequences of the invention. In another aspect, the present invention also relates to a composition comprising one or more of the nucleotide sequences of the invention, one or more of the cells of the invention, or one or more of the vectors comprising the nucleotide sequences of the invention.

Any human cell's genome may be modified by the nucleic acid compositions and methods described herein. For example, the cell may be a meiotic cell, a mitotic cell, or a post-mitotic cell. Mitotic and post-mitotic cells of interest in these embodiments include pluripotent stem cells and their derivatives, e.g. ES cells, iPS cells, and embryonic germ cells; adult stem cells, e.g. hematopoietic stem cells, and somatic cells, e.g. fibroblasts, neurons, muscle cells, bone cells, vascular endothelial cells, gut cells, and the like, and their lineage-restricted progenitors and precursors.

Additional examples of cells include, without limited to, insect cells, vegetal cells, and mammal cells. These cells can be somatic cells, adult tissue specific stem cells, pluripotente stem cells embryonic stem cells, and induced pluripotent stem cells and their derivatives. In a particular embodiment, the mammal cell is a human cell, a CHO cell (Chinese hamster ovary cell) or a 3T3 cell (primary mouse embryonic fibroblast cell). Examples of human cells include, without limiting to, cell lines, such as Hela cells, somatic cells, adult tissue specific stem cells, pluripotent stem cells embryonic stem cells, and induced pluripotent stem cells and their derivatives. In a particular embodiment, the cells of the invention are an induced pluripotent stem cell. In another particular embodiment, the cells of the invention are a human HeLa cell line or hiPS cell line.

Separation of genetically modified cells typically relies upon the expression of a selectable marker that is co-integrated into the target locus. By a "selectable marker" it is meant an agent that can be used to select cells. In some instances, the selection may be positive selection; that is, the cells are isolated from a population, e.g. to create an enriched population of cells comprising the genetic modification. In other instances, the selection may be negative selection; that is, the population is isolated away from the cells, e.g. to create an enriched population of cells that do not comprise the genetic modification. Separation may be by any convenient separation technique appropriate for the selectable marker used. For example, if a fluorescent marker has been inserted, cells may be separated by fluorescence activated cell sorting, whereas if a cell surface marker has been inserted, cells may be separated from the heterogeneous population by affinity separation techniques, e.g. magnetic separation, affinity chromatography, "panning" with an affinity reagent attached to a solid matrix, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the genetically modified cells.

Cell compositions that are highly enriched for cells comprising the polynucleotide sequence of interest are achieved in this manner. By "highly enriched", it is meant that the genetically modified cells will be 70% or more, 75% or more, 80% or more, 85% or more, 90% or more of the cell composition, for example, about 95% or more, or 98% or more of the cell composition. In other words, the composition may be a substantially pure composition of genetically modified cells.

Genetically modified cells produced by the methods described herein may be used immediately. Alternatively, the cells may be frozen at liquid nitrogen temperatures and stored for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

The genetically modified cells may be cultured in vitro under various culture conditions. The cells may be expanded in culture, i.e. grown under conditions that promote their proliferation. Culture medium may be liquid or semi-solid, e.g. containing agar, methylcellulose, etc. The cell population may be suspended in an appropriate nutrient medium, such as Iscove's modified DMEM or RPMI 1640, normally supplemented with fetal calf serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

Cells that have been genetically modified in this way may be transplanted to a human subject for purposes such as gene therapy, e.g. to treat a disease, or as an antiviral, antipathogenic, or anticancer therapeutic. The subject may be a neonate, a juvenile, or an adult.

The genetically modified cells of the present invention may be formulated into cell compositions that are pharmaceutical compositions that include a pharmaceutically acceptable carrier. Examples of pharmaceutically acceptable carriers include saline, buffers, diluents, fillers, salts, stabilizers, solubilizers, cell culture medium, and other materials which are well known in the art. In some embodiments, the formulations are free of detectable DMSO (dimethyl sulfoxide).

Cells may be modified in vitro or in vivo. If modified in vitro, cells may be from established cell lines or they may be primary cells, where "primary cells", "primary cell lines", and "primary cultures" are used interchangeably herein to refer to cells and cells cultures that have been derived from a subject, such as, a human subject and either modified without significant additional culturing, i.e. modified "ex vivo", e.g. for return to the subject, or allowed to grow in vitro for a limited number of passages, i.e. splittings, of the culture. For example, primary cultures are cultures that may have been passaged 0 times, 1 time, 2 times, 4 times, 5 times, 10 times, or 15 times. Typically, the primary cell lines of the present disclosure are maintained for fewer than 10 passages in vitro.

If the cells are primary cells, they may be harvested from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, nervous system, etc., are most conveniently harvested by biopsy. An appropriate solution may be used for dispersion or suspension of the harvested cells. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40%>buffered medium, or some other such solution as is commonly used in the art to preserve cells at such freezing temperatures, and thawed in a manner as commonly known in the art for thawing frozen cultured cells.

Utilities of the Method and Cells of the Invention

The nucleotide sequence compositions, cell compositions, and methods disclosed herein find use in any in vitro or in vivo application in which it is desirable to express one or more polynucleotide sequences/genes of interest in a cell, preferably, an animal cell, more preferably, a human cell.

For example, the subject methods and compositions may be used to treat a disorder, a disease, or medical condition in a subject. Towards this end, the one or more genes of interest to be integrated into a cellular genome may include a gene that encodes for a therapeutic agent. By a "therapeutic agent" is meant an agent, e.g. siR A, shR A, miRNA, CRISPRi agents, peptide, polypeptide, suicide gene, etc., that has a therapeutic effect upon a cell or an individual, for example, that promotes a biological process to treat a medical condition, e.g. a disease or disorder. The terms "individual," "subject," "host," and "patient," are used interchangeably herein and refer to any human subject for whom diagnosis, treatment, or therapy is desired. The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

Examples of therapeutic agents that may be integrated into a cellular genome using the subject methods and compositions include, without limiting to, agents, i.e., siRNAs, shRNAs, miRNAs, CRISPRi agents, peptides, or polypeptides, which alter cellular activity.

Other examples of therapeutic agents that may be integrated using the subject methods and compositions include suicide genes, i.e., genes that promote the death of cells in which the gene is expressed. Non-limiting examples of suicide genes include genes that encode a peptide or polypeptide that is cytotoxic either alone or in the presence of a cofactor, e.g., a toxin such as abrin, ricin A, pseudomonas exotoxin, cholera toxin, diphtheria toxin, Herpes Simplex Thymidine Kinase (HSV-TK); genes that promote apoptosis in cells, e.g. Fas, caspases (e.g. inducible Caspase9) etc.; and genes that target a cell for ADCC or CDC-dependent death, e.g. CD20.

In some instances, the therapeutic agent alters the activity of the cell in which the agent is expressed. In other words, the agent has a cell-intrinsic effect. For example, the agent may be an intracellular protein, transmembrane protein or secreted protein that, when expressed in a cell, will substitute for, or "complement", a mutant protein in the cell. In other instances the intracellular protein is a site directed nuclease, e.g. Zinc Finger Nuclease (ZFN) Transcription activator-like effector nuclease (TALEN) or Clustered Regularly Interspaced Short Palindromic Repeats (CRISPR/Cas) that can modified the genome of the cell where it is expressed. In other instances, the therapeutic agent alters the activity of cells other than cells in which the agent is expressed. In other words, the agent has a cell-extrinsic effect. For example, the integrated gene of interest may encode a cytokine, chemokine, growth factor, hormone, antibody, or cell surface receptor that modulates the activity of other cells.

The subject methods and compositions may be applied to any disease, disorder, or natural cellular process that would benefit from modulating cell activity by integrating a gene of interest. For example, the subject agents and methods find use in treating genetic disorders. Any genetic disorder that results from a single gene defect may be treated by the subject compositions and methods, including, for example, neurodegenerative diseases, e.g., Parkinson's' disease, hemophilia, adenosine deaminase deficiency, sickle cell disease, X-Linked Severe Combined Immunodeficiency (SCID-XI), thalassemia, cystic fibrosis, alpha-1 anti-trypsin deficiency, diamond-blackfan anemia, Gaucher's disease, growth hormone deficiency, and the like. As another for example, the subject methods may be used to in medical conditions and diseases in which it is desirable to ectopically express a therapeutic agent, e.g. siRNA, shRNA, miRNA, CRISPRi agent, peptide, polypeptide, suicide gene, etc., to promote tissue repair, tissue regeneration, or protect against further tissue insult, e.g. to promote wound healing; promote the survival of the cell and/or neighboring cells, e.g. in degenerative disease, e.g. neurodegenerative disease, kidney disease, liver disease, etc.; prevent or treat infection, etc.

As one non-limiting example, the subject methods may be used to integrate a gene encoding a neuroprotective factor, e.g. a neurotrophin (e.g. NGF, BDNF, NT-3, NT-4, CNTF), Kifap3, Bcl-xl, Crmpl, Chkp, CALM2, Caly, NPG11, NPT1, Eeflal, Dhps, Cdl51, Morf412, CTGF, LDH-A, Atll, NPT2, Ehd3, Cox5b, Tubala, γ-actin, Rpsa, NPG3, NPG4, NPG5, NPG6, NPG7, NPG8, NPG9, NPG10, etc., into the genome of neurons, astrocytes, oligodendrocytes, or Schwann cells at a locus that is active in those particular cell types (for example, for neurons, the neurofilament (NF), neuro-specific enolase (NSE), NeuN, or Map2 locus; for astrocytes, the GFAP or S100B locus; for oligodendrocytes and Schwann cells, the GALC or MBP locus). Such methods may be used to treat nervous system conditions and to protect the CNS against nervous system conditions, e.g. neurodegenerative diseases, including, for example, e.g. Parkinson's Disease, Alzheimer's Disease, Huntington's Disease, Amyotrophic Lateral Sclerosis (ALS), Spielmeyer-Vogt-Sjogren-Batten disease (Batten Disease), Frontotemporal Dementia with Parkinsonism, Progressive Supranuclear Palsy, Pick Disease, prion diseases (e.g. Creutzfeldt-Jakob disease), Amyloidosis, glaucoma, diabetic retinopathy, age related macular degeneration (AMD), and the like); neuropsychiatric disorders (e.g. anxiety disorders (e.g. obsessive compulsive disorder), mood disorders (e.g. depression), childhood disorders (e.g. attention deficit disorder, autistic disorders), cognitive disorders (e.g. delirium, dementia), schizophrenia, substance related disorders (e.g. addiction), eating disorders, and the like); channelopathies (e.g. epilepsy, migraine, and the like); lysosomal storage disorders (e.g. Tay-Sachs disease, Gaucher disease, Fabry disease, Pompe disease, Niemann-Pick disease, Mucopolysaccharidosis (MPS) & related diseases, and the like); autoimmune diseases of the CNS (e.g. Multiple Sclerosis, encephalomyelitis, paraneoplastic syndromes (e.g. cerebellar degeneration), autoimmune inner ear disease, opsoclonus myoclonus syndrome, and the like); cerebral infarction, stroke, traumatic brain injury, and spinal cord injury.

In certain embodiments, the subject methods find use in treating muscular dystrophy, such as, Duchenne muscular dystrophy, limb girdle muscular dystrophy 2B, and limb girdle muscular dystrophy 2D. When used to treat Duchenne muscular dystrophy in a subject, the polynucleotide sequence inserted into the genome of the human cell may include a polynucleotide encoding dystrophin, such as, full length dystrophin or functional fragments or a functional variant thereof. In certain cases, a subject having limb girdle muscular dystrophy 2B may be treated using the subject methods, where the polynucleotide sequence inserted into the genome of the human cell may encode for dysferlin or a functional fragment or a functional variant thereof. In certain cases, a subject having limb girdle muscular dystrophy 2D may be treated using the subject methods, where the polynucleotide sequence inserted into the genome of the human cell may encode alpha-sarcoglycan or a functional fragment or a functional variant thereof. In certain cases, the human cell may be an iPS cell derived from a cell of the subject being treated.

Other examples of how the subject methods may be used to treat medical conditions are disclosed elsewhere herein, or would be readily apparent to the ordinarily skilled artisan.

As discussed above, any gene of interest may be integrated into a target locus, for example, any gene encoding a siR A, shR A, miRNA, CRISPRi element, peptide, or polypeptide may be integrated. Additionally, as discussed above, more than one gene of interest may be integrated, for example, two or more genes of interest may be integrated, three or more genes may be integrated, four or more genes may be integrated, e.g. five or more genes may be integrated. Thus, for example, in embodiments where the genetically modified cell is a ES or PS or iPS cell, the one or more polynucleotide sequences/genes of interest may be transcription factors that promote the differentiation of the ES or PS or iPS cell into a particular cell lineage. For example, the subject methods may be used to convert iPS generated from a somatic cell isolated from a subject in need of a particular cell type into the particular cell type. Since the cells to be transplanted into the subject are derived from the subject's cells, any immune response to the transplanted cells may be reduced or avoided.

Integrating one or more genes of interest into genomic DNA such that it is expressed in cell finds use in many fields, including, for example, gene therapy, and research. For example, such modifications are therapeutically useful, e.g. to treat a genetic disorder by complementing a genetic mutation in a subject with a wild-type copy of the gene; to promote naturally occurring processes, by promoting/augmenting cellular activities (e.g. promoting wound healing for the treatment of chronic wounds or prevention of acute wound or flap failure, by augmenting cellular activities associated with wound healing); to modulate cellular response (e.g. to treat diabetes mellitus, by providing insulin); to express antiviral, antipathogenic, or anticancer therapeutics in subjects, e.g. in specific cell populations or under specific conditions, etc. Other uses for such genetic modifications include in the induction of induced pluripotent stem cells (iPSCs), e.g. to produce iPSCs from an individual for diagnostic, therapeutic, or research purposes; in the production of genetically modified cells, for example in manufacturing for the large scale production of proteins by cells for therapeutic, diagnostic, or research purposes.

The genetically modified cells of the present disclosure may be provided to the human subject alone or with a suitable substrate or matrix, e.g., to support their growth and/or organization in the tissue to which they are being transplanted, in a therapeutically effective amount. As use herein, the term "therapeutically effective amount" refers to the amount of the cells of the invention sufficient to achieve the intended purpose, such as, in this case, to support the growth and/or organization of the tissue which the cell are being transplanted. The amount of cells needed for this purpose can be easily calculated by the skilled person in the art. Usually, at least $1 \times 10^3$ cells may be administered, for example $5 \times 10^3$ cells, $1 \times 10^4$ cells, $5 \times 10^4$ cells, $1 \times 10^5$ cells, $1 \times 10^6$ cells or more, to a subject. The cells may be introduced to the subject via any of the following routes: parenteral, subcutaneous, intravenous, intracranial, intraspinal, intraocular, intramuscular, or into spinal fluid. The cells may be introduced by injection, catheter, or the like. Examples of methods for local delivery, that is, delivery to the site of injury, include, e.g. through an Ommaya reservoir, e.g. for intrathecal delivery; by bolus injection, e.g. by a syringe, e.g. into a joint; by continuous infusion, e.g. by cannulation, e.g. with convection; or by implanting a device upon which the cells have been reversibly affixed.

The number of administrations of treatment to a subject may vary. Introducing the genetically modified cells into the subject may be a one-time event; but in certain situations, such treatment may elicit improvement for a limited period of time and require an on-going series of repeated treatments. In other situations, multiple administrations of the genetically modified cells may be required before an effect is observed. The exact protocols depend upon the disease or condition, the stage of the disease and parameters of the individual subject being treated.

The method herein described provides improvements in cell line engineering for applications in therapy, diagnostics and biotechnology. A multi-copy system could be very useful in these contexts if multiple integration sites are required in order to maintain independent expression from different parts of a synthetic gene circuit. For example, in a situation where the way in which multiple transcriptional units interact with each other is not known. In this case, it would be possible to sequentially integrate different units modifying also their order. This docking platform could also be used to generate disease models for drug screening and disease pathophysiology both in animal and human pluripotent cells. A docking platform with multi-copy docking sites could be used to generate models of cancer metabolism and anti-cancer treatment by the integration of cancer genes into the docking followed by the incorporation of synthetic lethal genes into other docking site.

The system could, as well, be adapted to yeast for the production of biofuels and bio-based chemicals by engineering metabolic pathways in the multi-copy integration platform. Target bio-bases chemicals obtained through the metabolic engineering of *Saccharomyces cerevisiae* are primarily derived from pyruvate, but this production generates by-products that limit its efficiency. In order to improve the glucose consumption rate and reduce the amount of by-products, the methods of the invention could be employed to co-overexpress enzymes involved in the rate limiting step of yeast glycolysis. Cell lines with different number of recombinant sites (also called "docking sites") could as well be useful to study the optimal gene copy number for protein expression. Different cell lines may have alternative tolerances for the number of copies of a given gene. In the same way, any given cell line would very likely have different tolerance for different proteins. This is already well established in yeast where, for example, it has been demonstrated that 12 copies is the optimal number for secretory expression of porcine insulin precursor (PIP) in *P. pastoris*.

Kits of the Invention

Also provided are kits for practicing one or more of the above-described methods. The subject kits may have a combination of nucleic acid compositions as described herein, or recipient cells as described herein, or both. Reagents of interest may include polynucleotide compositions, e.g. a vector comprising CCR5 locus specific left homology arm, phiC31 second recombination site, a reporter gene or a selection marker or both, BxbI recombination site, CCR5 locus specific right homology arm; a vector comprising phiC31 first recombination site, a cloning site that includes restriction enzyme sites for cloning of a polynucleotide sequence of interest; a nucleic acid encoding phiC31, a nucleic acid encoding Bxb1. Other non-limiting examples of reagents include targeted nuclease compositions, e.g. a target nuclease or pair of targeted nucleases specific for the target site in the CCR5 locus; reagents for selecting cells genetically modified with the integrated gene of interest; and positive and negative control vectors or cells comprising integrated positive and/or negative control sequences for use in assessing the efficacy donor polynucleotide compositions in cells, etc.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Unless otherwise defined, all technical and scientific terms used herein have the same meaning as commonly understood by one of ordinary skill in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples, drawings and sequence listing are provided by way of illustration and are not intended to be limiting of the present invention.

phiC31-specific attP sites. Half dark/light grey rectangle: phiC31-specific attR sites. Light grey triangles: SB-specific ITR elements. Dark grey triangles: PB-specific ITR elements. White circle: phiC31-specific attP, attB and attR sites. Triangle near to white circle: transposon-specific ITR elements.

Figure 7:
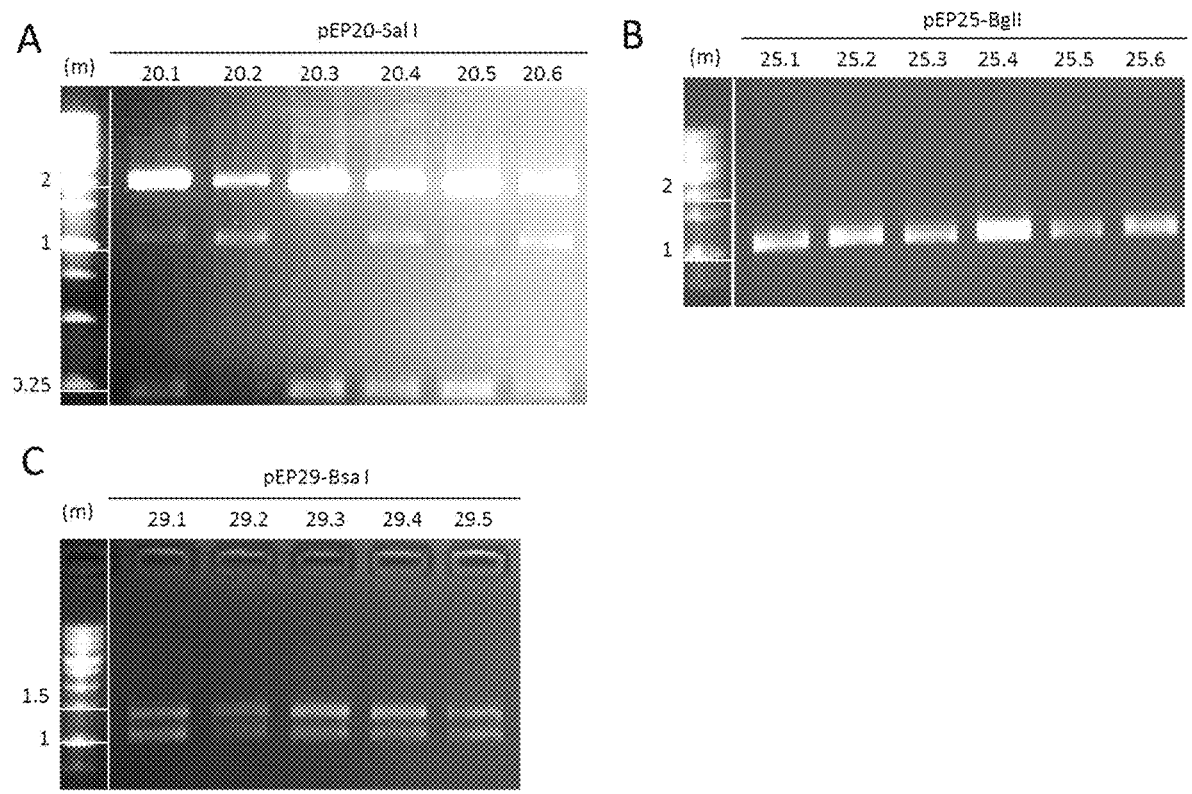

FIG. 7. Restriction fragment analysis of pEP20, pEP25 and pEP29. Agarose gel (0.8%) electrophoresis with ethidium bromide staining. (A) SalI digestion of pEP20. Expected bands: 209 and 1853 bp. (B) BglII digestion of pEP25. Expected bands: 1044 and1135 bp. (C) BsaI digestion of pEP29. Expected bands: 989 and 1131 bp. Molecular size marker, m=1 kb DNA ladder.

Figure 8:
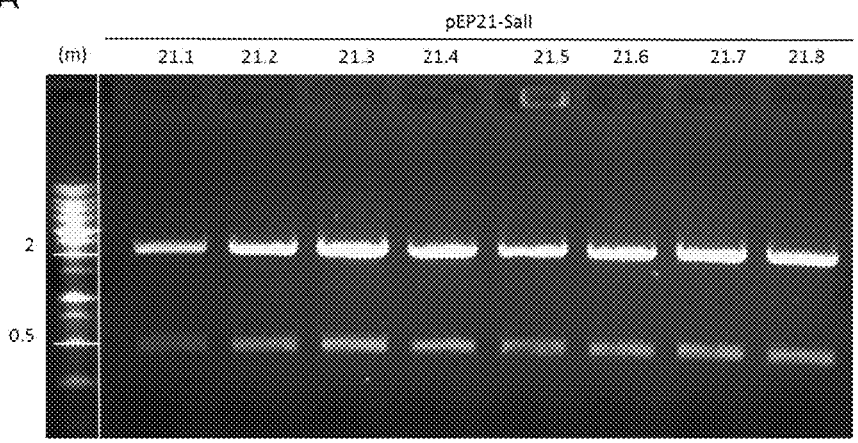
Figure 8:
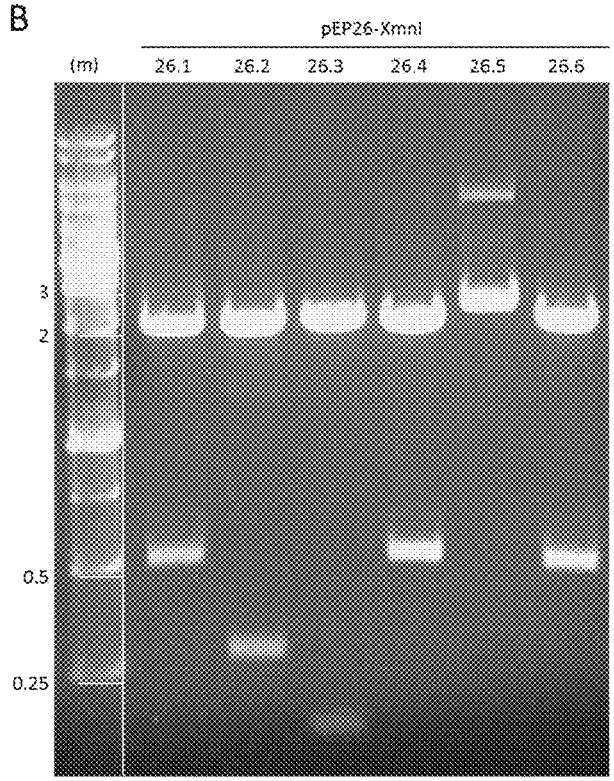
Figure 8:
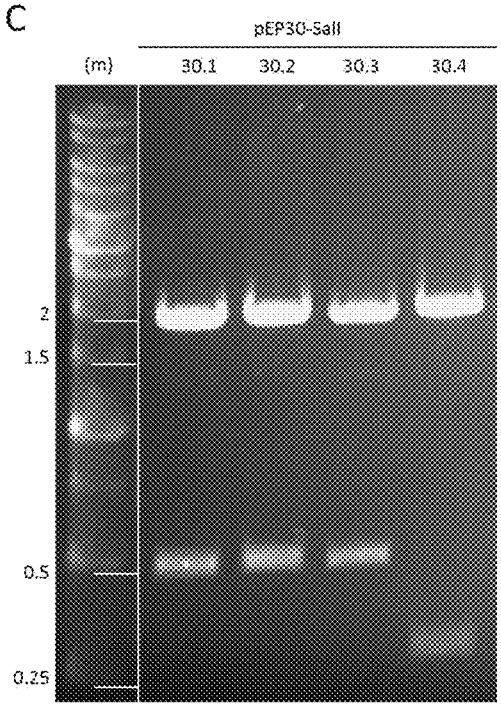

FIG. 8. Restriction fragment analysis of pEP21, pEP26 and PEP30. Agarose gel (0.8%) electrophoresis with ethidium bromide staining. (A) SalI digestion of pEP21. Expected bands: 435 and 1853 bp. (B) XmnI digestion of pEP26. Expected bands: 509 and 1910 bp. (C) SalI digestion of pEP30. Expected bands: 493 and 1853 bp. Molecular size marker, m=1 kb DNA ladder.

Figure 9:
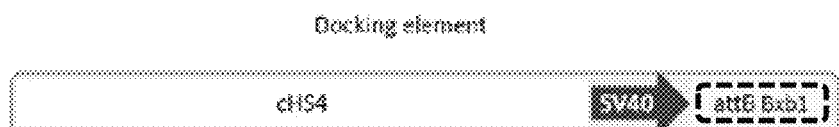
Figure 9:
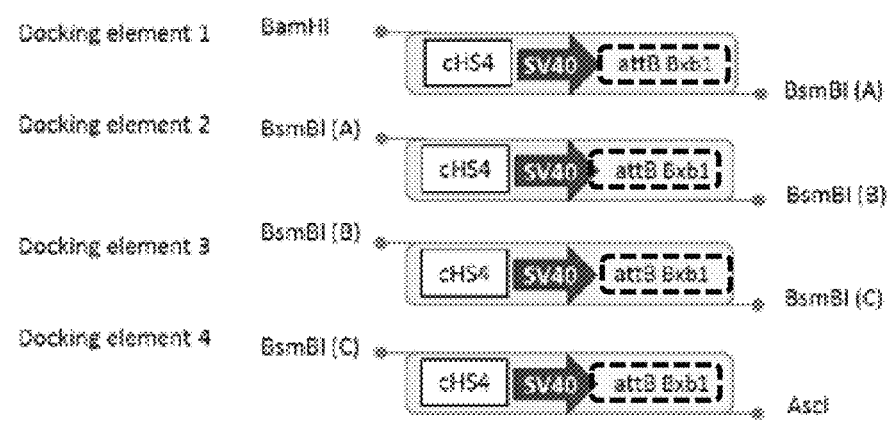
Figure 9:
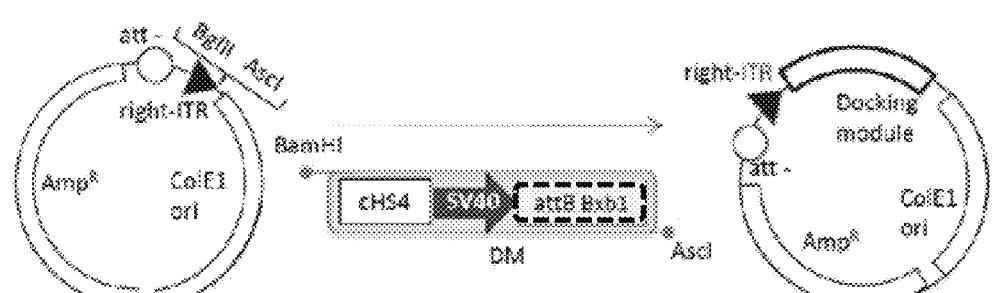

FIG. 9. Docking module assembly. (A) Each Docking element consists of one cHS4 insulator, the SV40 promoter and a Bxb1-specific attB site. (B) PCR amplification of the docking element with four different sets of primers containing specific Type IIS restriction endonuclease sites at their overhangs. (C) Four docking elements assembled into a single docking module (DM) were cloned into pEP21, pEP26 and pEP30. The resulting plasmids, pEP22, pEP27 and pEP31 contain a phiC31 attachment site, a transposon right-ITR element and docking module. White rectangle: cHS4 insulator. Arrow: SV40 promoter. Discontinue line Rectangle: Bxb1-specific attB site. White circle: phiC31-specific attP, attB and attR sites. Triangle: transposon-specific ITR elements. Bold curved rectangle: docking module.

Figure 10:
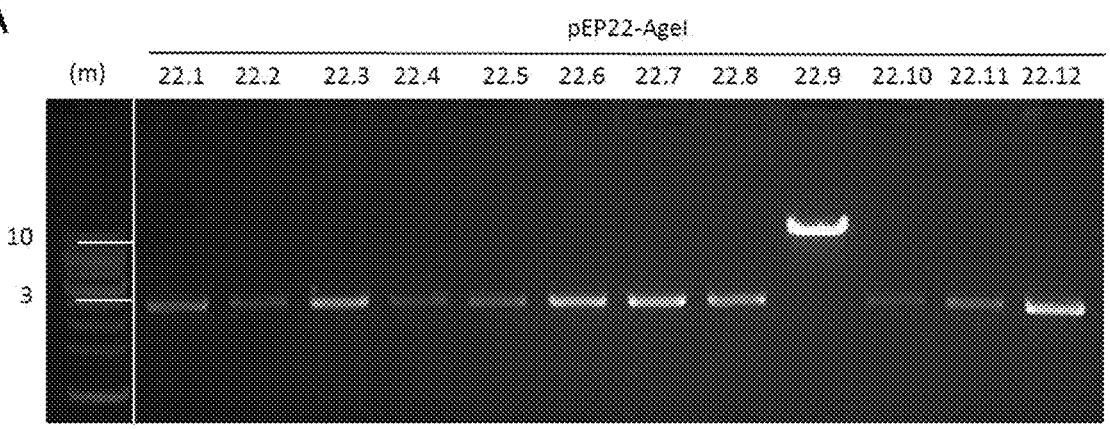
Figure 10:
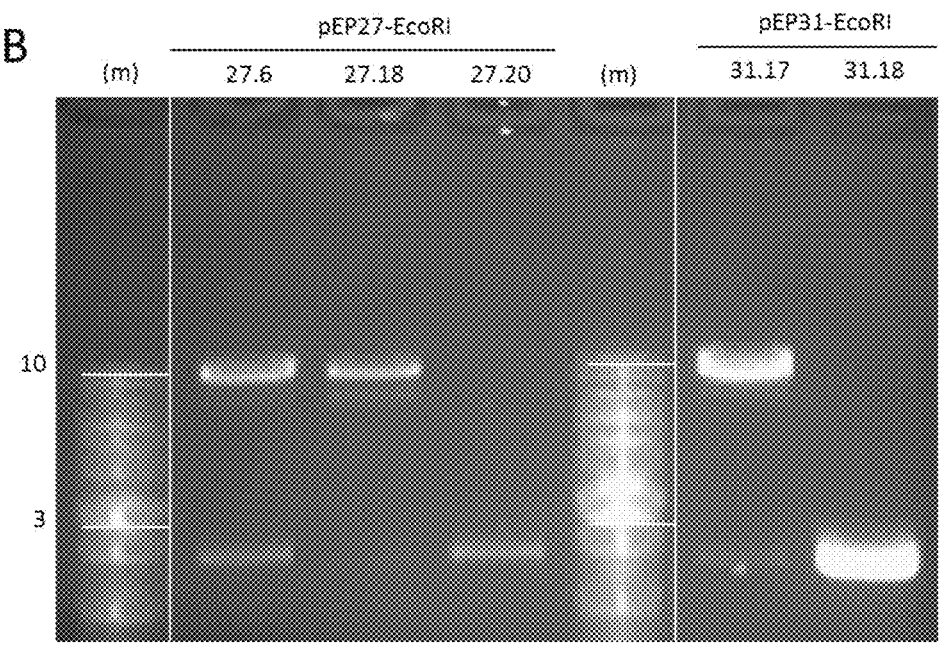

FIG. 10. Restriction fragment analysis of pEP22, pEP27 and pEP31. Agarose gel (0.8%) electrophoresis with ethidium bromide staining. (A) AgeI digestion of pEP22. Expected band: 9047 bp. (B) EcoRI digestion of pEP27 and pEP31. Expected bands 9178 and 9105 bp, respectively. Molecular size marker, m=1 kb DNA ladder.

Figure 11:
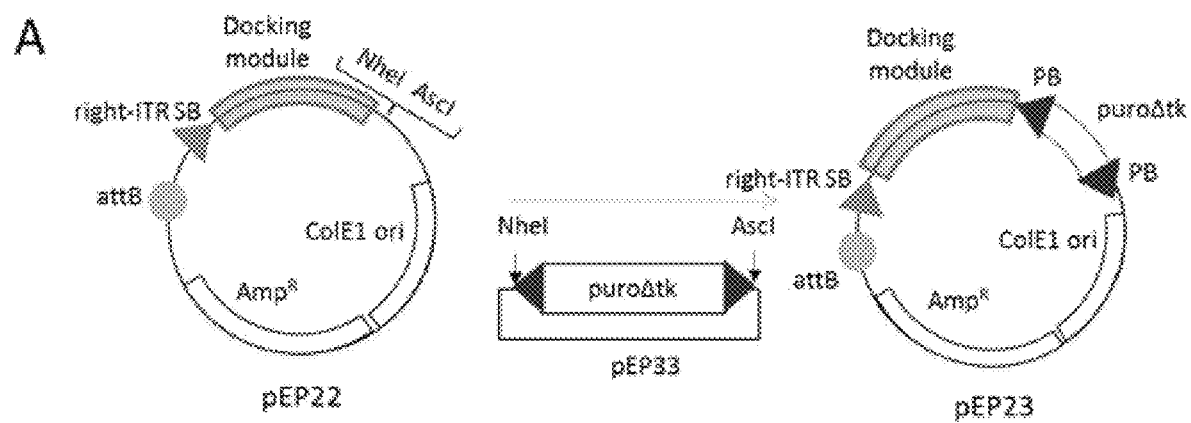
Figure 11:
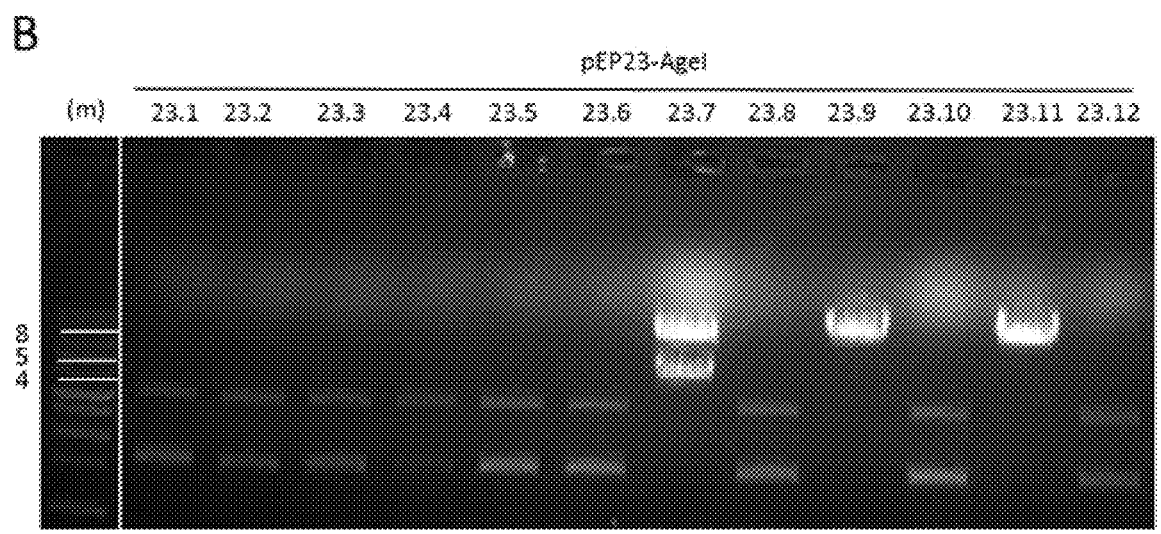

FIG. 11. Construction of vector pEP23. (A) Diagram of the cloning of the selection marker (puroΔtk), flanked by PB ITR elements, into pEP22. (B) AgeI digestion of pEP23. Expected bands: 4563 and 7603 bp. Agarose gel (0.8%) electrophoresis with ethidium bromide staining. Molecular size marker, m=1 kb DNA ladder. Grey circle: phiC31-specific attB sites. Light grey triangles: SB-specific ITR elements. Dark grey triangles: PB-specific ITR elements. Grey curved rectangle: docking module.

Figure 12:
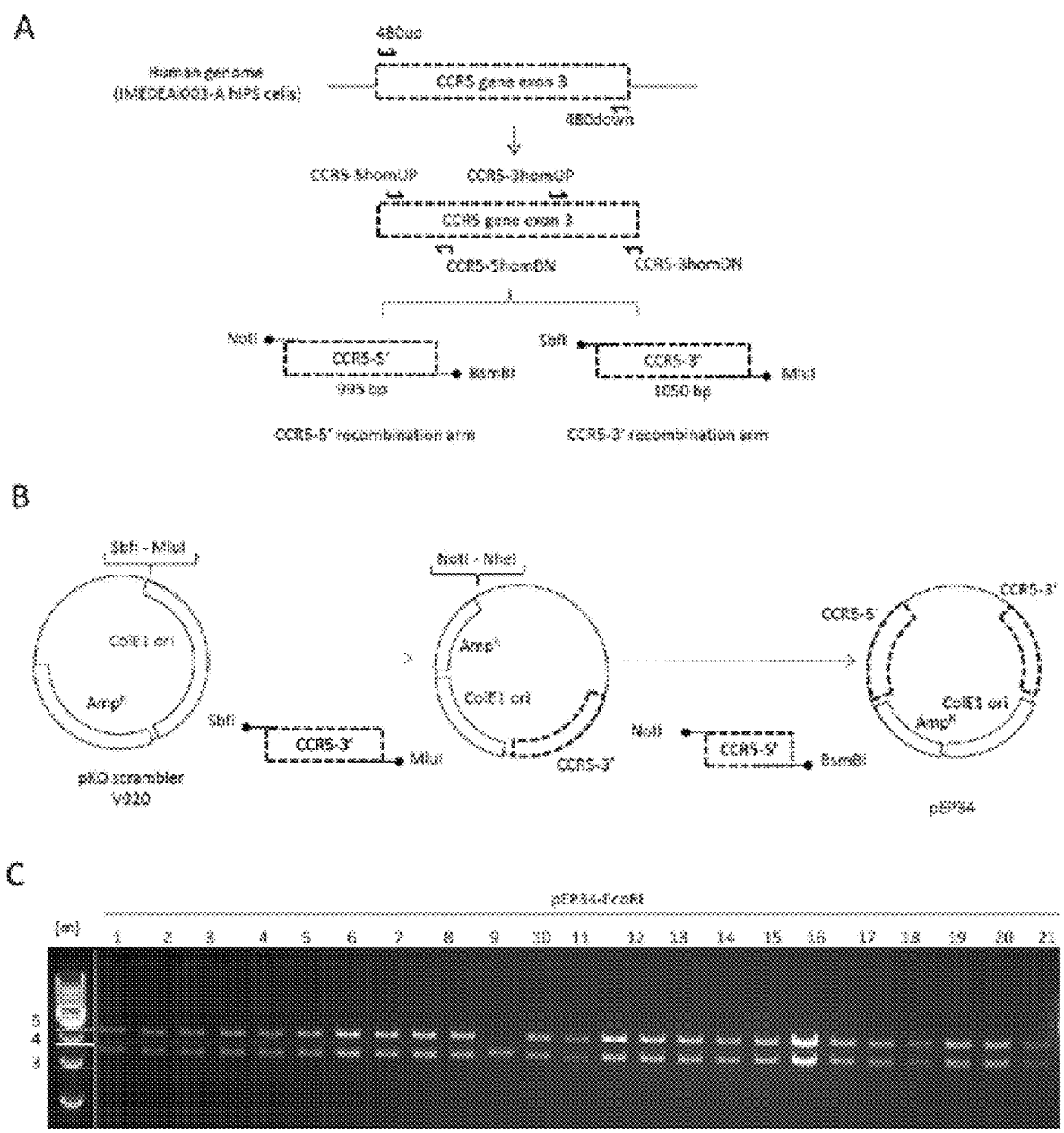

FIG. 12. Construction of vector pEP34. (A) Amplified exon 3 region of CCR5 gene using the 480up/down primers served as template for the generation of 5' and 3' recombination arm by a second PCR amplification. (B) Synthesis of pEP34 by cloning the CCR5-5' and CCR5-3' recombination arms into the plasmid pKOscramblerV920. (C) EcoRI digestion of pEP34. Expected bands: 3652 and 4832 bp. Agarose gel (0.8%) electrophoresis with ethidium bromide staining. Molecular size marker, m=1 kb DNA ladder.

Figure 13:
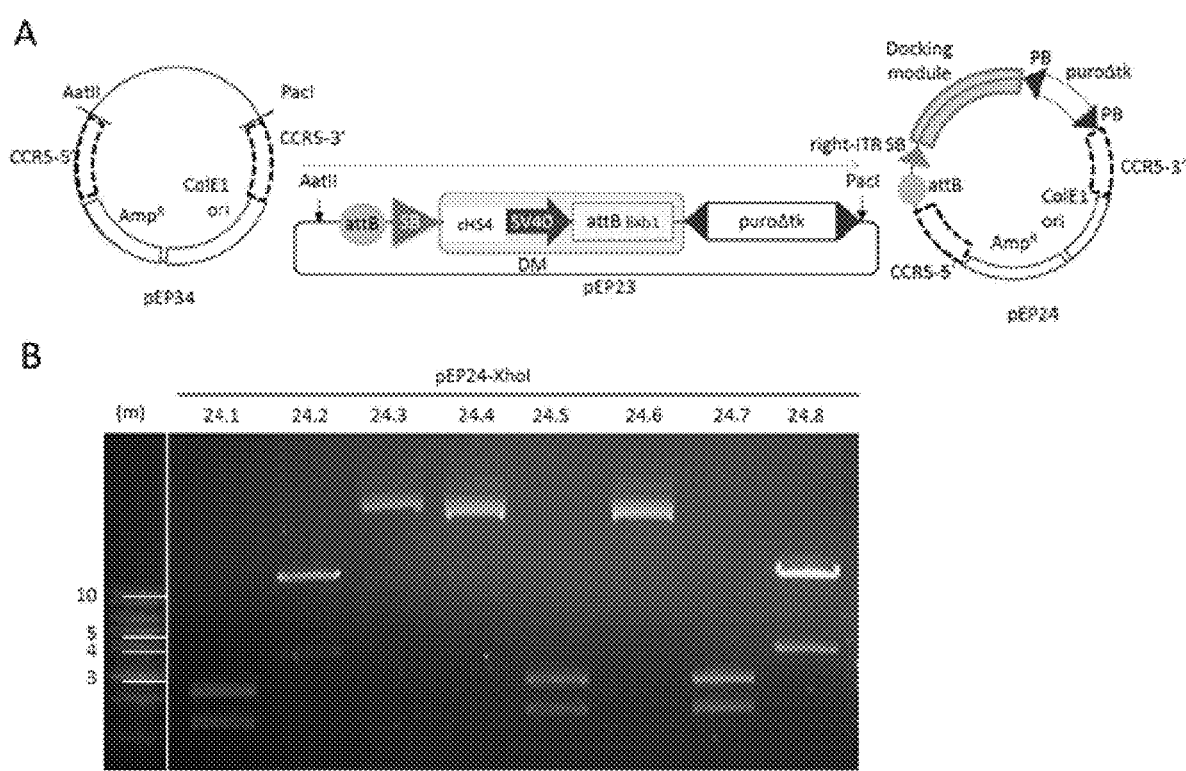

FIG. 13. Final step in the construction of the recombination vector pEP24. (A) Diagram of the cloning of phiC31-specific attB site, the right-ITR element of SB, a docking module consisting of cHS4 insulator, the SV40 promoter and a Bxb1-specific attB site, as well as a puroΔtk selection marker flanked by ITR elements of PB from pEP23 into pEP34 harboring the two CCR5 recombination arms. (B) XhoI digestion of pEP24. Expected bands: 3313 and 10897 bp. Agarose gel (0.8%) electrophoresis with ethidium bromide staining. Molecular size marker, m=1 kb DNA ladder. Light grey Circles: phiC31-specific attB sites. Light Grey triangles: SB-specific ITR elements. Dark grey triangles: PB-specific ITR elements. Grey curved rectangle: docking module (DM). White rectangle: cHS4 insulator. Arrow: SV40 promoter. Rectangle after arrow: Bxb1-specific attB site.

Figure 14:
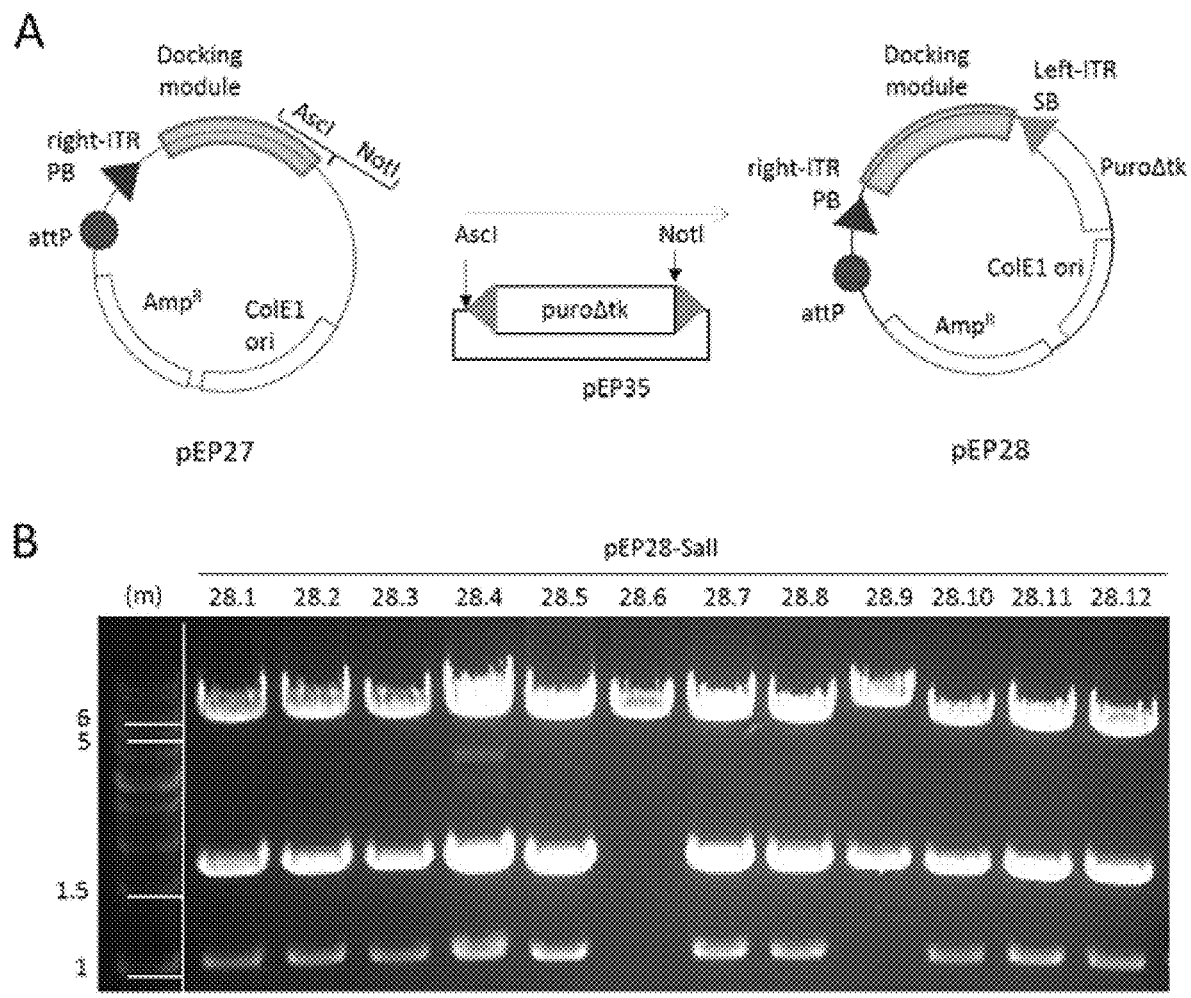

FIG. 14. Final step in the construction of the recombination vector pEP28. (A) Diagram of the cloning of puroΔtk and the left-ITR element of SB into pEP27. (B) SalI digestion of pEP28 with expected bands: 991, triple band of 1693 and 6777 bp. Agarose gel (0.8%) electrophoresis with ethidium bromide staining. Molecular size marker, m=1 kb DNA ladder. Dark grey circles: phiC31-specific attP sites. Light grey triangle: SB-specific ITR elements. Dark grey triangles: PB-specific ITR elements. Grey curved rectangle: docking module.

Figure 15:
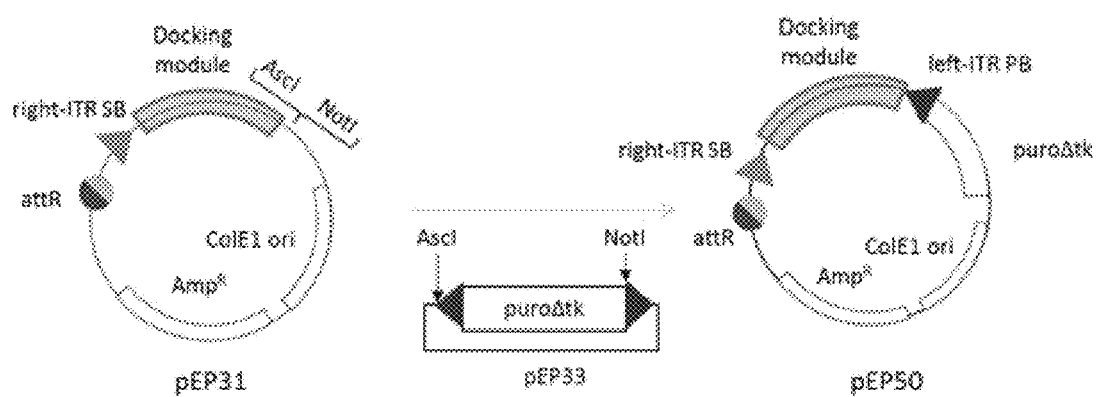
Figure 15:
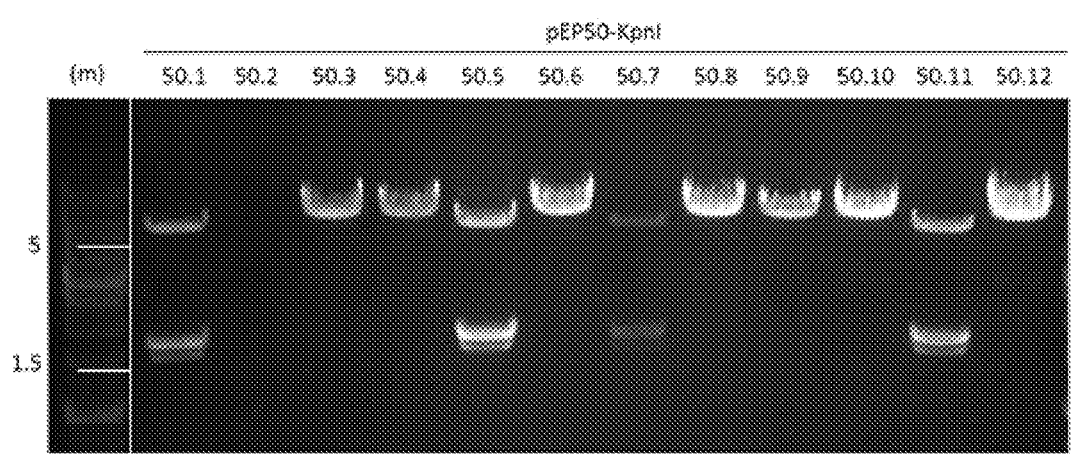

FIG. 15. Generation of the third docking vector, pEP50. (A) Diagram of the cloning of puroΔtk with the left-ITR element of PB into pEP31. pEP50 consists of the phiC31-specific attR site, the right-ITR element of SB, a docking module and (puroΔtk) with left-ITR element of PB. (B) KpnI digestion of pEP50. Expected bands: 1515, triple band of 1693 and 5276 bp. Agarose gel (0.8%) electrophoresis with ethidium bromide staining. Molecular size marker, m=1 kb DNA ladder. Half Dark/light grey circles: phiC31-specific attR sites. Light grey triangles: SB-specific ITR elements. Dark grey triangles: PB-specific ITR elements. Grey curved rectangle: docking module.

Figure 16:
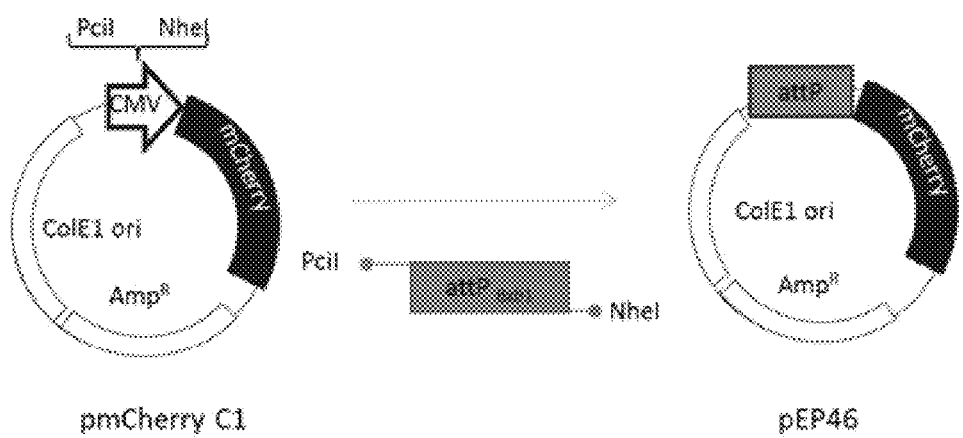
Figure 16:
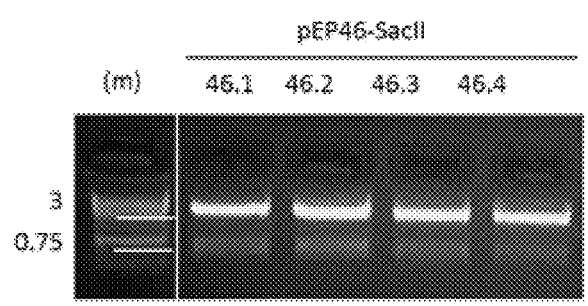

FIG. 16. Generation of the testing vector pEP46. (A) Diagram of the removal of the CMV promoter and the insertion of one Bxb1-specific attP site 5' of the mCherry cDNA. (B) Agarose gel (0.8%) electrophoresis with ethidium bromide staining. SacII digestion. Expected bands: 816 and 3324 bp. Molecular size marker, m=1 kb DNA ladder. Black curved rectangle: mCherry fluorescence. Dark grey rectangle: Bxb1-specific attP sites.

Figure 17:
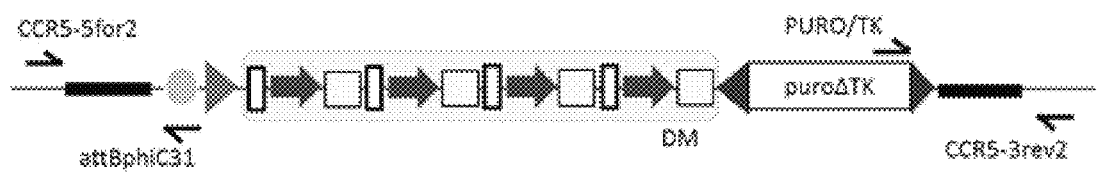
Figure 17:
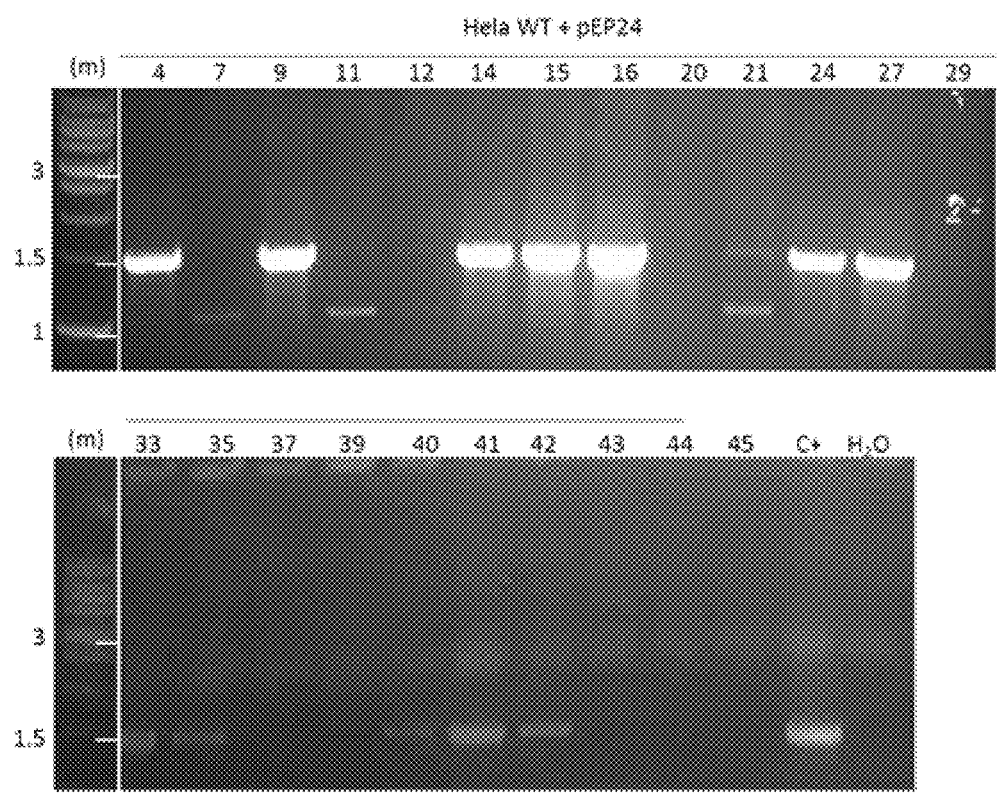
Figure 17:
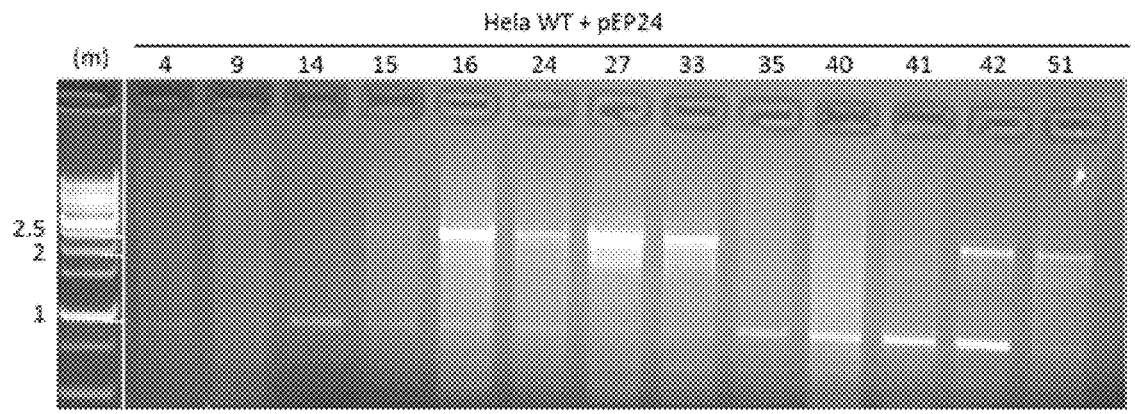

FIG. 17. Example of screening by PCR of the clones obtained by recombination at step 1. (A) Diagram of the PCR characterization. (B) 5' PCR analysis using CCR5-5 for2 and attBphiC31 primers (1500 bp amplicon). Positive and negative controls (water) are shown at the right end of photo. (C) 3' PCR analysis using PURO/TK and CCR5-3rev2 primers (2500 bp). Agarose gel (0.8%) electrophoresis with ethidium bromide staining. Molecular size marker, m=1 kb DNA ladder. Bold lines: CCR5 recombination arms; Light grey circle: phiC31-specific attB sites; Light grey triangle: SB-specific ITR elements; Dark grey triangles: PB-specific ITR elements; Docking module (DM): white rectangles: cHS4 insulator, arrows: SV40 promoters, squares: Bxb1-specific attB sites.

Figure 18:
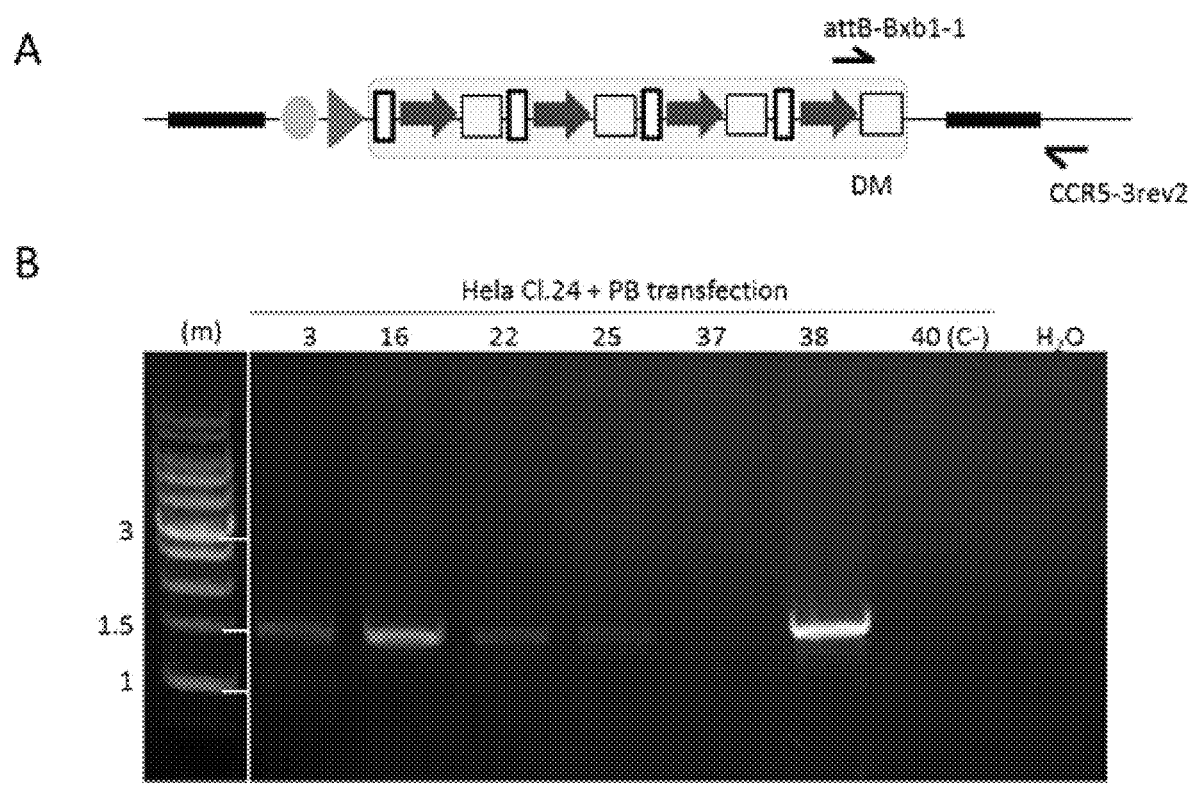

FIG. 18. Excision of the selection cassette by PB transposase in HeLa CI.24. (A) Diagram of the PCR characterization. (B). Example of 7 clones analyzed by PCR using the primers attB-Bxb1-1/CCR5-3rev2 (1500 bp), CI.24.40 and CI.24.37 were negative. Agarose gel (0.8%) electrophoresis with ethidium bromide staining. Molecular size marker, m=1 kb DNA ladder. Bold lines: CCR5 recombination arms; Light grey circle: phiC31-specific attB sites; Light grey triangle: SB-specific ITR elements; Docking module (DM): white rectangles: cHS4 insulator, arrows: SV40 promoters, squares: Bxb1-specific attB sites.

Figure 19:
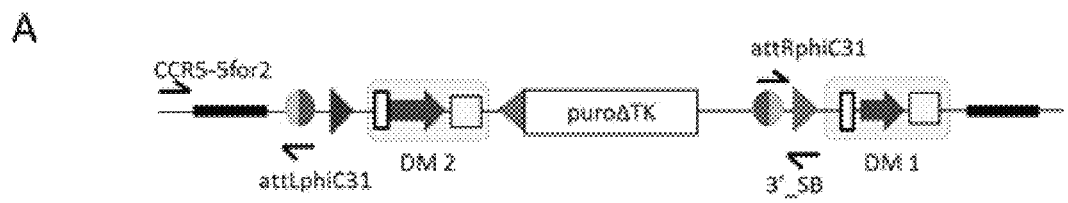
Figure 19:
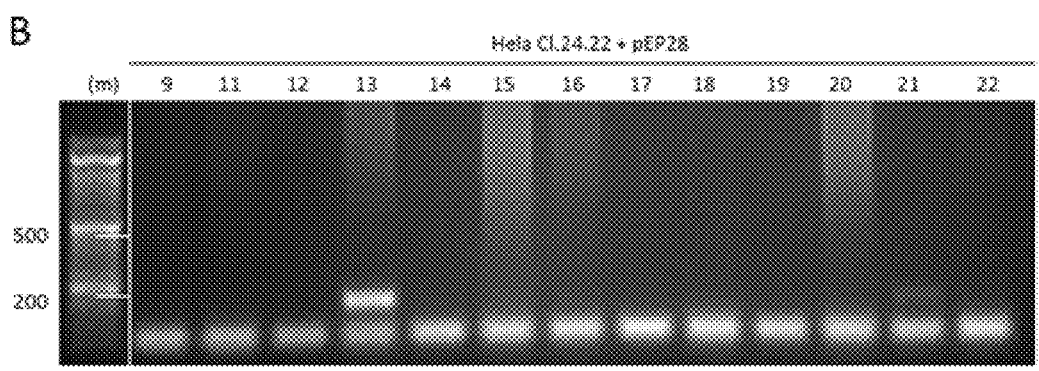
Figure 19:
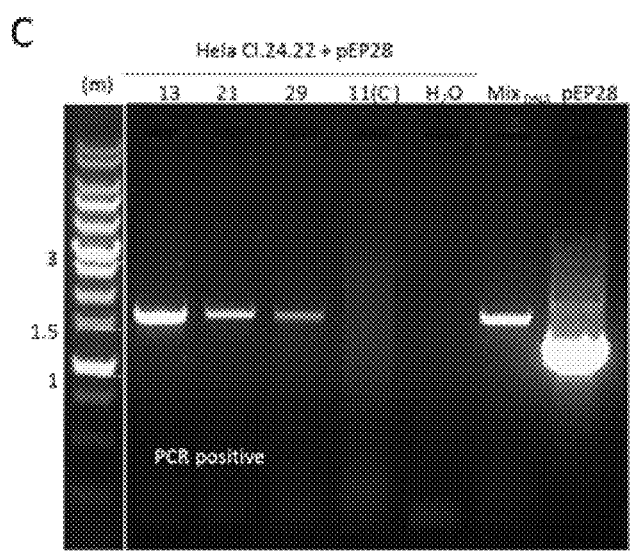
Figure 19:
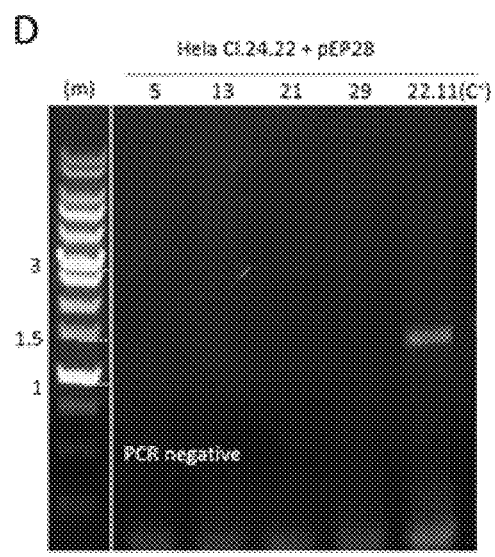

FIG. 19. Example of screening by PCR of the clones obtained by recombination at step 2. (A) Diagram of PCR characterization. (B) PCR analysis of the 3' recombination arm using attRphiC31/3'_SB primers (amplicon: 173 pb).

Molecular size marker, m=50 bp DNA ladder. (C) PCR analysis of the 5'recombination arm using CCR5-5 for2/attLphiC31 primers (amplicon: 1538 bp). (D) PCR analysis using CCR5-5 for2/attBphiC31 primers to confirm the disappearance of the 1,538 bp amplicon previously detected in step 1 of platform assembly. Agarose gel (2%) electrophoresis with ethidium bromide staining. Molecular size marker, m=1 kb DNA ladder. Bold lines: CCR5 recombination arms; Half light/dark grey circle: phiC31-specific attL sites; Dark grey triangle: PB-specific ITR elements; Docking module 2 (DM2): white rectangle: cHS4 insulator, arrow: SV40 promoters, square: Bxb1-specific attB sites; Light grey triangles: SB-specific ITR elements; Half Dark/light grey circle: phiC31-specific attR sites; Docking module 1 (DM1): white rectangle: cHS4 insulator, arrow: SV40 promoters, square: Bxb1-specific attB sites.

Figure 20:
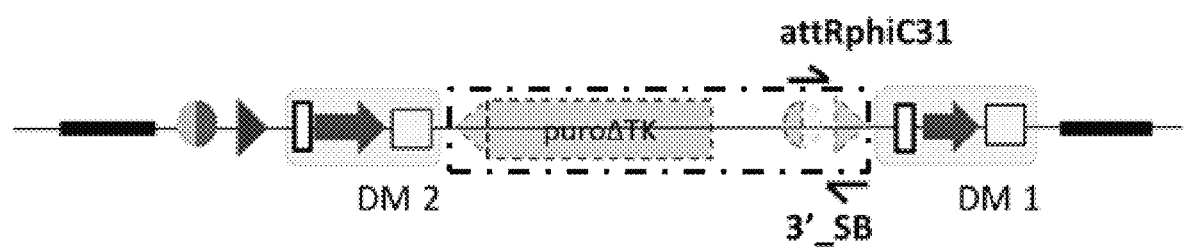
Figure 20:
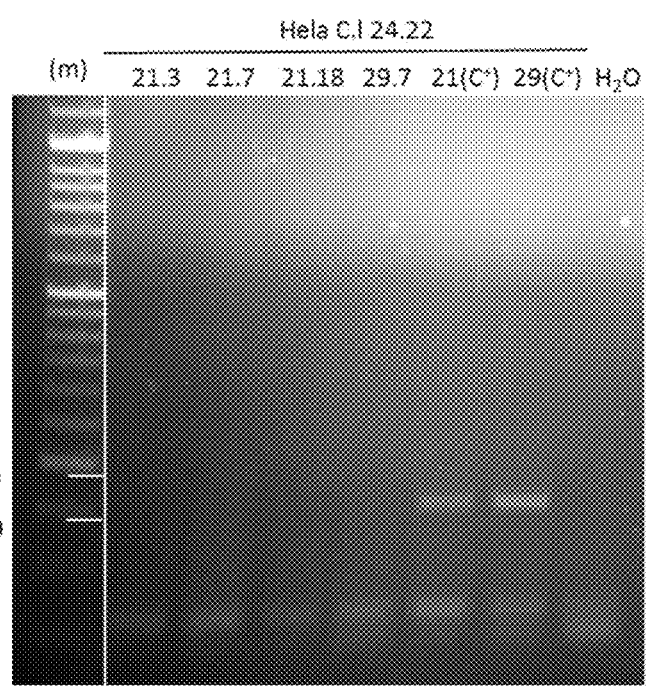

FIG. 20. Excision of the selection cassette by SB transposase in HeLa CI.24.22.21 and CI.24.22.29 clones. (A) Diagram of PCR characterization. (B) Agarose gel (2%) electrophoresis with ethidium bromide staining. PCR analysis using attRphiC31/3'_SB primers (173 bp) demonstrated the loss of PCR product after SE excision. As positive control, DNA from HeLa CI.24.22.21 (21C+) and HeLa CI.24.22.29 (29 C+) without transfection were used. Molecular size marker, m=50 bp DNA ladder. Bold lines: CCR5 recombination arms; Half light/dark grey circle: phiC31-specific attL sites; Dark grey triangle: PB-specific ITR elements; Docking module 2 (DM2): white rectangle: cHS4 insulator, arrow: SV40 promoters, square: Bxb1-specific attB sites; Light grey triangles: SB-specific ITR elements; Half Dark/light grey circle: phiC31-specific attR sites; Docking module 1 (DM1): white rectangle: cHS4 insulator, arrow: SV40 promoters, square: Bxb1-specific attB sites. The elements within the discontinue line rectangle are missing.

Figure 21:
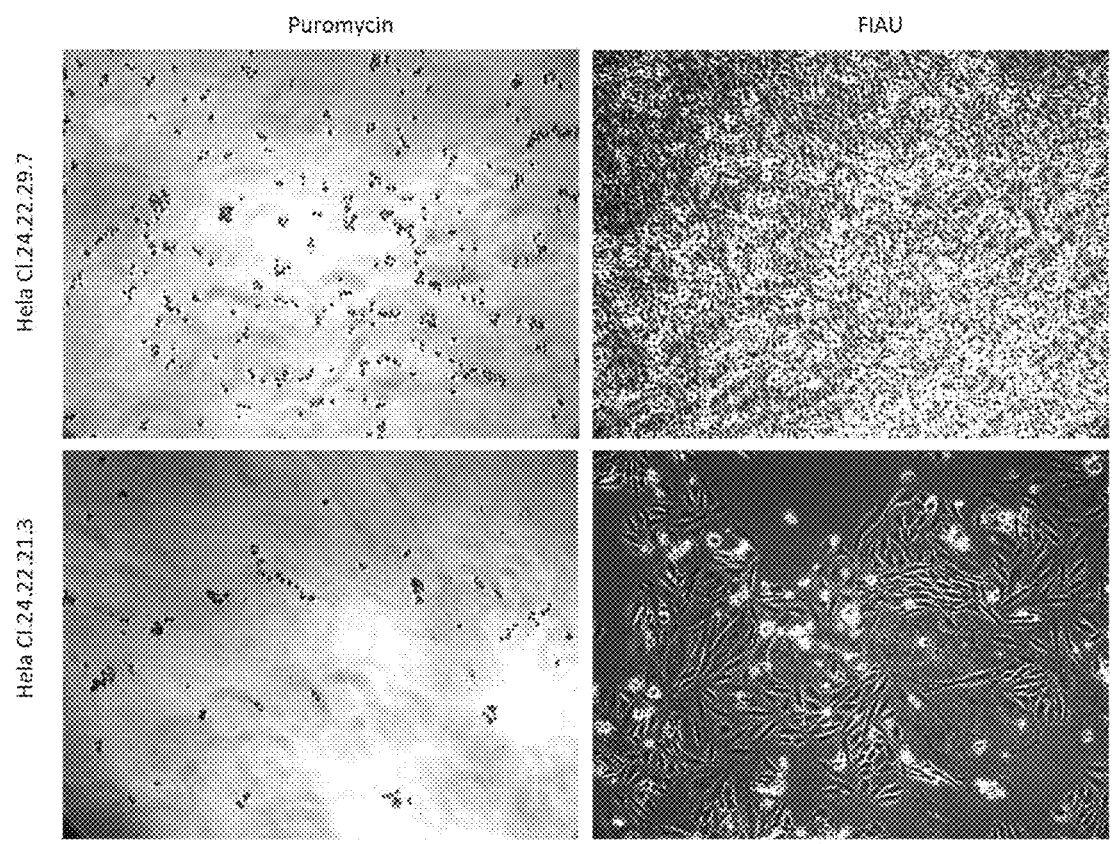

FIG. 21. Drug sensibility of HeLa CI.24.22.21.3 and CI.24.22.29.7 cells. HeLa CI24.22.21.3 and CI24.22.29.7 were exposed to puromycin [2 µg/ml] and FIAU [1 µM] selection during 6 days to demonstrate the excision of selection elements.

Figure 22:
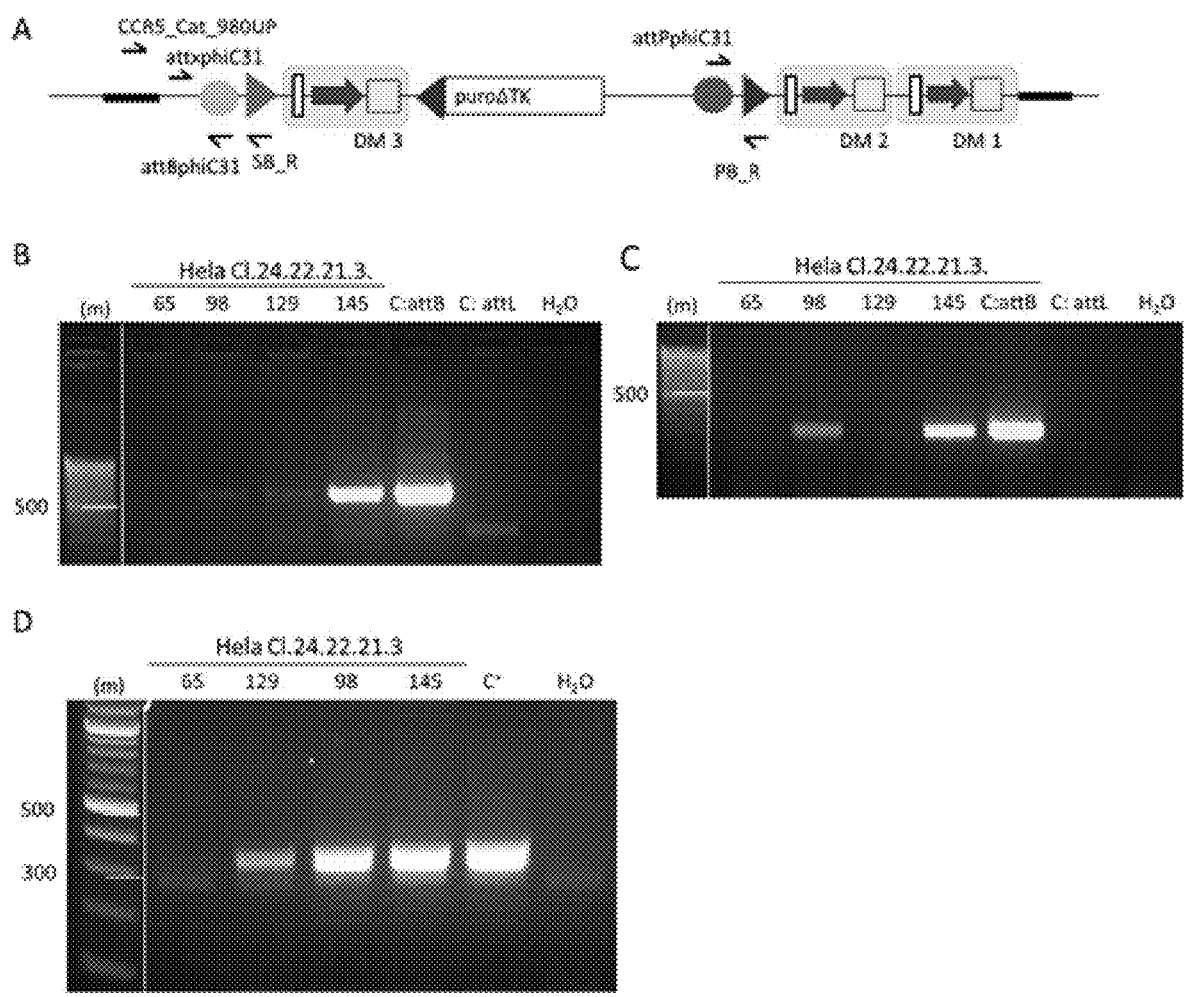

FIG. 22. PCR screening of the clones obtained by recombination at step 3. (A) Diagram of the PCR characterization. (B) phiC31-specific attB PCR screening with CCR5_Cat_980UP/attBphiC31 primers (amplicon: 581 bp). (C) Right-SB-ITR PCR screening with attxphiC31/SB_R (amplicon: 296 bp). (D) phiC31-specific attR screening with attPphiC31/PB_R primers (amplicon: 343 bp). Agarose gel (2%) electrophoresis with ethidium bromide staining. Molecular size marker, m=50 bp DNA ladder. Bold lines: CCR5 recombination arms; Light grey circle: phiC31-specific attB sites; Light grey triangle: SB-specific ITR elements; Docking module 3 (DM3): white rectangle: cHS4 insulator, arrow: SV40 promoters, square: Bxb1-specific attB sites; Dark grey triangles: PB-specific ITR elements; Dark grey circle: phiC31-specific attP sites; Docking module 2 (DM2); Docking module 1 (DM1).

Figure 23:
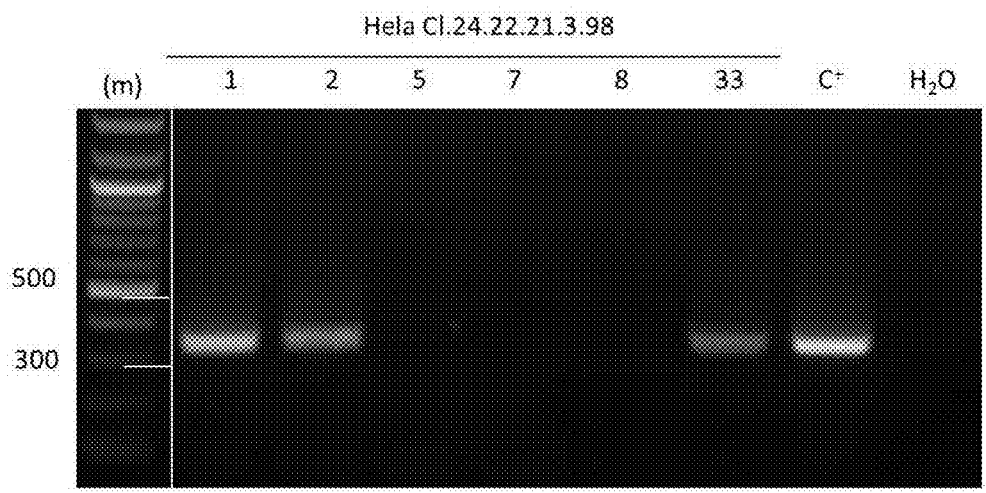

FIG. 23. Excision of the selection cassette by PB transposase in HeLa CI. 24.22.21.3.98. Agarose gel (2%) electrophoresis with ethidium bromide staining. PCR analysis using attPphiC31/PB_R primers (amplicon: 343 bp) demonstrated the loss of PCR product after SE excision. As positive control, DNA from HeLa CI.24.22.21.3.145 (C+) without transfection. Molecular size marker, m=50 bp DNA ladder.

Figure 24:
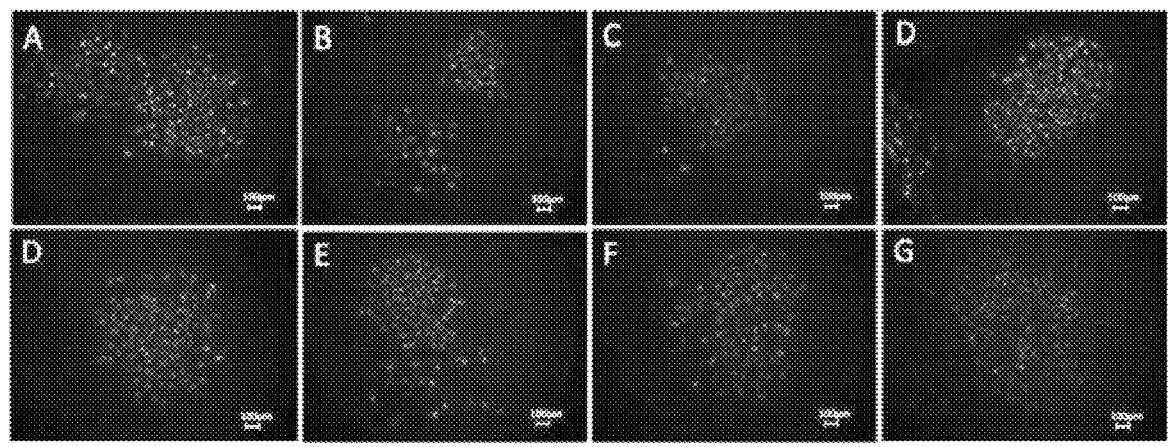

FIG. 24. Determination of mCherry fluorescence by epifluorescence microscopy after pEP46 loading in HeLa CI.24.22 cells. Fluorescence intensity was measured after 10 days of transfection by epifluorescence microscopy using the red channel and constant exposition. Scale bar=100 µm. (A) Clone 1, (B) Clone 2, (C) Clone 3, (D) Clone 4, (E) Clone 5, (F) Clone 6, (G) Clone 7, (H) Clone 8.

Figure 25:
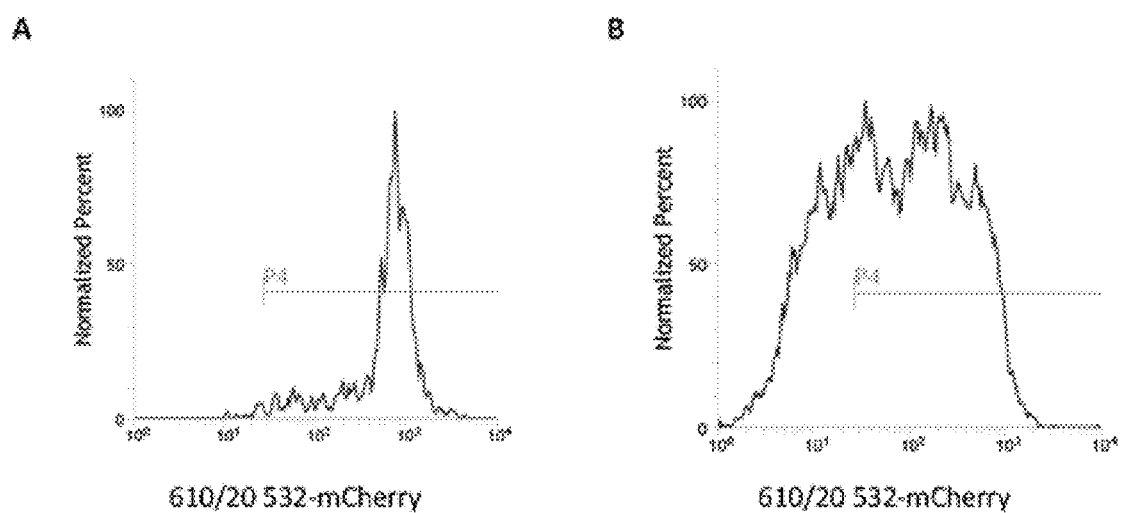

FIG. 25. FACS analysis of mCherry expression after pEP46 loading in HeLa CI.24.22 subclones. Two examples are shown. (A) Clone CI24.22.5. (B) Clone CI24.22.6. Fluorescence intensity was measured by FACS 10 days after transfection.

Figure 26:
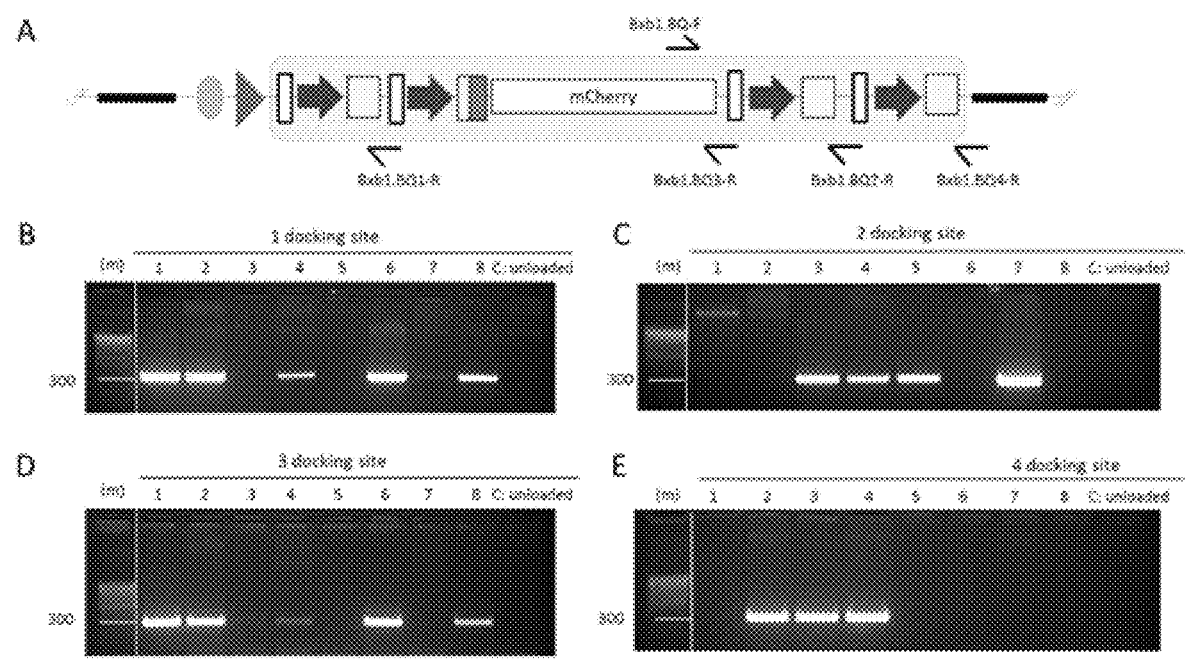

FIG. 26. Molecular characterization of docking sites loading in HeLa CI.24.22 subclones. (A) Diagram of the PCR strategy. (B, C, D and E) Agarose (2%) gel electrophoresis with ethidium bromide staining of PCR amplification products from sites 1, 2, 3 and 4, respectively. Molecular size marker=50 bp DNA ladder. Bold lines: CCR5 recombination arms; Light grey circle: phiC31-specific attB sites; Light grey triangle: SB-specific ITR elements; Docking module (DM): white rectangles: cHS4 insulator, arrows: SV40 promoter, light grey squares: Bxb1-specific attB site; Half light/dark grey square: Bxb1-specific attL sites.

Figure 27:
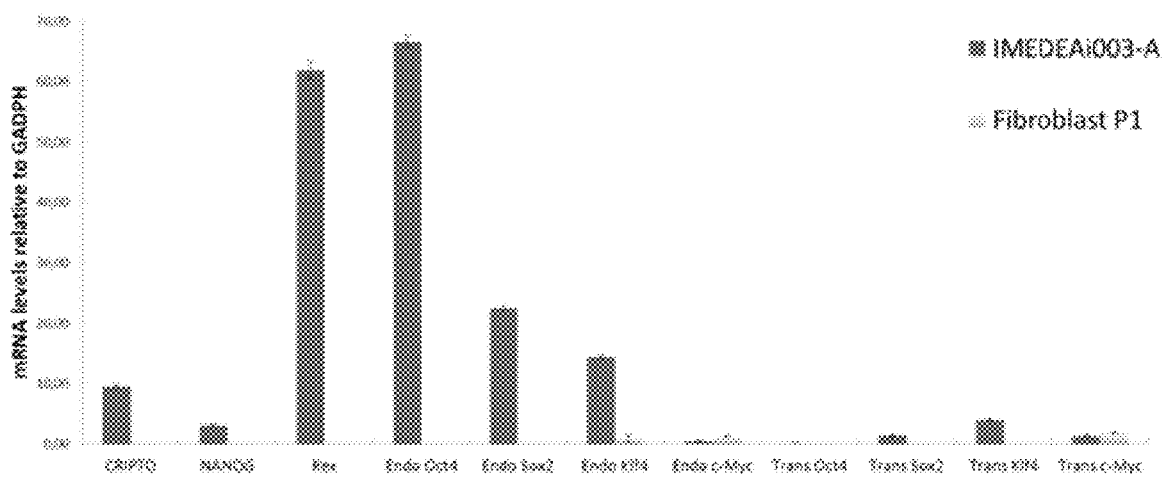

FIG. 27. Quantification of pluripotency markers by qRT-PCR. The expression levels of transgenic and endogenous pluripotent factors were quantified by qRT-PCR in WT hiPS cell line, and in primary fibroblasts as negative control. Expression values were plotted relative to GADPH expression.

Figure 28:
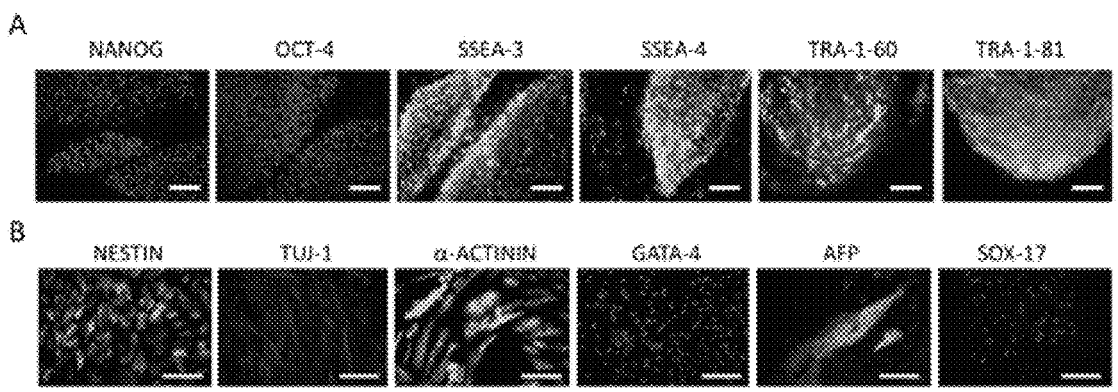

FIG. 28. Characterization of the hiPS cell line IMEDEAi003-A by immune-fluorescence studies. (A) Stem cell marker expression analysis in IMEDEAi003-A line confirmed the pluripotent state of the newly generated hiPC cells. (B) IMEDEAi003-A cells expressed markers of the three germ layers. Nuclei were counterstained with DAPI. (Scale bars: 100 µm)

Figure 29:
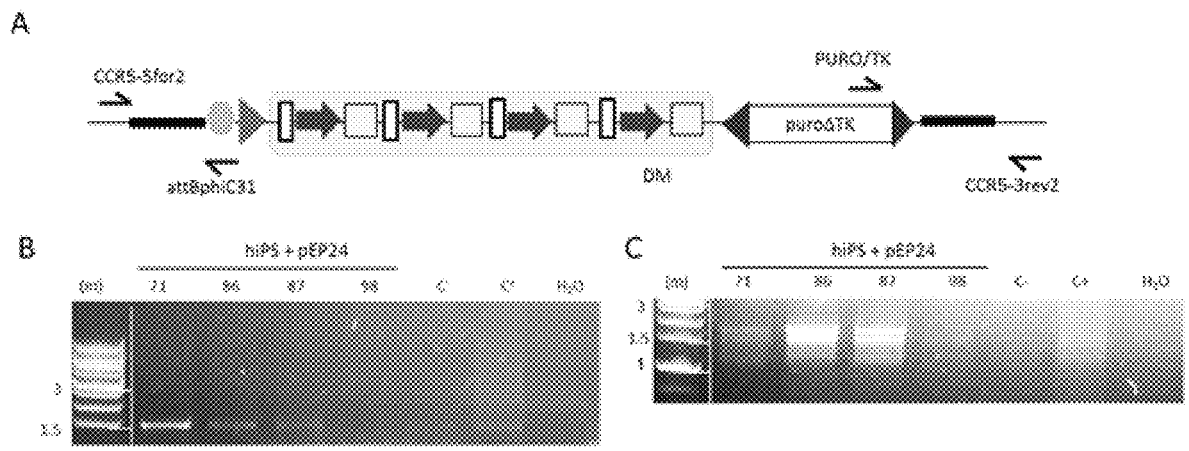

FIG. 29. Identification of recombined clones by PCR screening in step 1 of platform construction in hiPS cells. (A) Diagram of PCR characterization. (B) 5' integration site analysis by PCR using CCR5-5 for2/attBphiC31 primers (amplicon: 1500 bp). (C) 3' integration site analysis with the primers PB_HR reint fwd/CCR5-3rev2 (amplicon: 1800 bp). Agarose gel (0.8%) electrophoresis with ethidium bromide staining. Positive control: HeLa CI.24 cells containing the first docking module. Negative control: HeLa WT cells without docking module. Molecular size marker, m=1 kb DNA ladder. Bold lines: CCR5 recombination arms; Light grey circle: phiC31-specific attB sites; Light grey triangle: SB-specific ITR elements; Docking module (DM): white rectangles: cHS4 insulator, arrows: SV40 promoter, light grey squares: Bxb1-specific attB site; Dark grey triangles: PB-specific ITR elements.

Figure 30:
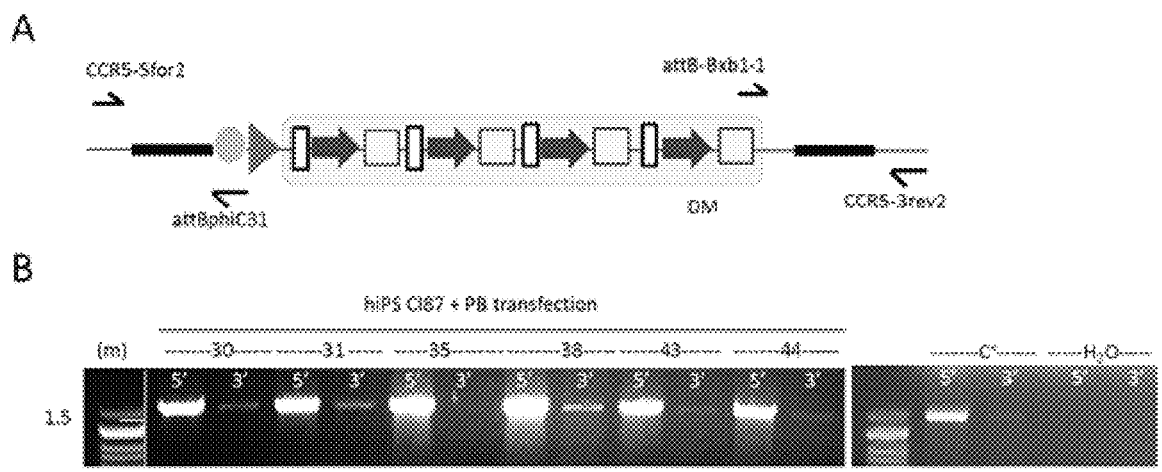

FIG. 30. Excision of the selection marker by PBc transposase in hiPS CI.87 cells. (A) Diagram of the PCR characterization. (B) Agarose gel (0.8%) electrophoresis with ethidium bromide staining. Representation of six clones analyzed by PCR using the CCR5-5 for 2/attBphiC31 pair of primers (amplicon: 1500 bp) or using attB-Bxb1-1/CCR5-3rev2 (amplicon: 1500 bp) to detect 3' excision site. Positive control: HeLa CI.24 cells harboring the first docking module. Agarose gel (0.8%) electrophoresis with ethidium bromide staining. Molecular size marker, m=50 bp DNA ladder. Bold lines: CCR5 recombination arms; Light grey circle: phiC31-specific attB sites; Light grey triangle: SB-specific ITR elements; Docking module (DM): white rectangles: cHS4 insulator, arrows: SV40 promoter, light grey squares: Bxb1-specific attB site.

Figure 31:
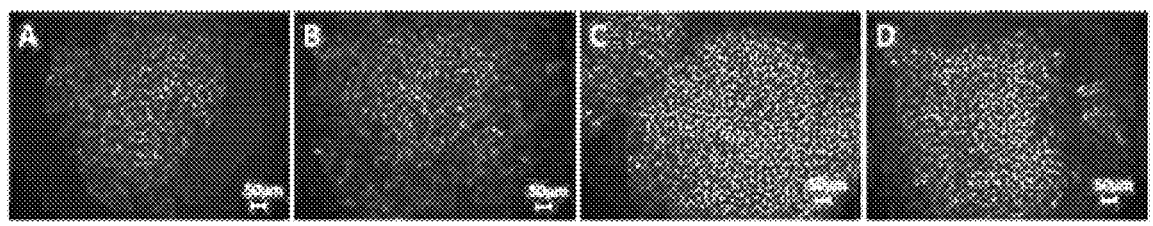

FIG. 31. Determination of mCherry fluorescence by epifluorescence microscopy after pEP46 loading in hiPS CI.87.38 cells. Fluorescence intensity was measured after 10 days of transfection by epifluorescence microscopy using the red channel and constant exposition. Scale bar=100 µm. (A) Clone 13. (B) Clone 18. (C) Clone 21, (D) Clone 22.

Figure 32:
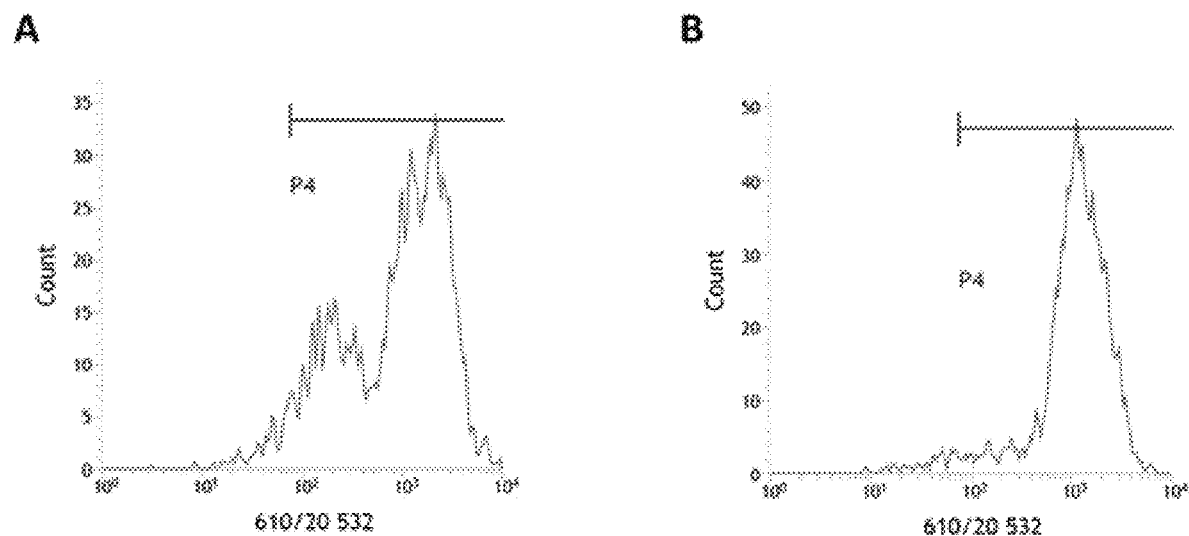

FIG. 32. FACS analysis of mCherry expression after pEP46 loading in hiPS CI.87.38 subclones. Two examples are shown. (A) Clone CI.87.38.22. (B) Clone CI.87.38.21. Fluorescence intensity was measured by FACS 10 days after transfection.

EXAMPLES

Example 1-Introduction of at Least One Recombinant Site into a Cell Genome of a Cell 1. Material and Methods
1.1. Materials
1.1.1—Laboratory Equipment

TABLE 1

Laboratory equipment

| | |
|---|---|
| Autoclave | Presoclave 75L (P-Selecta, Barcelona, Spain) |
| Centrifuges | BR4i multifunctions-S20 (Thermo Fisher Scientific, Massachusetts, USA). |
| | Biofuge fresco (rotor #3328) (Heraeus Instruments, Hanau, Germany) |
| | FiberLite F14-6x250LE, legend XTR centrifuge (Thermo Fisher Scientific, Massachusetts, USA) |
| | FiberLite F14-6x250LE, legend XTR centrifuge (Thermo Fisher Scientific, Massachusetts, USA) |
| | B4i multifunction. Thermo electron corporation (Thermo Fisher Scientific, Massachusetts, USA) |
| Thermo regulate devices | Modell 100-800 (Memmert, Schwabach, Germany) Flask. Infors HT-Ecotron (Bottmingen, Switzerland). Water bath PLS200 (Grant Instruments, Shepreth, UK) Thermomixes comfort (Eppendorf, Hamburg, Germany) |
| PCR machine | DNA engine-Peltier Thermal Cycler (Biorad Laboratories, California, USA) |
| | PTC-100 Programmable Thermal Controller (Biorad Laboratories, California, USA) |
| qPCR machine | iQ™ 5 Multicolor Real-Time PCR Cycler (Biorad Laboratories, California, USA) |
| Agarose Electrophoresis | Chamber (Biorad Laboratories, California, USA) |
| Spectrophotometer | Nanodrop (Thermo Fisher Scientific, Massachusetts, USA) |
| Nucleofector | 4D-Nucleofector (Lonza, Basel, Switzerland) |
| Incubator | Stericycle 160 CO2 incubator (Thermo Fisher Scientific, Massachusetts, USA) |
| Biosafety Cabinet | CLASS II-Cabinet. Telstar bio-II-A (Azbil Telstar, SI, Terrassa, Spain) |
| Microscopy | Leica DMIL (Leica, Wetzlar, Germany) |
| | Leica DMI 6000B inverted fluorescence microscope (Leica, Wetzlar, Germany) |
| Flowcytometry | Cytopedia BD INFLUX cell soter (BD Biociences, NYSE, USA) |

1.1.2—Plasmids

TABLE 2

Plasmids

| PLASMIDS | DESCRIPTION |
|---|---|
| pKOscrambler V920 | Cloning vector with ampicillin resistance (Stratagene, California, USA) |
| pmCherry-C1/C3 | Mammal expression vector designed to express a protein of interest that is fused to mCherry at the C-terminus mCherry is, a mutant fluorescent protein derived from the tetrameric Discosoma sp. red fluorescent protein, DsRed. (Clontech Laboratories, California, USA) |

TABLE 2-continued

Plasmids

| PLASMIDS | DESCRIPTION |
|---|---|
| pEP24-SV40 | Expression vector construct containing CCR5-5' and CCR5-3' homology arms, attB recombination site of phiC31 recombinase, SB transposon, cHS4 (insulator derived from the chicken β-globin locus), SV40 (simian viruspromoter), attB recombination site of Bxb1 recombinase, PB, PGK-puroΔtk (double selection cassette), hybrid puromycin/thymidine kinase under the control of the mouse phosphoglycerate kinase 1 promoter flanked by PB transposon. |
| pEP28-SV40 | Expression vector construct containing attP phiC31 attachment site, left-ITR of PB transposon. It harbors four attb Bxb1 elements plus other structures that constitute the docking module. PGK-puroΔtk (double selection cassette): hybrid puromycin/thymidine kinase protein under the control of the mouse phosphoglycerate kinase 1 promoter flanked by right-ITR of SB. |
| pEP50-SV40 | Expression vector containing the attR phiC31 attachment site, left-ITR of the Sleeping Beauty transposon. It harbors four attB Bxb1 elements plus other structures that constitute the docking system. PGK-puroΔtk (double selection cassette): puromycin/thymidine kinase under the control of the mouse phosphoglycerate kinase 1 promoter flanked by right-ITR of PB. |
| pEP46-mcherry | pmCherryC1 vector containing the attP Bxb1 attachment site at 5' of mCherry coding sequence. Promotorless. |
| pCMV_int | Expression vector containing the phiC31 recombinase for use in mammal system. It has been kindly provided by Dr. Michele Calos, Stanford University (USA). |
| pCS_KI | Expression vector containing the fusion protein gp3-phiC31 recombinase for use in mammal system. It has been kindly provided by Dr. Michele Calos, Stanford University (USA). |
| pCMV-Bx | Mammal expression vector containing the Bxb1 recombinase under the control of the CMV promoter. Addgene #51552 (USA). |
| pCMV-HAhyPBase | pcDNA3.1 expression vector of the HA-tagged hyperactive piggyBac transposase |
| SB100X | pCMV(CAT)T7-SB100 containing Sleeping Beauty (SB100X) transposase. Addgene #34879 (USA). |
| PB(R/L) | pUC57 cloning vector with the PiggyBac transposon. Genewiz (USA). |
| SB(R/L) | pUC57 cloning vector with the Sleeping Beauty transposon. Genewiz (USA). |
| SV40-attB-Bxb1 | pUC57 cloning vector with four cHS4 elements (insulator sequences derived from the chicken β-globin locus), four SV40 promoters and the attB attachment site for Bxb1. Genewiz (USA). |

1.1.3—Primers

The following oligonucleotides were purchased from Thermo Fisher Scientific (Massachusetts, USA). Their use is described in the text.

TABLE 3

Primers

| Name | Sequence (5' → 3') |
|---|---|
| FORWARD-Golden GATE | |
| GG1-F | GCGCGTCTAGAGGATCCCGAGCTCACG (SEQ ID NO: 1) |
| GG2-F | GCGTCTAGACGTCTCACATGCGAGCTCACG (SEQ ID NO: 2) |
| GG3-F | GCATCTAGACGTCTCAGGACCGAGCTCACG (SEQ ID NO: 3) |
| GG4-F | GCTTCTAGACGTCTCACCAGCGAGCTCACG (SEQ ID NO: 4) |
| REVERSE-Golden GATE | |
| GG1-R | CGACGCGTCATGTGAGACGGCCCGGATGA (SEQ ID NO: 5) |
| GG2-R | TTTACGCGTGTCCTGAGACGGCCCGGATGA (SEQ ID NO: 6) |
| GG3-R | TTTACGCGTCTGGTGAGACGGCCCGGATGA (SEQ ID NO: 7) |
| GG4-R | TTACGCGTGGCGCGCCTATTGCTAGCGCCCGGATGA (SEQ ID NO: 8) |
| Recombination arms | |
| 480up | GACTGAGTTGCAGCCGGGCATG (SEQ ID NO: 9) |
| 480d0wn | ACCAACCAGGATCTCCCTGCTCAG (SEQ ID NO: 10) |
| CCR5-5homUP | TATGCGGCCGCACGCGTTCCAGGCTGCAGTGAGCCATG (SEQ ID NO: 11) |
| CCR5-5homDN | CCTGCTAGCGAGACGTCATTAAAACACAGCCACCACCCAAGTG (SEQ ID NO: 12) |
| CCR5-3homUP | TATCCTGCAGGTGCTTGTCATGGTCATCTGCTACTCG (SEQ ID NO: 13) |
| CCR5-3homDN | TTTACGCGTGCTTCCCCAGCTCTCCAGG (SEQ ID NO: 14) |
| oligonucleotides | |
| attP-Bxb1-up | CATGTGTCGTGGTTTGTCTGGTCAACCACCGCGGTCTCAGTGGTGTACGGTACAAACCCAG (SEQ ID NO: 15) |
| attP-Bxb1-down | CTAGCTGGGTTTGTACCGTACACCACTGAGACCGCGGTGGTTGACCAGACAAACCACGACA (SEQ ID NO: 16) |

TABLE 4

Primers for molecular characterization

| Name | Sequence (5'→3') |
|---|---|
| CCR5-5for2 | CAGGCTTCCCGCATTCAAAAT (SEQ ID NO: 17) |
| attBphiC31 | GATGGGTGAGGTGGAGTACG (SEQ ID NO: 18) |
| CCR5-3rev2 | TGTCTCCTTCTACAGCCAAGC (SEQ ID NO: 19) |
| PURO/tk | GGTAATGACAAGCGCCCAGA (SEQ ID NO: 20) |
| attB-Bxb1-1 | GCGCTAGCGAATTCGTATGTT (SEQ ID NO: 21) |
| attLphiC31 | CAACCCCTTGTGTCATGTCG (SEQ ID NO: 22) |
| attRphiC31 | TTTTCCCAGGTCAGAAGCGG (SEQ ID NO: 23) |
| attxphiC31 | AGTGTGATCACTTGGGTGGTG (SEQ ID NO: 24) |
| 3'_SB | CATCACATTCCCAGTGGGTCA (SEQ ID NO: 25) |
| cHS4_R | GTAATTACATCCCTGGGGGCTT (SEQ ID NO: 26) |
| PB_R | TGACGCATGTGTTTTATCGGT (SEQ ID NO: 27) |
| SB_R | TCCCTGTCTTAGGTCAGTTAGGA (SEQ ID NO: 28) |
| CCR5_Cat_980_UP | AAGATGGATTATCAAGTGTCAAGTCC (SEQ ID NO: 29) |
| CCR5_Sang_490_20UP | TTAAAAGCCAGGACGGTCAC (SEQ ID NO: 30) |
| cHS4.BQ-F | TCATCCAACTCCAGGACGGA (SEQ ID NO: 31) |
| Bxb1.BQ-F | GGACAGGTATCCGGTAAGCG (SEQ ID NO: 32) |
| Bxb1.BQ1-R | CCCGTGAGCTCGCATGT (SEQ ID NO: 33) |
| Bxb1.BQ2-R | GTGAGCTCGGTCCTGAGAC (SEQ ID NO: 34) |
| Bxb1.BQ3-R | GTGAGCTCGCTGGTGAGAC (SEQ ID NO: 35) |
| Bxb1.BQ4-R | AGCTGCAGGTTTAAACAGTCG (SEQ ID NO: 36) |

1.1.4—Bacteria Strains and Mammal Cell Lines 1.1.4.1—Bacterial Strains

Supercompetent XL1-blue cells were used for all cloning and transformation procedures. XL1-Blue Genotype: recA1 endA1 gyrA96 thi-1 hsdR17 supE44 relA1 lac [F' proAB laciqZΔM15 Tn10 (Tetr)].

1.1.4.2—Mammal Cell Lines

Hela cells. Human cell line derived from cervical cancer cells (Scherer, W. F., Syverton, J. T. and Gey, G. O. 1953, Journal of Experimental Medicine, 97 (5): 695-710).

HAFi-W3R feeder cells. Immortalized Human Adult Fibroblast (HAFi) with resistance to three antibiotics (G418, puromycin and hygromycin) (Dravid, G., et al. 2006. *In Human Embryonic Stem Cell Protocols*. s.l.: Humana Press, pp. 91-104; Cai, L., et al. 2007, Cell research, 17 (1): 62-72.; Dravid, G., et al. 2005, Stem cells, 23 (10): 1489-1501). In addition, over-expression of the Wnt3a transgene enhanced the ability of HAFi-W3R feeder cells to support the undifferentiated growth of hiPS cells (Lorenzo, I. M., Fleischer, A. and Bachiller, D. Stem Cell Reviews and Reports, 9 (4): 435-450, 2013).

IMEDEAi003-A. human induced pluripotent stem (hiPS) cells reprogrammed from skin biopsies (fibroblast) of healthy individual by MKOS retroviral infection (Fleischer, A., et al. 2018, Stem cell research, 29:1-5).

1.1.5 Software

TABLE 5

Software

| | |
|---|---|
| Electrophoresis | GeneSnap (Syngene, NJ, USA) |
| Spectrophotometer | ND-100 V3.8.1 (Thermo Fisher Scientific, Massachusetts, USA) |
| Sequence analysis and Design | Vector NTI Express Designer (Thermo Fisher Scientific, Massachusetts, USA), SerialCloner2-1 (Serial Basics, France) |
| Online applications | BLAST data analysis (NCBI, Bethesda MD, USA) |
| qRT PCR | qPCR Analysis Software (Biorad Laboratories, California, USA) |
| Fluorescence microscopy | Microscope Imaging Software: Leica Microsystems (Leica, Wetzlar, Germany) |
| Flowcytometry | Sortware (BD Biociences, NYSE, USA) |

1.2—Methods
1.2.1—Molecular Biology Methods
1.2.1.1—RNA Isolation and Quantitative RT-PCR Total RNA was isolated using the RNeasy Mini Kit (Qiagen, Hilden, Germany) following manufacturer's instructions. 50 ng of RNA was used to synthesize cDNA with the Sensiscript® Reverse Transcriptase (Qiagen, Hilden, Germany). Master mix reaction and thermocycler program are showed below in table 6:

TABLE 6

Master mix reaction and thermocycler program

| Master mix-Sensiscript | | cDNA synthesis program | | |
|---|---|---|---|---|
| 10× buffer RT | 2 µl | Step 1 | 25° C. | 10 minutes |
| 25× dNTPs | 0.8 µl | Step 2 | 37° C. | 120 minutes |
| oligo dt (20 µM) | 1 µl | Step 3 | 85° C. | 5 minutes |
| RNAase inhibitor (10 U/µl) | 1 µl | Step 4 | 4° C. | ∞ |
| RNA | 1 µl | | | |
| H2O | 4.2 µl | | | | qPCR analyses were performed on a iQT5 Multicolor Real-Time PCR Cycler (Biorad Laboratories, California, USA) with the KAPA SYBR FAST Universal qPCR Kit (KAPA Biosystems, Woburn/MA, KK4600). The primers for either endogenous or transgenic genes have been previously described (Aasen, T., et al. 2008, Nature Biotechnology, 26 (11): 1276-1284).

TABLE 7

Primer; F, Forward (5'→3'); R, Reverse (5'→3')

| | | |
|---|---|---|
| NANOG | F | ACAACTGGCCGAAGAATAGCA (SEQ ID NO: 37) |
| | R | GGTTCCCAGTCGGGTTCAC (SEQ ID NO: 38) |

TABLE 7-continued

Primer; F, Forward (5'→3'); R, Reverse (5'→3')

| | | |
|---|---|---|
| CRIPTO | F | CGGAACTGTGAGCACGATGT (SEQ ID NO: 39) |
| | R | GGGCAGCCAGGTGTCATG (SEQ ID NO: 40) |
| REX1 | F | CCTGCAGGCGGAAATAGAAC (SEQ ID NO: 41) |
| | R | GCACACATAGCCATCACATAAGG (SEQ ID NO: 42) |
| GAPDH | F | GCACCGTCAAGGCTGAGAAC (SEQ ID NO: 43) |
| | R | AGGGATCTCGCTCCTGGAA (SEQ ID NO: 44) |
| Trans-OCT4 | F | TGGACTACAAGGACGACGATGA (SEQ ID NO: 45) |
| | R | CAGGTGTCCCGCCATGA (SEQ ID NO: 46) |
| Trans-SOX2 | F | GCTCGAGGTTAACGAATTCATGT (SEQ ID NO: 47) |
| | R | GCCCGGCGGCTTCA (SEQ ID NO: 48) |
| Trans-KLF4 | F | TGGACTACAAGGACGACGATGA (SEQ ID NO: 49) |
| | R | CGTCGCTGACAGCCATGA (SEQ ID NO: 50) |
| Trans-c-MYC | F | TGGACTACAAGGACGACGATGA (SEQ ID NO: 51) |
| | R | GTTCCTGTTGGTGAAGCTAACGT (SEQ ID NO: 52) |
| Endo-OCT4 | F | GGGTTTTTGGGATTAAGTTCTTCA (SEQ ID NO: 53) |
| | R | GCCCCCACCCTTTGTGTT (SEQ ID NO: 54) |
| Endo-SOX2 | F | CAAAAATGGCCATGCAGGTT (SEQ ID NO: 55) |
| | R | AGTTGGGATCGAACAAAAGCTATT (SEQ ID NO: 56) |
| Endo-KLF4 | F | AGCCTAAATGATGGTGCTTGGT (SEQ ID NO: 57) |
| | R | TTGAAAACTTTGGCTTCCTTGTT (SEQ ID NO: 58) |
| Endo-c-MYC | F | CGGGCGGGCACTTTG (SEQ ID NO: 59) |
| | R | GGAGAGTCGCGTCCTTGCT (SEQ ID NO: 60) |

Master mix reaction and thermocycler program for qPCR analysis are showed below:

TABLE 8

Master mix reaction and thermocycler program for qPCR

| Master mix-Sensiscript ® | | Program thermocycler | | |
|---|---|---|---|---|
| SYBR | 12.5 µl | Step 1 | 95° C. | 10 minutes |
| Primer UP | 0.5 µl | Step 2 | 95° C. | 120 minutes |
| Primer DOWN | 0.5 µl | Step 3 | 55° C. | 5 minutes |
| Template | 1 µl | Step 4 | | Go to step 2 |
| H2O | 10.5 µl | | | (490 cycles) |

1.2.1.2—Cloning Procedures

All cloning steps involved standard techniques such as quantitative restriction enzyme analysis, separation of DNA fragments by agarose gel electrophoresis, DNA extraction and purification of the desired DNA fragments, ligation, bacterial transformation, plasmid DNA miniprep purification and, finally, analytical plasmid digestion to identify the correctly cloned construct.

1.2.1.2.1—Enzymatic Digestion

All enzymes used in digestion analyses belong to the type IIS restriction enzyme family. Digestions were incubated for 2-4 h at 37-55° C. according to manufacturer's instructions. Conditions for standard reaction depending on number of enzymes used are showed below:

TABLE 9

Conditions for standard reaction depending on number of enzymes

| Standard unique enzyme digestion | Standard double enzymes digestion |
|---|---|
| 2 µl specific enzymatic buffer (10×) | 3 µl specific enzymatic buffer (10×) |
| 0.5 µl enzyme | 0.5 µl enzyme A |
| 2 µg plasmid DNA | 0.5 µl enzyme B |
| x to 20 µl ddH$_2$O | 2 µg DNA |
|  | x to 30 µl ddH2O |

To verify the newly cloned constructs, plasmid DNA was digested with different restriction enzymes. The unique electrophoretic pattern of the fragments indicated if the right insert had been correctly cloned into the vector. Two control digestions were usually carried out. First, plasmids were digested with enzymes that cut inside and outside the insert. Then, to confirm correct cloning, the resulting positive clones were digested with another enzyme resulting in a different restriction pattern.

1.2.1.2.2—DNA Purification from Agarose Gels

Analytical and preparative gel electrophoresis of double-stranded DNA fragments was performed in 0.8% for 0.8-4 kb or 2% for 0.05-0.8 kb agarose gels supplemented with ethidium bromide (0.1 mg/ml) (329). DNA fragment sizes were determined by using DNA markers (50 bp or 1 kb depending on the length of the expected DNA fragments). Bands were visualized using a UV transilluminator at 302 nm.

DNA fragments were excised from agarose gel with a scalpel and purified on columns according to the manufacturer's instructions (E.Z.N.A Gel extraction kit (Omega, Georgia, USA).

1.2.1.2.3—Ligation Reactions

All ligation reactions were performed using the Mighty Mix DNA ligation Kit (Takara Bio, Kioto, Japan) at a 1:3 vector: insert molar ratio. Standard ligation mixes generally contained 100 ng of total DNA. Standard ligation reaction was prepared as follows: 8 µl ligation mix, 10 µl DNA fragments, 2 µl ddH$_2$O and VT=20 µl for 5 min at 25° C.

1.2.1.2.4—Bacterial Transformation

XL1-blue supercompetent cells were transformed following standard protocols. The complete ligation mixture (20 µl) was added to 50 µl of competent cells (1×10$^5$), mixing gently by pipetting up and down. The mixture was incubated for 30 min on ice, exposed to heat shock for 40 sec at 42° C., and chilled on ice for 40 sec. Finally, 1,000 µl of Luria-Bertani (LB) media was added for the recovery phase and incubated for 60 minutes at 37° C. with vigorous shaking (180 rpm). Transformed bacteria were centrifuged at 13,000 rpm and the supernatant discarded, leaving around 30-60 µl which were seeded on pre-warmed agar plates with the appropriate selection antibiotic. Agar plates were incubated O.N. at 37° C. On the following day, 6-24 colonies were picked and individually grown in 2 ml LB plus antibiotic on a shacker at 180 rpm O.N. at 37° C. Next day, plasmid DNA was extracted using the miniprep kit (miPlasmid Miniprep kit-Metabion, Germany).

1.2.2—Karyotyping

A standard optimized G-banding technique with slight modifications was used to karyotype hiPS cell lines. Briefly, actively proliferating cells were treated with 10 µg/ml colcemid (Sigma, Spain) for 1 to 3 hours, trypsinized, washed in phosphate-buffered saline (PBS) and incubated in hypotonic PBS (74.85 mOsm/kg H$_2$O) for 20 minutes, before immersing them in Carnoy's fixative (cold methanol/acetic acid 3:1, both from BDH) for 30 minutes. Nuclei were then centrifuged at 500×g for 2 minutes and resuspended in fresh Carnoy's to wash residual PBS. Fixed nuclei were spread and G-banded by Prenatal Genetics, Barcelona. At least 20 selected spreads were banded to produce a result in each line.

1.2.3—Immunoflourescence and Histochemistry

Undifferentiated hiPS cells were washed with PBS, fixed for 20 minutes with 4% paraformaldehyde, and washed again with PBS. Immunocytochemistry was performed for NANOG (1:150, rabbit IgG polyclonal, Abcam, Spain), OCT4 (1:100, mouse IgG monoclonal, Santa Cruz Biotechnology, USA), SSEA3 (1:100, rat IgM, Millipore, USA), SSEA4 (1:100, mouse IgG, Millipore, USA), TRA-1-60 (1:100, mouse IgM, Millipore, USA), TRA-1-81 (1:100, mouse IgM, Millipore, USA), α-AFP (1:100, rabbit IgG, Dako, Denmark), NESTIN (1:500, rabbit IgG, Sigma, Spain), TUJ1 (1:500, rabbit IgG, Covance, UK), SOX17 (1:100, goat IgG, R&D Systems, UK), α-ACTININ (1:200, mouse igM, Sigma, Spain) and GATA4 (1:300, mouse IgG, Santa Cruz Biotechnology, USA). Permeabilization was carried out with 0.2% Triton X-100 (Sigma, Spain) and 100 mM glycine in PBS for 30 minutes at room temperature. Blocking was performed by incubating the cells with 5% BSA in PBS for 30 minutes at room temperature. Cells were incubated with primary antibodies O.N. at 4° C. in 2% BSA in PBS, followed by three washing steps with PBS. Alexa Fluor 555 (1:500, donkey anti-mouse IgG or donkey anti-rabbit IgG Invitrogen, USA), Alexa Fluor 546 (1:500, donkey anti-goat IgG, Invitrogen, USA), Alexa Fluor 488 (1:500, donkey anti-mouse IgG, donkey anti-rabbit IgG or donkey anti-rat, Invitrogen, USA) were used as secondary antibodies, incubated 1 hour at room temperature with 2% BSA in PBS. After washing with PBS, cells were stained with DAPI (5 minutes, 1 µg/ml), washed three times and mounted with Dako fluorescent mounting medium. Pictures were taken with a Leica DMI 6000B microscope system.

1.2.4-Fluorescence Activated Cell Analysis and Sorting 72 hours after transfection, cells were dissociated using Trypsin/EDTA (Invitrogen, USA) or Tryple Express (Thermo Fisher, USA), washed with PBS (Invitrogen, USA) and resuspended in sorting buffer (PBS with 2% FBS (Biowest, France) or KRS (Biowest, France), 0.2% penicillin/streptomycin and DAPI (1 µg/ml). To avoid clumps, cells were filtered through a 40 µm cell strainer. Flow cytometry analysis and sorting was performed with a Cytopedia BD INFLUX cell sorter (BD Biociences, NYSE, USA). DAPI positive cells were excluded from sorting. Cells were collected into 15 ml Falcon tubes with DMEM complete media supplemented with 20% FBS and 0.2% penicillin/streptomycin. Based on fluorescence intensity, cells were sorted and separated into low and high mCherry expressing cells.

Subsequently sorted cells were centrifuged for 5 minutes at 320×g and seeded in a p6 well.

1.2.5-Genomic DNA Extraction

Cells were harvested and centrifuged in PBS. The supernatant was discarded and genomic DNA extracted using 300 µl lysis buffer (20 mM Tris, 100 mM NaCl, 1 mM EDTA, 1 mg/ml proteinase K). The mix was incubated O.N. at 55° C. Following centrifugation at 3,200 rpm, supernatant was discarded and 700 µl NaCl/ETOH 100% (at −20° C.) was added. The reaction mix was incubated for 30 minutes at −20° C., centrifuged and rinsed twice with 700 µl 70% ETOH. After last rinse, pellets were air-dried for 15-20 minutes. Samples were resuspended in 50 µl of ddH2O.

1.2.6—PCR Strategy for Characterization of the Genomic Loci Following Recombination.

Figure 1:
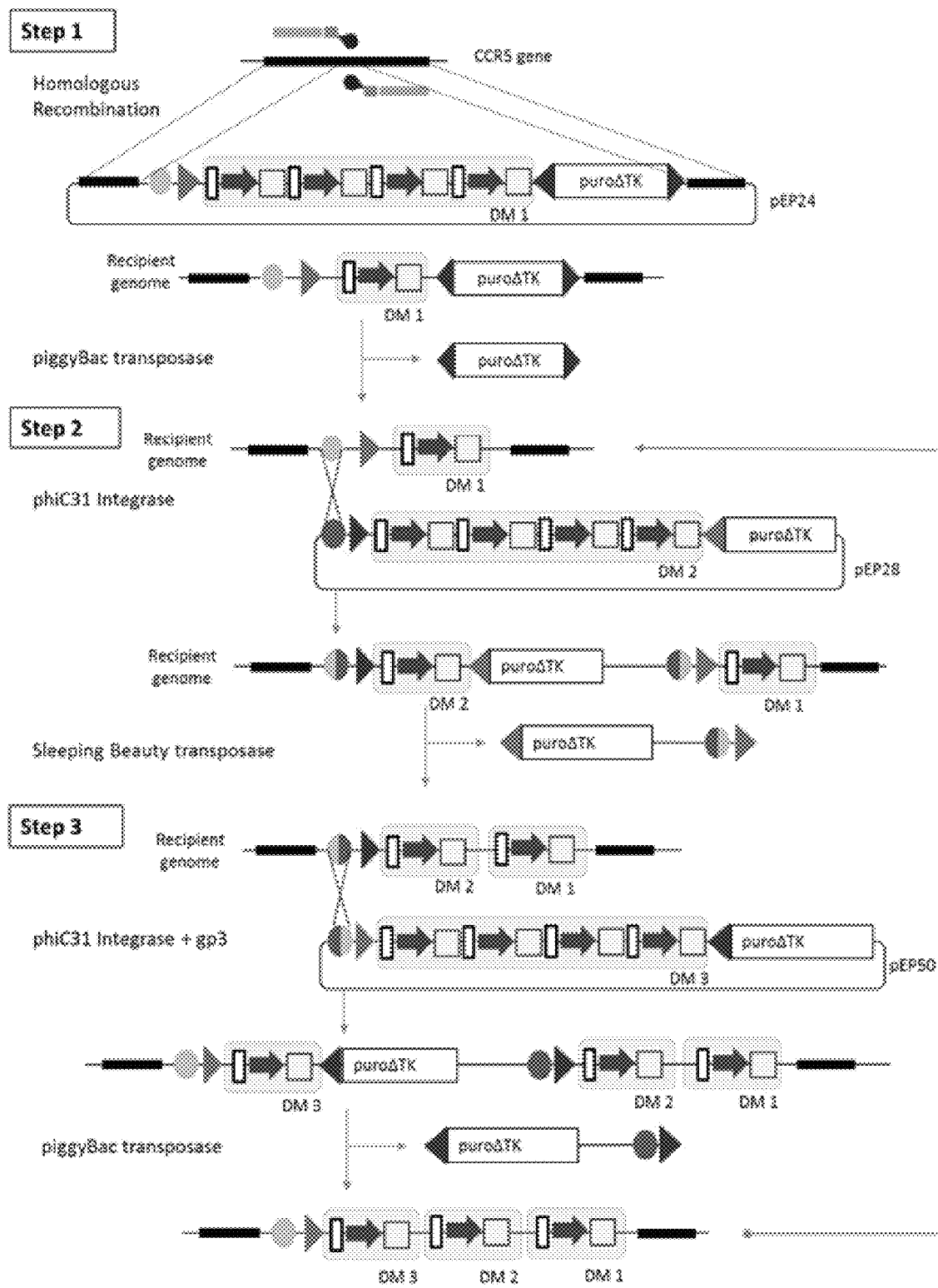
FIG. 1. Diagram of the building strategy. Step 1, integration of the vector carrying a docking module (DM) by TALEN-assisted homologous recombination into the CCR5 locus, followed by excision of the selection element (puroΔtk) by PB transposition. Step 2, integration of a second docking module by phiC31-assisted site-specific recombination. Step 3, integration of a third docking module by phiC31/gp3-assisted site-specific recombination. Bold black line: CCR5 recombination arms. Light grey circles: phiC31-specific attB sites. Dark grey circles: phiC31-specific attP sites. Half dark/light grey circles: phiC31-specific attR sites. Half Light/dark grey circles: phiC31-specific attL sites. Light grey triangles: SB-specific ITR elements. Dark grey triangles: PB-specific ITR elements. DM composition: white rectangle: cHS4 insulator, arrows: SV40 promoters and squares: Bxb1-specific attB sites.
Figure 2:
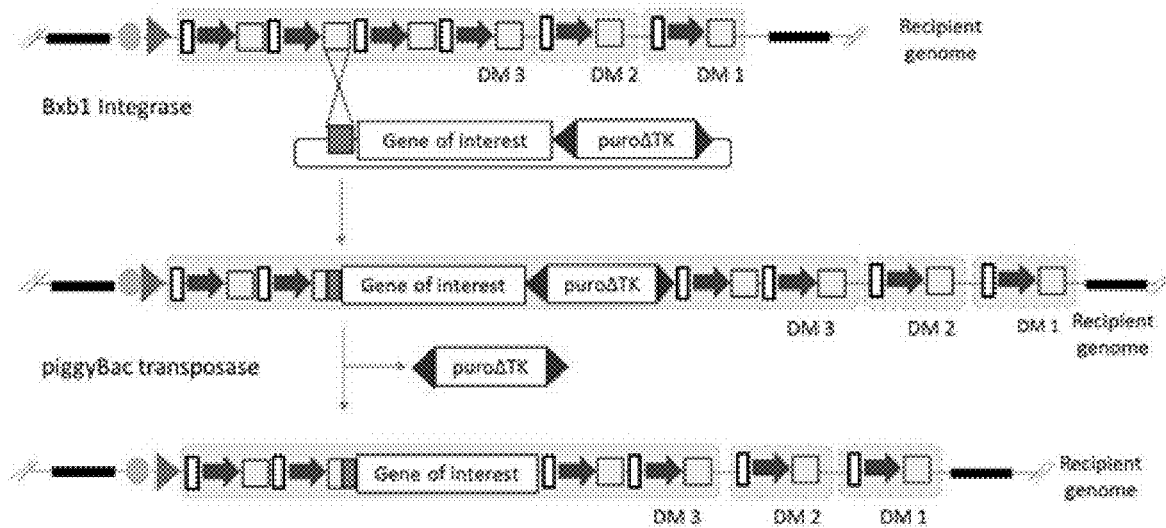
FIG. 2. Diagram of the loading process. Integration Bxb1-assisted site-specific recombination of a typical loading module carrying a promoterless gene. Bold black line: CCR5 recombination arms. Light grey circle: phiC31-specific attB sites. Light grey triangle: SB-specific ITR elements. Dark grey triangle: PB-specific ITR elements. White rectangle: cHS4 insulator. Arrow: SV40 promoter. Light grey square: Bxb1-specific attB site. Dark grey square: Bxb1-specific attP sites. Half light/dark grey square: Bxb1-specific attL sites.
Figure 3:
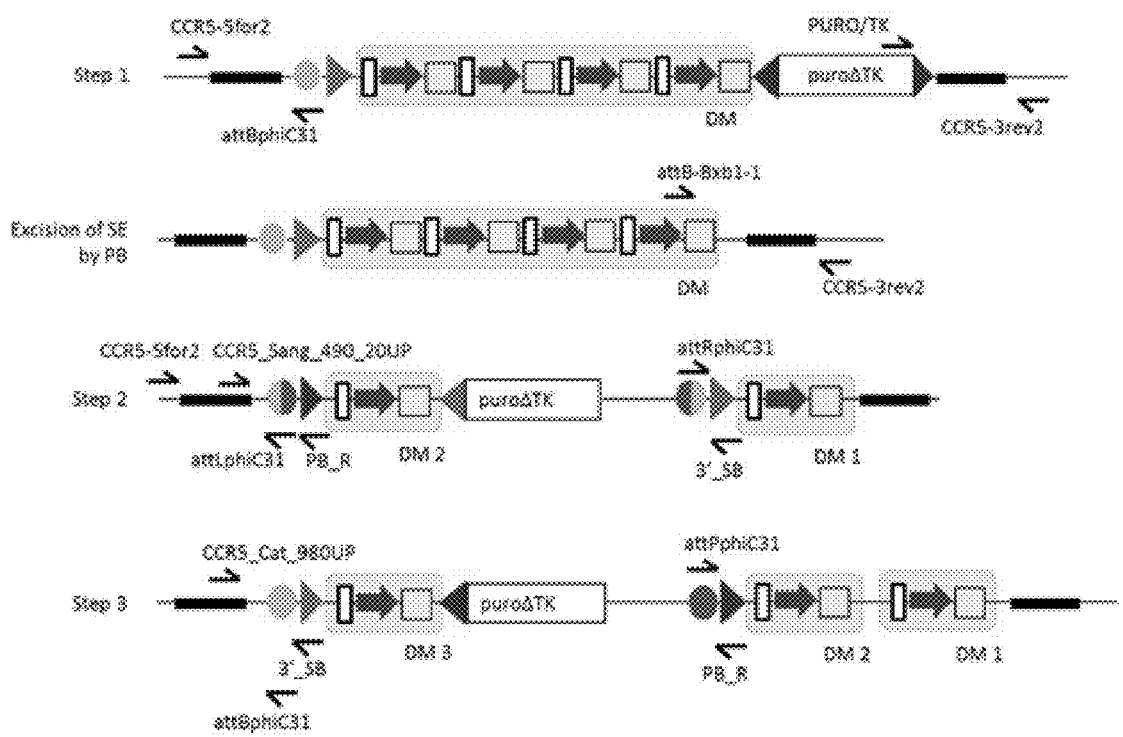
FIG. 3. Position of primers used to verify the integration of the different modules used during the process. Step 1, CCR5 locus structure of after HR. CCR5-5 for2 (forward) and attBphiC31 (reverse) primers to check 5' recombination, and PURO/tk (forward) and CCR5-3rev2 primers to check 3' recombination. Excision of selection element (SE) by PB transposase: attB-Bxb1-1 (forward) and CCR5-3rev2 (reverse) primers to screen for SE-free clones. Step 2, locus structure after site-specific phiC31 attB/attP recombination, CCR5-5 for2 and CCR5_Sang_490_20UP (forward) primers, and attLphiC31 or PB_R (reverse) primers to check 5' recombination. attRphiC31 (forward) and 3'_SB (reverse) primers to check 3'recombination. Step 3, locus structure after site-specific attL/attR recombination by phiC31 plus gp3, CCR5_Cat_980UP (forward) and attBphiC31 or 3'_SB (reverse) primers to check 5' recombination. attPphiC31 (forward) and PB_R (reverse) primers to check 3' recombination. Bold black line: CCR5 recombination arms. Light grey circles: phiC31-specific attB sites. Dark grey circles: phiC31-specific attP sites. Half dark/light grey circles: phiC31-specific attR sites. Half light/dark grey circles: phiC31-specific attL sites. Light grey triangles: SB-specific ITR elements. Dark grey triangles: PB-specific ITR elements. Docking module (DM) composition: white rectangle: cHS4 insulator, arrows: SV40 promoters and light grey squares: Bxb1-specific attB sites.

To evaluate the correct integration of the donor DNA during HR and site-specific recombination, 5' and 3' integration sites were checked by Polymerase Chain Reaction (PCR) with specific pairs of primers. In both cases, one primer pair attaches to a region outside and the other inside the recombination cassette.

phC31-dependant site-specific recombination events were characterized by detecting the newly generated att-sites. Primer sequences and their localization in the genome are presented in section 1.1.3 above-Primers. Length and location of PCR amplicons as well as melting temperature (Tm) of primers are presented FIG. 3 and Table 10, respectively.

Figure 4:
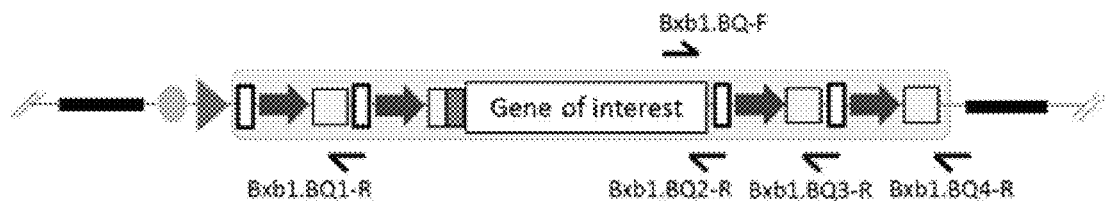
FIG. 4. Position of primers used to verify loading status in each one of the different docking units. Docking module structure after site-specific integration by Bxb1. Bxb1.BQ-F and Bxb1.BQ-R (1-4) are the docking unit-specific primers. Bold black line: CCR5 recombination arms. Light grey circle: phiC31-specific attB site. Light grey triangle: SB-specific ITR element. DM composition: white rectangle: cHS4 insulator, arrows: SV40 promoters and Light grey squares: Bxb1-specific attB sites. Half light/dark grey square: Bxb1-specific attL sites.

Bxb1-dependant site-specific recombination events were characterized by detecting the unique BsmBI site present in each one of the four docking sites present in the docking module (FIG. 4). Primer sequences and their localization in the genome are presented in Table 10 and FIG. 4, respectively. PCR product lengths and melting temperature (Tm) of the different pairs of primers are also presented in Table 10.

TABLE 10

| Primer pairs | | Length | Tm (° C.) |
|---|---|---|---|
| Forward | Reverse | | |
| CCR5-5for2 | attBphiC31 | 1053 | 65 |
| PURO/tk | CCR5-3rev2 | 2500 | 65 |
| PB HR reint fwd | CCR5-3rev2 | 1800 | 65 |
| CCR5-5for2 | attLphiC31 | 1500 | 65 |
| attB-Bxb1-1 | CCR5-3rev2 | 1500 | 65 |
| attRphiC31 | 3'_SB | 173 | 63 |
| attRphiC31 | PB_R | 343 | 63 |
| CCR5_Sang_490_20UP | attLphiC31 | 170 | 63 |
| CCR5_Cat_980_UP | attBphiC31 | 581 | 63 |
| attxphiC31 | cHS4_R | 581 | 63 |
| attxphiC31 | SB_R | 296 | 63 |
| attxphiC31 | PB_R | 456 | 63 |
| Bxb1.BQ-F | Bxb1.BQ1-R | 306 | 60 |
| Bxb1.BQ-F | Bxb1.BQ2-R | 303 | 60 |
| Bxb1.BQ-F | Bxb1.BQ3-R | 303 | 60 |
| Bxb1.BQ-F | Bxb1.BQ4-R | 338 | 60 |

Each docking element was assembled by Golden Gate cloning (see Results, 2.2), using the type IIS endonuclease BsmBI, whose recognition sequence includes 4 variable bases (CGTCTCNANNNN (SEQ ID NO: 61)). By modifying the bases, the Golden Gate system allows simultaneous assembly of the four modules in a single cloning step. At the same time, it provides specific PCR targets to check the docking status of the different units.

PCR reactions were carried out using the WonderTaq polymerase (Euroclone, via Figino, Italy) according to the following program:

TABLE 11

| PCR Reaction. | | | |
|---|---|---|---|
| PCR program | | | Reaction mix |
| Step | Temperature | Time | 5 µl buffer |
| Step 1 | 95° C. | 1 minutes | 2 µl primer UP |
| Step 2 | 95° C. | 15 seconds | 2 µl primer DOWN |
| Step 3 | X* C. | 30 seconds | 0.5 µl taq polymerase |
| Step 4 | 72° C. | Y** | 150-300 ng template (DNA) |
| Step 5 | Go to step 2 (33 cycles) | | x to 25 µl ddH2O |
| Step 6 | 72° C. | 1 minute | |
| Step 7 | 4° C. | ∞ | |

*X: annealing temperature depends on PCR primer pairs.
**Y: elongation time depends on amplified PCR product (1 minute for 1 kb length)

1.2.7—Sequencing

Genomic DNA from individual hiPS and Hela cell clones was PCR amplified and sanger sequenced using the primers attxphiC31/cHS4_R; attxphiC31/SB_R; and attxphiC31/PB_R. A 5 µl aliquot of the PCR reaction was run on a 2% agarose gel to check the size of PCR products. Following confirmation, PCR products were purified and sent to sequencing at SECUGEN (Madrid, Spain) Table 11.

TABLE 12

| PCR program (ExTaq) | | | Reaction mix |
|---|---|---|---|
| Step | Temperature | Time | 5 µl buffer |
| Step 1 | 95° C. | 1 minute | 4 µl dNTPs |
| Step 2 | 98° C. | 10 seconds | 2.5 µl primer UP |
| Step 3 | x° C.* | 30 seconds | 2.5 µl primer DOWN |
| Step 4 | 72° C. | Y** | 0.25 µl taq polymerase |
| Step 5 | Go to step 2 × 30 cycles | | 150-300 ng template (DNA) |
| Step 6 | 72° C. | 2 minutes | x to 50 µl ddH2O |
| Step 7 | 4° C. | ∞ | |

1.2.8—Cell Biology Methods 1.2.8.1—Cell Culture

Hela cells and subclones were cultured in complete medium (DMEM High glucose (Biowest, France) supplemented with 10% fetal bovine serum (FBS) (Biowest, France), 2 mM Glutamax and 1% non-essential aminoacids (NEAA) (Invitrogen, USA), 50 U/ml penicillin/streptomycin (Thermo Fisher Scientific, USA). Hela cells were maintained in a humidified atmosphere at 37° C., 5% CO2, Cells were passaged at 80-90% confluency (one or twice weekly) and never diluted more than 1:10. For passaging, culture-medium was removed and cells were washed twice with PBS. 1 ml of trypsin/EDTA (Invitrogen, USA) was added per 100 mm culture dish and incubated for 5 min at 37° C. Complete medium was then added and pipetted up and down to break up cell clumps. Trypsinized cells were collected and centrifuged for 4 min at 320 g. Cells were resuspended, diluted at 1:10 ratio in 10 ml of complete medium and seeded on p100 plates.

HAFi-W3R feeder cells, inactivated by γ-irradiation, support the undifferentiated growth of hiPS cells. For this purpose, HAFi-W3R feeder cells were grown in 150 mm plates at 37° C., 5% CO2, in a humidified atmosphere. Once cells reached 80-90% confluency, they were washed twice with PBS and trypsinized for 5 minutes at 37° C. Finally, 7 ml of DMEM medium was added to stop trypsinization and gently pipetted 10-15 times up and down to break up cells clumps into single cells. Totally, 2×10$^8$ cells were harvested and distributed into four 50 ml conical tubes. To induce replicative arrest, cells were γ-irradiated at 40 Gy. Viable cells were counted using trypan blue-dye exclusion staining and centrifugated for 5 min at 270 g. Inactivated cells were resuspended in cold freezing medium (90% FBS+10% DMSO) adjusting cell density to $2\times10^6$ viable cells/ml. 1 ml aliquots of the cell suspension were distributed into as many cryovials as needed and subsequently stored at $-80°$ C. Next day, vials were transferred to $-150°$ C. container. When required, inactivated frozen cells were thawed, centrifuged for 5 minutes at 240 g. The pellet was resuspended in 10 ml of DMEM medium, seeded on gelatine-coated p100 plates and incubated O.N. at 37° C., 5% CO2, in a humidified atmosphere. Next day, hiPS cells could be passaged onto the HAFi-W3R feeder layer.

hiPS cells, and the subclones derived from them, were cultured on irradiated HAFi-W3R feeder cells. The hiPS cells were cultured in hiPS medium consisting of Knockout (KO) DMEM (Invitrogen, USA) supplemented with 20% Knockout Serum Replacement (KOSR) (Invitrogen, USA), 2 mM Glutamax, 1% non-essential amino acids (NEAA), 0.1 mM β-Mercaptoethanol (Invitrogen, USA) and 8 ng/ml basic fibroblast growth factor (bFGF) (Peprotech, UK) (Lorenzo, I. M., Fleischer, A. and Bachiller, 2013 D. Stem Cell Reviews and Reports, 9 (4): 435-450). The addition of ROCK inhibitor (10 UM Y-27632) to hiPSmedia was necessary in the first 24 hours after passaging, nucleofection and sorting. For nucleofection experiments, hiPS cells were transferred to matrigel-coated dishes (10 μg/cm$^2$) allowing growth in feeder-free conditions After culturing on matrigel for 2 day, cells were used for nucleofection experiments as described in section 1.2.8.3 "Transfection methods".

hiPS cells, and the subclones derived from them, were cultured on irradiated HAFi-W3R feeder cells. The hiPS cells were cultured in hiPS medium consisting of Knockout (KO) DMEM (Invitrogen, USA) supplemented with 20% Knockout Serum Replacement (KOSR) (Invitrogen, USA), 2 mM GlutaMAX, 1% Non-essential amino acids (NEAA), 0.1 mM β-Mercaptoethanol (Invitrogen, USA) and 8 ng/ml basic fibroblast growth factor (bFGF) (Peprotech, UK). (Lorenzo, I. M., Fleischer, A. and Bachiller, 2013 cited ad supra). The addition of ROCK inhibitor (10 μM Y-27632) to the hiPS medium was necessary during 24 hours, after each cell passage, nucleofection and sorting. In order to grow the hiPS cells in the feeder-free conditions necessary for nucleofection, hiPS cells were cultured in plates previously treated with matrigel solution (10 μg/cm$^2$) (BD Biociences, USA) for 1 hour. After culturing for 2 days on matrigel the cells were used for nucleofection experiments as described in section 1.2.8.3 "Transfection methods".

1.2.8.2—hiPS Cell Derivation

Primary cells were obtained from 2 mm$^3$ skin samples. Epidermal keratinocytes and dermal fibroblasts were isolated from the biopsies and cultured following a previously published protocol (Normand, J. and Karasek, M. A. 1995, In Vitro Cell Dev Biol Anim, 31 (6): 447-455). Primary cultures were transduced with three (KLF4, OCT4, SOX2) or four (c-MYC KLF4, OCT4, SOX2) reprogramming factors by two rounds of retroviral infection. A detailed protocol has been already published (Lorenzo, I. M., Fleischer, A. and Bachiller, 2013. Cited ad supra). Reprogrammed cells were mechanically split. Pluripotent colonies were selected by morphology and seeded onto murine embryonic fibroblast feeder cells (Lorenzo, I. M., Fleischer, A. and Bachiller, 2013. Cited ad supra) to produce stable hiPS cell lines. Feeder cells were cultured in DMEM High glucose (Biowest, France). supplemented with 10% Fetal Bovine Serum (FBS) (Biowest, France), 2 mM GlutaMAX and 1% NEAA (Invitrogen, USA) and 50 U/ml penicillin/streptomycin (Thermo Fisher Scientific, USA). The hiPS cell lines were cultured in KO-DMEM (Invitrogen, USA) supplemented with 20% KOSR (Invitrogen, USA), 2 mM GlutaMAX, 1% NEAA, 0.1 mM β-Mercaptoethanol (Invitrogen, USA) and 8 ng/ml basic bFGF (Peprotech, UK). After generating a master bank of frozen cell lines at early passages, lines selected on the basis of colony morphology and replication efficiency were further amplified and cultured over antibiotic-resistant, Wnt expressing, human foreskin fibroblasts (Cai, L., et al. 2007, Cell research, 17 (1): 62-72). Mechanical splitting was used to generate the frozen master bank, whereas enzymatic splitting using recombinant trypsin (TrypLE Select, Invitrogen, USA) was performed thereafter with the addition of 10 μM ROCK inhibitor Y-27632 (Sigma, Spain) to enhance survival of dissociated single hiPS cells (Watanabe, K., et al. 2007, Nature biotechnology, 25 (6): 681; Park, I. H., et al. 2008, Nature, 451 (7175): 141).

1.2.8.3—Transfection Methods 1.2.8.3.1—Lipofection: Hela Cells

Hela cells were lipofected in p6 wells plates with jetPEI, a cationic linear PEI transfection reagent (Polyplus transfection, New York, USA), according to manufacturer's instructions. At the time of transfection, Hela cells were 70% confluent which roughly corresponds to $2$-$4\times10^5$ cells growing in a p6 well. For each lipofection reaction two reaction mixtures were prepared. The first one consisted of 3 μg DNA diluted in 150 mM NaCl to a final volume of 100 μl and the second one, of 6 μl jetPEI reagent in 150 mM NaCl to a final volume of 100 μl. Solution were mixed gently, vortexed for 15 seconds and spun down briefly. 100 μl jetPEI solution were added to 100 μl DNA solution, vortexed, spun down briefly, and then incubated for 30 minutes at room temperature. The 200 μl jetPEI/DNA mix was then drop-wise added to the cells maintained in 2 ml serum-containing complete medium. Cells were homogenously distributed on the plate by gently swirling. After culturing cells for 8 hours at 37° C., growth media was replaced. Puromycin [2 μg/ml], G418 [1.2 mg/ml]) or FIAU ((1-(2-deoxy-2-fluoro-β-d-arabinofuranosyl)-5-iodouracil) [1 μM]) were generally added 72 hours after lipofection. Following 3-4 weeks of selection, individual cell clones were manually picked and expanded for further experimentation.

The docking platform was integrated into the genome in three recombination steps. Step 1 consisted in the incorporation of the first docking vector, pEP24, by TALEN-assisted homologous recombination followed by excision of the selection element by PB transposase. In Step 2, pEP28 was integrated through site-specific attB/attP recombination catalyzed by phiC31 integrase, followed by excision of the new selection element by SB transposase. Finally, in step 3 the pEP50-SV40 vector was incorporated by phiC31/gp3 site-specific recombination between the attR and attL sites. The selection element was then excised by PB transposase (see Results 2.1 "Design of the building strategy").

In step 1, the first transfection included three plasmids: pEP24, CCR5 FW (TALEN-F) and CCR5 REV (TALEN-R). Correct recombination events were selected with puromycin. To excise the selection marker (puroΔtk), 3 μg of the plasmid carrying PB transposase were transfected, and negative selection with FIAU was employed. In step 2, two plasmids were transfected: pEP28 and phiC31 integrase. Correct recombination events were selected by puromycin. To excise the selection element (selection marker: puroΔtk) and remaining vector elements, 3 μg of the plasmid carrying SB transposase were transfected, and negative selection with FIAU was employed. In step 3, the transfection included two plasmids: pEP50, and phiC31 integrase plus gp3 (both encoded in the same plasmid). Correct recombination events were selected with puromycin. To excise the selection element, cells were transfected with the plasmid carrying PB transposase and negative selection with FIAU was administrated. The total amount of added plasmids was 3 µg in each transfection assay.

In order to evaluate the functionality of the Bxb1-specific attB attachment sites present in the docking modules, cells containing the 4 module docking platform were transfected with a loading plasmid, pEP46, carrying a promoterless mCherry fluorescence gene and the plasmid encoding Bxb1 integrase (pCMV_Bx) at a 1:1 ratio (total DNA:3 µg) (Table 13).

TABLE 13

Transfection conditions in HeLa cells. For each transfection, donor plasmids and enzymes are indicated. SE excisions only required transfection of the plasmid encoding the corresponding transposase. Total volume of DNA was 3 µg per transfection.

| Transfection | Plasmids | | µg DNA | Selection |
| --- | --- | --- | --- | --- |
| | Vector | Enzyme | | |
| HR | pEP24 : | TALENs forward and reverse | 1.5:0.75:0.75 | Puromycin |
| phC31-mediated integration | pEP28 : | phiC31 | 1.5:1.5 | Puromycin |
| phC31/gp3-mediated integration | pEP50 : | phiC31 + gp3 | 1.5:1.5 | Puromycin |
| SE Excision by PB | — | PB transposase | 3 | FIAU |
| SE Excision by SB | — | SB transposase | 3 | FIAU |
| Bxb1 loading assay | pEP46 : | Bxb1 | 1.5:1.5 | G418-mCherry |

1.2.8.3.2—Nucleofection: Hips Cells hiPS cells were transfected by nucleofection with the P4 Primary Cell 4D-Nucleofector_Kit (Lonza, Walkersville, MD, USA) according to the manufacturer's instructions. In order to avoid feeder cells contamination, hiPS cells were expanded in p100 plates coated with matrigel solution (10 µg/cm2) prior to nucleofection. The cultures were dissociated with TrypleE (Thermofisher, USA) into single cells. Then, 0.8-1.6×10$^6$ cells were nucleofected in one cuvette, so 6 nucleofections were done per experiment (6×10$^6$ cells in total).

In order to avoid feeder cells contamination, hiPS cells were expanded in p100 plates coated with matrigel solution (10 µg/cm2) prior to nucleofection. The cultures were dissociated with TrypleE (Thermofisher, USA) into single cells. Then, 1×10$^6$ cells were nucleofected in a 100 µl cuvette. Totally, six nucleofections were carried out per experiment (6×10$^6$ cells).

In order to incorporate the first module of the docking platform by TALEN-assisted HR (step 1), hiPS cells were transfected with 4 µg of each plasmid. The first transfection included three plasmids: pEP24, CCR5 FW (TALEN-F) and CCR5 REV (TALEN-R). Correct recombination events were selected with puromycin. To excise the selection marker (puroΔtk), 8 µg of the plasmid encoding PB transposase were transfected, and negative selection with FIAU was applied (Table 14).

In order to evaluate the functionality of the Bxb1-specific attB attachment sites present in the docking module, cells containing the 4-module docking platform were transfected with a loading plasmid, pEP46, carrying a promoterless mCherry fluorescence gene, and the plasmid encoding Bxb1 integrase. Total amount of plasmid transfected was 8 µg (Table 14).

TABLE 14

Transfection conditions in hiPS cells. For each loading reaction, donor plasmids and enzymes are indicated. SE excisions only required the transfection of the plasmid encoding the corresponding transposase. Total volume of DNA was 16 µg to HR transfection and 8 µg for the others two transfection.

| Transfection | Plasmids | | µg | Selection |
| --- | --- | --- | --- | --- |
| | Vector | Enzyme | DNA | |
| HR | pEP24 : | TALENs forward and reverse | 4:4:4 | Puromycin |
| SE Excision by PB | — | PB transposase | 8 | FIAU |
| Bxb1 loading assay | pEP46 : | Bxb1 | 4:4 | G418-mCherry |

After nucleofection cells were quickly reseeded onto multi-antibiotic resistant HAFi-W3R feeders. To enhance cell survival, the Rho kinase inhibitor Y27632 (Tocris Bioscience, Bristol, UK) was used for the first 24 h after nucleofection. Transfected hiPS cells were selected with 800 ng/ml puromycin (Invitrogen) during 2-3 weeks, starting 3 days after nucleofection. Surviving clones were picked manually and expanded for DNA analysis and further experimentation.

2. Results 2.1 Design of the Building Strategy

The aim of this invention is to generate a stable docking platform for secure and easy loading of genetic information into the genome of mammal cells. To build this safe harbor system, a complex strategy combining TALEN-assisted HR and site-specific recombination methods was designed, and constitutes the first result of the project. The strategy provides a serial mechanism by which multiple docking modules, each comprised of four docking sites, can be assembled into the CCR5 locus.

The initial step in the creation of the docking platform was the integration of the first docking module consisting of four docking sites at the CCR5 locus. Each docking site is composed of one cHS4 insulator element, the SV40 promoter and a Bxb1-specific attB attachment site. In addition to the docking module, the donor plasmid, pEP24, also includes a recombination cassette flanked by 5' and 3' CCR5 homology arms. The recombination cassette is composed of a phiC31-specific attB attachment site, a Sleeping Beauty right-ITRs and a puroΔtk selection cassette flanked by piggyBac ITR elements. After a correct homologous recombination event, the puroΔtk gene is removed by piggyBac transposition.

The next step is the incorporation, by site-specific recombination catalyzed by phiC31, of a second docking module identical to the first one. In this case the recombination vector, pEP28, contains the docking module, a phiC31-specific attP site, the right-ITR of PB, and a puroΔtk selection element preceded by the left ITR of SB. Site-specific integration results in two new attachment sites: attL and attR. After integration, left and right-ITRs SB appear flanking a section of the newly incorporated DNA fragment that contains the puroΔtk selection module, the attR and a portion of the recombination vector. This configuration facilitates the SB transposase to remove all the unnecessary elements after the right clones have been selected. The removal of the attR attachment site is critical to avoid interferences during the third recombination step.

The final step in the creation of a docking platform involves integration of a third docking module consisting of another 4 docking sites. The new module is incorporated by site-specific recombination between phiC31-specific attL and attR sites. As explained previously, phiC31 by itself is not able to catalyze the reaction efficiently and has to be aided by the recombination directionality factor gp3. Besides the docking module, the recombination vector, pEP50, contains a phiC31-specific attR site, a right-ITR SB element and a puroΔtk selection element preceded by a left-ITR of PB. Site-specific integration resulted in recombination between the attL and attR sites, thus regenerating the attB and attP sites. After integration, the right-ITR PB is located at the 3'end of the puroΔtk selection cassette in the correct orientation to allow the activity of PB transposase. PB activity leads to the removal of the attP site as well as vector fragments and the puroΔtk selection element.

2.2 Plasmid Construction

To build the platform it was necessary to start by synthesising a series of plasmids carrying the different elements to be assembled in the final structure.

2.2.1 Recombination Plasmids

Three plasmids were built: pEP24, pEP28 and pEP50 (FIG. 5). pEP24 was used in the homologous recombination step. pEP28 and pEP50 are the plasmids used in the second and third recombination steps, respectively. All of them contain one docking module consisting of four docking sites.

The construction of the recombination plasmids has several common cloning steps that simplified their synthesis. The plasmid used as a common backbone was pKOscrambleV920 (see Materials and Methods section). This plasmid is 1968 bp in length and confers ampicillin resistance. In the first step of cloning, specific phiC31 recognition sequences (attB, attP or attR), synthesized by Genewiz (USA), were incorporated into the vector between the AgeI and KpnI restriction sites (FIG. 6).

Figure 6:
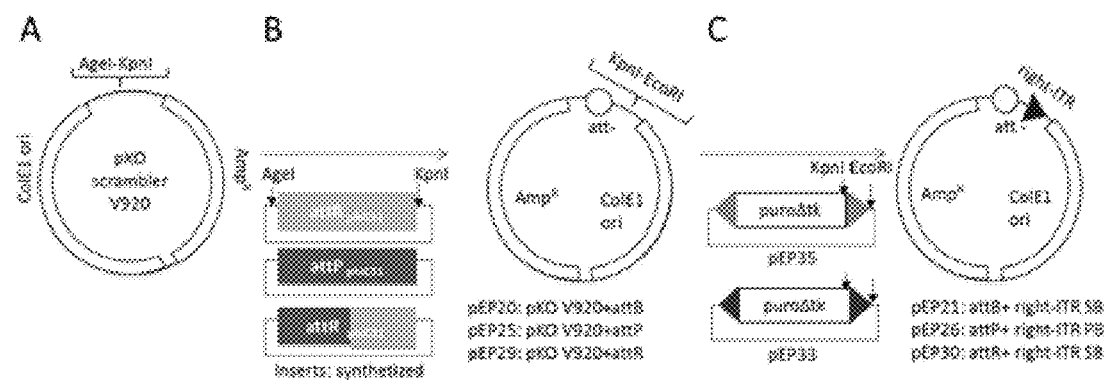
FIG. 6. First and second steps of phiC31 recombination vectors construction. (A) pkOscramblerV920 carries the ColE1 origin of replication and the ampicillin resistance gene. (B) phiC31 attachment sites were synthetized flanked by specific (AgeI and KpnI) restriction sites. Three new plasmids were obtained after cloning each of the attachment phiC31 sites into pKOscramblerV920: pEP20 (attB), pEP25 (attP) and pEP29 (attR). (C) pEP35 harboring the selection marker (puroΔtk) flanked by ITR elements of SB. pEP33 harboring selection marker (puroΔtk) flanked by ITR elements of PB. Only the right-ITR element of each transposon was integrated in the final vectors generating three new plasmids: pEP21 (attB+right-ITR SB), pEP26 (attP+right-ITR PB) and pEP30 (attR+right-ITR SB). Light grey rectangle: phiC31-specific attB sites. Dark grey rectangle.

As a result, three new plasmids were obtained: pEP20 with an attB phiC31 site, pEP25 with an attP phiC31 site and pEP29 with an attR phiC31 site (FIG. 6). Restriction pattern analysis revealed positives clones for each plasmid. Six clones were analysed for pEP20 and pEP25, and five clones for pEP29 (FIG. 7). All colonies obtained from pEP25 and pEP29 were positives showing the expected restriction digestion pattern (FIGS. 7 B and C). pEP25 and pEP29 were digested by BglII and BsaI, respectively, obtaining two restriction bands with slightly different sizes: 1044 and 1135 bp for pEP25; 989 and 1131 bp for pEP29 (FIGS. 7 B and C). Regarding pEP20, digestion by SalI, of the only positive clone, pEP20.3, showed the correct restriction pattern (209 and 1853 bp) (FIG. 7A).

In the next step, the right-ITR element of PB or SB, depending on the plasmid, were incorporated (FIG. 6) into the newly generated plasmids pEP20, pEP25 and pEP29.

For this purpose, two new plasmids, pEP33 and pEP35 had been previously constructed. They comprise the puroΔtk selection element flanked by ITR elements of PB and SB, respectively. To incorporate the ITRs, pEP20, pEP25 and pEP29, were cleaved by KpnI and EcoRI. The right-ITRs were extracted, purified and incorporated into the corresponding pEP33 or pEP35 previously digested with the same enzymes. The right-ITR of SB were cloned into pEP20 and pEP29 and the right-ITR of PB into pEP25 giving rise to three new plasmids named pEP21, pEP26 and pEP30 (FIG. 6).

Eight bacterial colonies were grown from pEP21, six from pEP26 and five from pEP30. pEP21 colonies were digested with SalI, showing the correct restriction pattern of two band of 435 and 1853 bp (FIG. 8A). The pEP26 clones were digested by XmnI and those from pEP30 by SalI. Three pEP26 clones (26.1-26.4-26.6) showed the expected restrictions bands of 509 and 1910 bp (FIG. 8 B). Three pEP30 clones (30.1-30.2-30.3) were also positive, producing bands of 493 and 1853 bp (FIG. 8 C)

After incorporating the specific phiC31 attachment site and right-ITR elements in the vectors, the next step consisted in the insertion of the docking modules. One docking module comprises four docking sites, each one consisting of a cHS4 insulator, the SV40 promoter and one Bxb1-specific attB site. A core docking module was synthetized by Genewiz (USA) (~1.6 kb length) (FIG. 9A) and then used as a template for PCR synthesis of four docking elements with different but compatible restrictions sites for Golden Gate assembling (BamHI-BsmBI (A), BsmBI (A)-BsmBI (B), BsmBI (B)-BsmBI (C) and BsmBI (C)-AscI (see material and method) (FIG. 9A). BsmBI is a Type IIS enzyme used in Golden Gate cloning to assemble multiple modules in a single reaction (Engler, C., Kandzia, R. and Marillonnet, S. 2008, PloS one, 3 (11): e3647). Type IIS restriction enzymes bind to their recognition sites but cut the DNA downstream from that site at a positional, not sequence-specific site. Thus, a single Type IIS restriction enzyme can be used to generate docking units with unique but compatible overhangs. PCR products from the four reactions were cloned into the pGEM-Teasy vector and sequenced (data not shown) to confirm their identities. pGEM-Teasy based plasmids containing the different PCR products were digested with the following enzymes: docking element 1 with BamHI and BsmBI; docking element 2 and 3 with BsmBI and docking element 4 with BsmBI and AscI (FIG. 9 B). The isolated PCR fragments were assembled using their complementary overhangs to create a complete docking module with four docking elements each (FIG. 9 B-C).

A second ligation reaction was then set to clone the full docking module into the BglII/AscI sites of pEP21, pEP26 and pEP30. Three new plasmids were recovered: pEP22, pEP27 and pEP31 (FIG. 9 C). Beside the docking module pEP22 carried a phiC31-specific attB site and a SB right-ITR element, pEP37 a phiC31-specific attP site and a PB right-ITR element, and pEP31 a phiC31-specific attR site and a SB right-ITR element (FIG. 9 C).

Twelve clones from pEP22 were picked and analysed by AgeI restriction. Only clone 22.9 was positive for the expected band of 9047 bp (FIG. 10A). Twenty clones from pEP27 and pEP31 plasmids were analysed. In a first step, plasmids were digested with NheI (data not shown), and then, all possible positives clones digested again with EcoRI. Restriction pattern analysis confirmed the presence of one positive clone for each one of the constructs: 27.18 (FIG. 10 B-left), and 31.17 (FIG. 10 B-right). The next cloning step consisted in the incorporation of the selection marker (SM) flanked by transposon elements. From this point on, the plasmid generated from pEP22 (pEP23) followed a different cloning strategy than the plasmids generated from pEP27 (pEP28) and pEP31 (pEP50). pEP23 carries the SM flanked by two ITR elements, whereas pEP28 and PEP50 contains only one ITR located 5' to the SM. The generation of pEP28 and pEP50 is described in see Results 2.1.

To construct pEP23, the puroΔtk cassette, flanked by ITR elements of PB, was isolated from pEP33 by NheI/AscI digestion and cloned into pEP22 previously linearized with the same enzymes (FIG. 11A). The resulting pEP23, included a phiC31-specific attB site, the right-ITR element of SB, the docking module and puroΔtk flanked by ITR elements of PB. One (23.7) out of 12 clones analyzed showed the expected AgeI restriction pattern of 4653 and 7603 bp (FIG. 11 B).

The last step to generate the homologous recombination vector, pEP24 (FIG. 5), consisted in the cloning of the CCR5 5' and 3' recombination arms. To this intend, the pEP34 plasmid was constructed (FIG. 12). The exon 3 region of the human CCR5 gene was amplified using the 480up/down specific pair of primers (see material and methods, section 1.1.3) using as template DNA from the IMEDEAi003-A hiPS cell line. This newly synthesized PCR product served as a template for a second round of PCR reactions in which the CCR5-5' and 3' recombination arms were amplified (FIG. 12A). Both final PCR products were sequenced to confirm the correctness of DNA sequence (data not shown). Finally, double-digested SbfI/MluI 3' recombination arm and the NotI/BsmBI 5' recombination arm were sequentially cloned into the linearized pKOscramblerV920 (FIG. 12 B).

Restriction analysis with EcoRI demonstrated the correct restriction pattern (3652 and 4832 bp) in all clones, except clone 11 (FIG. 12 C).

To finish the construction of pEP24, the docking cassette from vector pEP23 (attB phiC31 site, right-ITR element of SB, docking module and puroΔtk selection marker flanked by ITR elements of PB) was cloned into the AatII/PacI restriction sites of pEP34. The final plasmid, pEP24, carried the docking cassette flanked by CCR5 5' and 3' recombination arms (FIG. 13 A). Digestion of pEP24 with XhoI revealed two positive clones (24.2 and 24.8) with the correct restriction pattern (3313 and 10897 bp) (FIG. 13 C).

The last step in the generation of the second recombination vector, pEP28, consisted in the cloning of the SM and the left-ITR element of SB from pEP35 into the AscI/NotI sites of pEP27 (FIG. 14A). The final plasmid, pEP28, consisted of a phiC31-specific attP site, the right-ITR element of PB, the docking module and the puroΔtk cassette preceded by the left-ITR element of SB (FIG. 14A). Restriction analysis by SalI confirmed the correct structure of pEP28 in nine out of twelve clones analyzed (FIG. 14 B).

Finally, the construction of the third recombination vector, pEP50, was performed by cloning the SM (puroΔtk) with the left-ITR element of PB into the pEP31 vector previously linearized by AscI/NotI digestion. pEP50 contained one phiC31-specific attR site, the right-ITR element of SB, the docking module and the puroΔtk with the left-ITR element of PB at its 5' side (FIG. 15A). After digestion with KpnI, four correctly assembled clones showed the expected restriction pattern; of 1515, 1693 and 5276 bp (FIG. 15 B).

2.2.2 Generation of Test Plasmids for phiC31 and Bxb1 Recombinase Assay

To validate the functionality of the docking platform assembled at the CCR5 locus, a promoterless loading vector with a fluorescent reporter gene was synthetized. For this purpose, a Bxb1-specific attP attachment site was first generated by annealing of two previously synthesized oligonucleotides (Thermo Fisher Scientific, USA) and inserted via PciI/NheI restriction sites into the pmCherryC1 vector replacing its original CMV promoter (FIG. 16A).

To confirm the correct configuration of the plasmid, pEP46 clones were digested with SacII. All clones analysed showed the expected restriction pattern (FIG. 16 B).

3.3 Assembly of the Docking Platform in the Human HeLa Cell Line

As a proof of concept study, the docking platform was first assembled in a basic cellular model, the human HeLa cell line. Hela cells are of human origin, easy to transfect and have a wide range of applications in biomedical studies. Assembly of the complete docking platform into the human CCR5 locus required sequential loading of the cargos of the three recombination vectors, pEP24, pEP28 and pEP50. The pEP24 targeting vector was integrated by TALENs-assisted HR. pEP28 and pEP50 upload was mediated by phiC31 recombinase. To confirm the reliability of the work in progress, diagnostic components were sequenced after each recombination step.

The first step in the assembly process was initiated with the lipofection of the recombination vector, pEP24, and a pair of CCR5-specific TALENs into Hela cells. Following puromycin selection, 52 clones were isolated and expanded. The 5' and 3' recombination sites were analysed by PCR (FIG. 17A). Thirteen clones showed correct integration patterns of the 5' end of the docking cassette (FIG. 17 B), but only eight of the thirteen showed also correct 3' integration (FIG. 17 C). TALENs-assisted HR showed a frequency of 34 (Table 15). Finally, clone 24 was chosen for further experimentation based on its growth and sensibility to FIAU.

Following the integration of the first docking module into the human CCR5 locus, the puroΔtk selection cassette was excised in the HeLa CI.24 clone by transfection with PB transposase followed by FIAU selection. 48 HeLa clones survived the negative selection process. Successful excision of puroΔtk was confirmed in 6 out of 34 clones analyzed by PCR screening (Table 15, FIG. 18). The efficiency of the excision reaction was 17% (Table 15).

The phiC31-specific attB site is crucial for the next step of platform assembly. In order to integrate a new docking module into the platform, HeLa CI.24.22 cells, were transfected with a phiC31 integrase expressing plasmid and the second recombination vector, pEP28, that harbors a phiC31-specific attP site. Successful attB/attP recombination catalyzed by the phiC31 integrase was confirmed in 4 out of the 24 puromycin resistant clones analyzed. The test was conducted by screening the 3' (FIG. 19 B) and 5' (FIG. 19 C) recombination sites by PCR (FIG. 19A). Moreover, PCR analysis using primers specific for the 5' of the docking platform in step 1, confirmed the disappearance of the PCR amplicon in the four candidate clones as result of the site-specific recombination event in step 2 (FIG. 19 D). Integration efficiency was 16% (Table 15).

After puromycin selection, the puroΔtk cassette, remaining vector elements and selection cassette in the HeLa CI.24.22.21 and HeLa CI.24.22.29 lines were removed by transfection with SB transposase and exposition to FIAU selection. Successful SE excision was demonstrated in three subclones of Hela 24.22.21 (24.22.21.3, 24.22.21.7 and 24.22.21.18) and one subclone of HeLa 24.22.29 (24.22.29.7) cells (FIG. 20 B, shows a negative control PCR) by lack of PCR amplicon (173 bp) (FIG. 20A shows the schematic representation of the lack of the amplicon, wherein the elements within the discontinue line rectangle are missing) because the primers cannot bind to the template. To confirm the PCR result cells clones were shown to be sensible to puromycin, but resistant to FIAU treatment (FIG. 21). Finally, HeLa CI.24.22.21.3 was selected for completion of the docking platform assembly since it displayed the best growth properties.

After site-specific recombination between the attB and attP sites occurred in step 2, two novel phiC31-specific recombination sites, attL and attR, were generated in HeLa CI.24.22.21.3 following transfection of the SB transposase. Subsequently, the integrity of the attL phiC31 site was confirmed by sequencing attR phiC31 site was excised by SB transposase, therefore there was not necessary to confirm the integrity.

Figure 5:
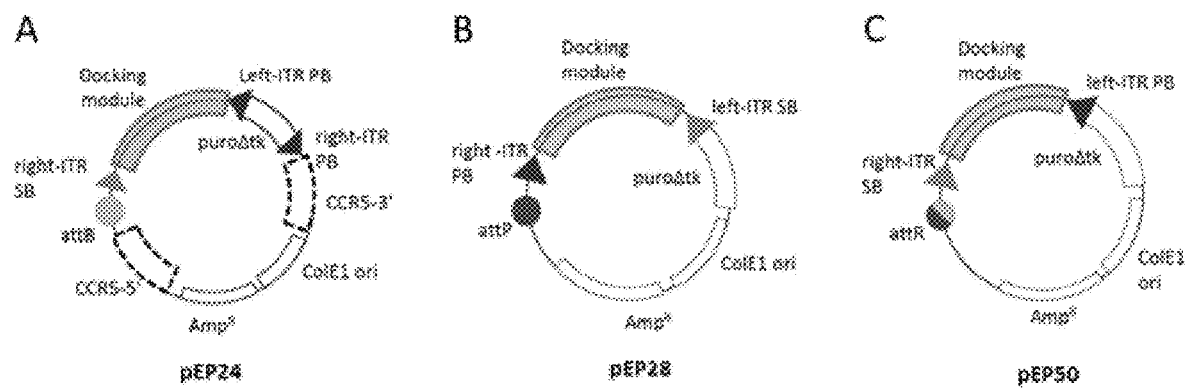
FIG. 5. Schematic representation of the recombination vectors. (A) pEP24 contains two CCR5 homology arms, attB phiC31 site, right-ITR element of SB, a docking module and selection marker (puroΔtk) flanked by ITR element of PB. (B) pEP28 consists of an attP phiC31 site, right-ITR element of PB, a docking module and selection marker (puroΔtk) with a left-ITR element of SB at 5'. (C) pEP50 consists of an attR phiC31 site, right-ITR element of SB, a docking module and a selection marker (puroΔtk) with an ITR element of PB at 5'. Bold discontinue square: CCR5 recombination arms. Light grey circles: phiC31-specific attB sites. Dark grey circles: phiC31-specific attP sites. Half dark/light grey circles: phiC31-specific attR sites. Light grey triangles: SB-specific ITR elements. Dark grey triangles: PB-specific ITR elements. Curved rectangle: docking module.

Efficient recombination between attL and attR sites, upon which the last recombination step is based, requires the participation of gp3 along with the phiC31 integrase. HeLa CI.24.22.21.3 cells were transfected with an expression vector containing the fusion protein gp3-phiC31 (pCS_KRI) and the third recombination vector, pEP50 (FIG. 5). Following attL/attR recombination, attP and attB sites were regenerated and the third docking module was incorporated into the genome, resulting in a docking platform of 12 docking sites. Following puromycin selection, 15 out of 29 clones analyzed showed successful restauration of the attB phiC31 site (FIG. 22 B). The recombination event had an efficiency of 48% (Table 15). In addition to puromycin resistance HeLa clones were sensible to FIAU selection, further demonstrating the integrity of the puroΔtk cassette.

The 4 FIAU sensitive clones that showed faster respond to FIAU selection were chosen for confirmation by PCR. Successful attR/attL recombination catalyzed by the phiC31 integrase and gp3 was confirmed by screening the 5' (FIGS. 22 B and C) and 3' (FIG. 22 D). To verify the correct integration in 5', two different PCRs were performed. The first PCR was designed to detect the regenerated attB site (FIG. 22A). Since, pEP50 contains a right-ITR element of SB, which was a unique component of the platform at that stage a second specific PCR test aimed at detecting it was possible (FIG. 22A). 3 out of 4 clones re-confirmed both attB regeneration and the presence of the right-ITR element of SB (FIG. 22 B). HeLa CI.24.22.21.3.65 cells did not show any PCR amplicons in any PCR analyses, but in contrast a regenerated attB site and the right-ITR element of SB were detected in HeLa CI.24.22.21.3.98 and CI.24.22.21.3.145 clones (FIG. 22 C). HeLa CI.24.22.21.3.129, showed attB regeneration but absence of the right-SB-ITR element, and was re-analyzed using a bigger amount of template DNA. The second test confirmed that is was also positive for the ITR (FIG. 22 C). Representation of 5' positive clones were also positive to 3' PCR. HeLa CI.24.22.21.3.65 shows weak band due to less DNA amount (FIG. 22 D).

Although deletions were detected at the 3' end of the attB site, the integrity of the core sequence, crucial for site-specific recombination, was confirmed.

To complete the construction of the platform, the SE was excised from the HeLa CI.24.22.21.3.98 and CI.24.22.21.3.145 clones by transfection with PB integrase. Successful SE excision was demonstrated by lack of PCR amplicon (343 bp) (FIG. 22A) because the primers cannot bind to the template. A total of 52 clones were resistant. PCR analysis demonstrated the absence of SE in seven and two FIAU-resistant clones, respectively (Table 15, FIG. 23). To confirm PCR result, clones with excised SE were cultured in the presence of puromycin or FIAU, showing sensibility to puromycin and resistance to FIAU.

Overall, the data presented so far demonstrate the feasibility of the procedure designed to build the platform, as well as the efficiency of the different recombination reactions in uploading and excising genetic material from the human genome. Table 15 provides a summary of the results.

TABLE 15

Recombination efficiencies at each of the three steps of the synthesis.

| | | Number of colonies | | | Positives | | Frequency |
|---|---|---|---|---|---|---|---|
| | | Picked colonies | Viable | Analyzed | (5') PCR | (3') PCR | of positive clones (%) |
| Step 1 | HR | 131 | 52 | 23 | 13 | 8 | 34 |
| | Excision of SE by PB | 48 | 48 | 34 | NA | 6 | 17 |
| Step 2 | phiC31 integrase | 33 | 24 | 24 | 4 | 4 | 16 |
| | Excision of SE by SB | 60 | 60 | 21 | NA | 3 | 14 |
| Step 3 | phiC31 integrase + gp3 | 29 | 29 | 29 | 15 | 13* | 48** |
| | Excision SE by PB | 52 | 52 | 52 | NA | 9 | 17 |

Step 1. HR: incorporation of the first docking module by TALEN-assisted HR. Excision of the SE by PB transposase.
Step 2. phiC31 integrase: incorporation of the second docking module by site-specific phiC31 recombination. Excision of the SE by SB transposase.
Step 3. phiC31 integrase + gp3: incorporation of the third docking module by site-specific phiC31/gp3 recombination. Excision of the SE by PB transposase.
Positives (5') PCR represents the number of clones analyses which showed correct integration at the 5'end.
Positive (3') PCR represents the number of clones positive to 5' that were also positive for the 3' end.
Frequency of positive clones represents the percentage of clones positive for both 5' and 3' end with respect to total number of clones analysed.
NA: no applicable.
(*) only 13 out of the 15 5' positive clones had enough DNA to be tested for the 3' end.
(**) This frequency represents the percentage of both positive of the 5' and 3' end (13) out of the 27 analyzed.

3.4 Loading Test of the Docking Platform in Hela Cells

After integrating the first docking element in the CCR5 locus of Hela cells, its functionality was tested before continuing with the construction of the platform. For this purpose, HeLa CI.24.22 cells harboring only one docking module with four docking sites were chosen. In this cell line, it is possible to determine by PCR the exact number and position of the docking units occupied by the transferred cargo (FIG. 4). HeLa CI.24.22 cells were transfected with the reporter vector pEP46 carrying a promoterless mCherry (FIG. 16) and the vector expressing Bxb1 integrase. Following G418 selection, stable cells clones were isolated and expanded. Since the mCherry construct lacks a promoter, only successful recombined clones could correctly express the reporter gene. Indeed, transfection of mCherry without Bxb1 recombinase resulted in the complete absence of mCherry expressing cells (data not shown). Finally, clones with correct growth and morphology were analysed by FACS and fluorescence microscopy based on mCherry expression (FIG. 24 and FIG. 25)

Of the eight clones analysed, seven showed multiple peaks, which could be interpreted either as evidence of polyclonality, or as variability in the level of expression in a monoclonal cell line. Only clone five showed unimodal emission spectrum (Table 16).

TABLE 16

Summary of the number of loaded Bxb1 docking sites in HeLa 24.22 clones.

| | HeLa Cl.24.22 subclones | | | | | | | |
|---|---|---|---|---|---|---|---|---|
| Subclone number | 1 | 2 | 3 | 4 | 5 | 6 | 7 | 8 |
| Occupied docking sites | 2 | 3 | 3 | 4 | 1 | 2 | 2 | 2 |

HeLa Cl. 24.22 harbored four Bxb1-specific attB sites.

Following DNA extraction, the number and location of the loaded recombination site was determined for all the clones by PCR analyses using site-specific Bxb1-BQ primers (FIG. 26).

Clone 5, showed a unimodal emission spectrum by FACS and had integrated the mCherry construct only in position 2 of the docking module. The remaining seven clones showed multimodal emissions and a multiple loading status with 1-4 docking sites occupied. It is not clear at this point whether the variability of expression could be ascribed to a possible polyclonality of each one of the seven variable clones, to different expression levels in each one of the docking sites, or simply to variabilities between cells within individual clones. Nevertheless, these results indicate that all four docking sites could be efficiently loaded and were functional, although the functionality of each position should be verified in future experiments.

3.5 Generation of hiPS Cell Lines

Mammal cell lines that support reliable and predictable expression of large numbers of transgenes are an enabling technology for a wide range of scientific, industrial and therapeutic applications. To explore additional uses of the docking platform in therapeutic applications, hiPS cell lines were generated (Fleischer, A., et al. 2018, Stem cell research, 29:1-5).

One of the fibroblast-derived MKOS line, IMEDEAAi003-A, was described and characterized regarding their genetic stability, stemness and pluripotency. First, the karyotype was analyzed by standard G-loading and found to be normal.

The completion of the reprograming process and the silencing of the reprogramming factors were further evaluated by comparing the expression of endogenous and exogenous OCT4, SOX2, KLF4 and c-MYC by RT-PCR (FIG. 27). By using specific primers to detect the reprogramming transcripts, IMEDEAi003-A cells demonstrated complete silencing of exogenous transgenes. In addition, quantitative RT-PCR was also performed on NANOG, Rex and CRIPTO. In contrast to primary fibroblast, IMEDEAi003-A showed strong expression of the stemness markers.

Stemness was assessed by immunostaining for NANOG, OCT4, SSEA3, SSEA4, TRA-1-60 and TRA-1-81. IMEDEAi003-A expressed high levels of stem cells markers (FIG. 28). To test whether IMEDEAi003-A retained the capacity to differentiate into the three embryonic layers (ectoderm, mesoderm and endoderm) a method based on embryoid bodie production was used. After a minimum of ten days of suspension culture, embryoid bodies were disrupted mechanically and plated on gelatin. Plated embryoid bodies derivatives were analyzed by immunostaining. Ectodermal lineages were confirmed by the expression of NESTIN and TUJ1, while GATA4 and α-ACTININ illustrated the presence of mesoderm and SOX17 and AFP of endoderm (FIG. 28).

3.6 Assembly of the First Docking Module into the CCR5 Locus of hiPS Cells

The first docking step consisted in the integration of the docking recombination, pEP24, in the CCR5 locus by TALENs-stimulated homologous recombination.

For this purpose, as in the case of the HeLa cell line, the hiPS cell line IMEDEAi003-A was transfected with the pEP24 recombination vector and CCR5-specific TALENs. Following puromycin selection 152 clones were isolated and expanded. 4 clones displayed correct integration of the recombination cassette at the 5' terminal region (FIG. 29A). 4 clones displayed integration of the recombination cassette at 5' (FIG. 29 B), whereas 3 out of the 4 clones showed successful integration at the 3' end (FIG. 29 C). The hiPS Clone CI.87, showing correct growth and sensibility to FIAU (data not shown), was chosen for further experimentation.

Next, the SE (3101 bp) was excised by transfection with PB transposase followed by selection with FIAU. Successful excision of the selection elements was confirmed in 24 out of 52 clones analysed by PCR with the attB-Bxb1-1/CCR5-3rev2 pair of primers (FIG. 30). All clones showed excision except hiPS CI.87.35 (FIG. 30). hiPS CI87.38 was used for functional testing of the docking platform since it displayed the best growth properties. Table 17 contains a summary of the results obtained in the loading of the first docking module in human iPS cells.

TABLE 17

Recombination efficiencies during hiPS loading. HR. Recombination vector pEP24 integration by TALEN-assisted HR. Excision of SM by phiC31-specifi PiggyBac(PB) transposase.

| | Number of colonies | | | Positive | | Frequency of |
|---|---|---|---|---|---|---|
| | Picked colonies | Viable | Analyzed | (5') PCR | (3') PCR | positive clones (%) |
| HR | 157 | 152 | 47 | 4 | 3 | 5 |
| Excision of SE by PB | 72 | 69 | 52 | NA | 24 | 46 |

Picked colonies: individual clones picked after puromycin selection.
Viable: number of clones surviving the recovery and expansion process.
Analyzed: number of clones analyzed.
Positives (5') PCR: number of clones analyses which showed correct integration at the 5'end.
Positive (3') PCR: number of clones positive to 5' that were also positive for the 3' end.
Frequency of positive clones: percentage of clones positive for both 5' and 3' end with respect to total number of clones analysed.
NA: No applicable.

3.7 Loading Test of the Docking Platform in Hips Cells

Once the first docking module was integrated into the CCR5 locus in hiPS cells it was necessary to test its functionality. Similar to the loading experiment already described for Hela cells, hiPS CL.87.38 cells were transfected with the reporter plasmid pEP46 (attP Bxb1+ mCherry+NeoR) and a vector encoding the Bxb1 integrase. Following G418 selection, stable cells clones were isolated and expanded. Since the mCherry construct was promoterless, only successfully recombined clones could express the reporter gene. Indeed, transfection of mCherry without Bxb1 recombinase resulted in the complete absence of mCherry expressing cells. Finally, clones with correct growth and morphology were analysed by FACS and fluorescence microscopy regarding their mCherry expression (FIG. 31).

Following DNA extraction, the number and location of the loaded Bxb1 sites was determined in 24 clones by PCR analyses, according to the screening strategy already described for Hela cells (FIG. 4, Table 10 and Table 18).

TABLE 18

Summary of the number of loaded Bxb1 docking sites in the hiPS 87.38 clone. hiPS CI.87.38 contained four attB Bxb1 attachment sites. It was transfected with pEP46 that harbored attP Bxb1 attachment site.

| hiPS CI.87.38 clones' number | Occupied docking site | Total occupied docking site |
|---|---|---|
| 1(*) | 1; 3 | 2 |
| 2(*) | 3 | 1 |
| 3 | 3; 4 | 2 |
| 4 | 3; 4 | 2 |
| 5 | 1 | 1 |
| 6(*) | 2; 3; 4 | 3 |
| 7 | 3; 4 | 2 |
| 8(*) | 4 | 1 |
| 9 | 2; 3 | 2 |
| 10 | 4 | 1 |
| 11 | 1; 3 | 2 |
| 12(*) | 1; 2; 3 | 3 |
| 13(*) | 2 | 1 |
| 14(*) | 2 | 1 |
| 15 | 2; 3; 4 | 3 |
| 16 | 2; 3 | 2 |
| 17(*) | 2 | 1 |
| 18 | 2 | 1 |
| 19(*) | 2 | 1 |
| 20 | 2 | 1 |
| 21 | 2; 4 | 2 |
| 22(*) | 1; 2; 3 | 3 |
| 23(*) | 1; 2; 3 | 3 |
| 24 | 2 | 1 |

(*)unimodal mCherry expression by FACS.

FACS analysis revealed unimodal expression in 11 out of 24 clones, however, PCR analysis showed that some of the clones with multimodal expression (5, 10, 18, 20 and 24) had only one docking site occupied. This combination of factors suggests that the variance of expression observed could be due to intrinsic variability within the lines and not to differential activity between the four docking units (FIG. 32).

Overall, the results obtained with hiPS cells confirm those previously observed in HeLa cells, and demonstrate that the same strategy for building the docking platform can be successfully used in very different cells lines. In addition, they underline the flexibility and versatility of the docking system and highlight the potential to load various transgenes at the same time.

4. Discussion

This invention shows the construction of a docking site for the secure and easy loading of genetic information into the genome of mammal cells. For this purpose, complex array of molecular and cellular techniques were integrated into a single protocol. The strategy provides a serial mechanism by which multiple docking modules, each comprised of four docking sites, can be assembled into the human CCR5 locus. First, TALEN-mediated homologous recombination promotes the precise integration of the first docking module. Then, a combination of the site-specific recombination systems phiC31 and transposon systems, piggyBac and Sleeping Beauty, catalyzes the addition of a theoretically indefinite number of docking modules and the excision of unwanted DNA elements that might interfere with the loading and expression of future genes of interest.

The functionality of this multiple site-specific Bxb1 integration platform was confirmed by loading the fluorescence promoterless mCherry reporter gene.

As a proof of concept, the construction of the docking platform was first carried out in the immortalized, easy-to-transfect, HeLa cell line. Once the functionality of the system was confirmed, the platform was assembled in a therapeutically relevant cell-type. With this aim, hiPS cells were generated from healthy donor's fibroblast by reprogramming with the four canonical Yamanaka factors. Bona fide hiPS cell lines were identified and their stemness, pluripotency and correct karyotype were verified.

In the first step of platform assembly, a docking module was integrated into the CCR5 locus by TALEN-assisted HR. In the last decade, ZFNs, TALENs and CRISPR/Cas9 have been intensively used to introduce targeted and specific modifications into the genome of living cells and organisms. However, several reports have shown that ZFNs have lower success rates due to lower cutting efficiency than the other two. TALEN and CRISPR/Cas9 endonucleases have recurrently achieved equally good rates of gene editing. TALENs have demonstrated to be useful to correct disease phenotypes. In fact, TALEN have shown up to 90% cutting efficiency with negligible off-target activity in HEK 293 cells.

Although the docking platform could have been assembled in several loci like AAVS1, Rosa26 or H11, several observations suggested to select CCR5 as the integration site for the multi-copy docking platform since a natural null mutation of the gene is present in human individuals with no apparent consequences to their health.

In the experiments conducted during this invention, correct TALEN-mediated homologous recombination events occurred at a frequency of 34% in HeLa and 5% in hiPS cells. These efficacies are obviously much higher than those obtained by classical, unassisted HR, especially in hiPS cells. The differences between cell lines in targeting efficiency could be attributed to chromatin structure and/or DNA methylation that may negatively affect accessibility of TALENs to DNA. The chromatin structure is dynamic and differs between genomic loci.

The next step in the protocol was to integrate the second docking module by site-specific recombination catalyzed by phiC31. Serine integrases, such as phiC31, promote recombination between two different DNA recognition sites, attP and attB, resulting in new recombined attL and attR sites.

The second step of the protocol includes the integration into the genome of a phiC31-specific attB attachment site that could later be used as a target for recombination with the phiC31-specific attP site located in the second docking vector, pEP28. This particular arrangement of the attB/attP pair has been included to prevent random integrations of the docking vector into the pseudo-attP sites present in the human genome.

To increase phiC31 activity and specificity distinct mutations may be introduced into the N-terminal and C-terminal domains. Variants with mutations T21, V6A, S7Δ, V9E, D10V, D40A, D44A, V49I, and D52A are all located in the N-terminal part of the enzyme. This domain has been shown to have limited ability to recognize pseudo attP sites, but an increased affinity for the wild type-attP sequence. Hence, overall increasing the specificity for the attP site. Performing site-specific recombination with this mutant integrase could potentially increase the recombination rates observed in the experiments previously described.

In step three of the synthesis of the docking platform, the recombination vector, pEP50, was successfully integrated in Hela cells by phiC31 and gp3 at a frequency of 48%, which is in concordance with the published results (see above).

At the three steps of the construction process, correct integration events were assessed by PCR analysis of the 5' and 3' ends of the integration site. In the case of HR-mediated integration only 8 out of the 13 clones that were positive for the 5' end showed also correct integration of the 3' extreme, whereas in the cases of phiC31 integrase-mediated recombination, all clones with correct 5' integration were also accurately integrated at the 3' end.

The general design includes the use of two different site-specific recombinase systems: phiC31 for the assembly of the docking platform and Bbx1 to load the desired genetic elements onto the platform after its completion. The synthesis of the platform is complex, but once it is finished, the cells equipped with it would be used as a base for multiple pharmaceutical and biomedical applications. To increase its applicability, it was very important to ease the loading process. Since the Bxb1 integrase system is the most efficient recombinase described in literature, and attL/attR recombination was only required during the phase of synthesis, phiC31 was chosen for the assembly of the docking platform and Bxb1 for the loading phase.

To test the functionality of the novel docking platform, a proof-of-principle study was performed by loading the fluorescence reporter gene mCherry in cells harboring only one docking module with four attB loading sites. The analysis of a wide variety of HeLa and hiPS cells clones revealed that each cloning position was functional. Moreover, multiple loading events could be detected thereby generating cells with two, three or four copies of mCherry.

The docking functional platform of this invention can also allow for simultaneous integration of various transgenes. These integrations are performed at the same chromosomal location, which could be useful to study metabolic routes or gene interactions that require close transgene positions. In addition, multiple docking units can be incorporated into the genome after the initial single homologous recombination event, thus, reducing the possibility of off-target effects when compared to several independent integrations at different locations.

The docking module described here consists of four docking sites. Each docking site represents a transcriptional unit containing a cHS4 insulator, the SV40 promoter and a Bxb1 attachment site. Only one cHS4 insulator element was placed 5' upstream of SV40 promoter to guarantee the function of each transcriptional unit while minimizing the size of the docking vector.

The docking platform was designed and constructed with the small but strong SV40 promoter, which is frequently used to achieve high levels of expression in a variety of mammal cell and tissue types. The SV40 promoter was cloned 5' upstream of the Bxb1 attachment site, so that only successful recombination events could give rise to cell clones with correct transgene expression. As the loading vector lacks a promoter element, randomly integrated transgenes will not be expressed in the cells.

In order to obtain recombed SM-free cell clones, the strategy developed in this invention involves a double selection process after each step of homologous or site-specific recombination. First, recombined cells clones carrying the recombination cassette including the double selection marker, puroΔtk, were selected by puromycin. Second, following PiggyBac (PB) or Sleeping Beauty (SB) transposase excision, FIAU selection allowed the isolation of recombed cells clones that had successfully excised the SM. The inclusion of this step in the building strategy had the additional objective of removing from the safe harbor location any DNA vector fragment that might later have undesired effects on transgene expression. Besides the elimination of exogenous vector DNA, it was crucial to excise the attachment site attR generated by attP/attB recombination in order to continue with step two of the assembly strategy.

Following TALEN-assisted HR at the CCR5 locus, the cells carried the selection cassette puroΔtk flanked by both ITR elements of PB and the left-ITR element of SB. Once cells were transfected with PB transposase, the selection element was removed leaving only the left-ITR of SB, confirming that transposases' specificities did not overlap and was possible to use them in the same design. After performing the first step of the platform assembly (attP/attB recombination) the ITR configuration completely changed. The selection cassette was now flanked by ITRs (left and right) of SB and the left ITR element of PB. Finally, following step three (attL/attR recombination) the order of ITRs was identical to the situation described after homologous recombination. Even though each transposon has "cut and paste" activity, each species has its own molecular structure and mechanism and ITR sequences are specifically required for the interaction with their cognate transposases. For these reasons, PB transposase is unable to interact with ITRs of SB and vice versa. This concept has been validated in this invention.

Cell type dependant transposition efficiencies have been observed during the creation of the docking platform. The excision efficiency by PB was 17% in Hela cells whereas SB-mediated excision was observed in 14% of HeLa clones analyzed. The efficiency obtained in this invention for PB-mediated excision in hiPS cells, 46%, was similar to those obtained in published studies, which are significantly higher than in Hela cells.

Most gene expression platforms described in the literature are based on a single site-specific recombinase element, previously introduced in the genome by HR. The present invention has the advantage of its simplicity. Unlike these platforms, the method of the invention can provide as many attachment sites as needed, offering integration of several transgenes at the same locus. In addition, the docking platform presented in this invention is the first example of a loading system that, thanks to the alternated use of PB and SB, eliminates, together with all remaining vectors elements, the SM (puroΔtk), thus making possible to use the same selection cassette in consecutive loadings.

This invention discloses a novel strategy to achieve accurate multi-site-specific integration of exogenous genetic information into mammal cells. The assembly of the docking platform combined TALEN-assisted HR with phiC31-mediated site-specific recombination followed by the combined use of PB and SB transposon to excise the selection cassette. The alternating use of PB and SB ITR element has permitted the use of the same selection cassette, puroΔtk, in each recombination step and the excision of any vector elements that could later on interference with transgene expression. Furthermore, the transposon-dependant excision of the selectable element used during the assembly of the docking platform could also be incorporated into a loading vector, thus allowing the successive integration of genes of interest without selection marker limitations.

Unlike other loading systems, this novel multiple docking platform has been designed to incorporate four docking units at each recombination step. More importantly, the building cycle can be repeated as many times as needed, even after genes of interest have already been loaded. This feature gives the platform the plasticity to adapt to new needs arising from the behavior of the already loaded elements.

Thanks to the results obtained with Hela cells, the validity of the design, and the functionality of the platform were confirmed. Preliminary data obtained from hiPS cells has also shown that the strategy can be applied to different cell lines, suggesting that phiC31 and Bxb1 integrases, together with the PB and SB transposon systems, and the set of recombination and loading vectors already synthesized, might mediate chromosomal integration in a wide range of host environments, including plants, insects and other mammal cells.

The invention claimed is:

1. An in vitro method for inserting at least one recombinant site in a target gene from a cell genome, said method comprising:
   (a) integrating a nucleotide sequence A into the target gene by homologous recombination, wherein said nucleotide sequence A comprises a recombination cassette, flanked at the 5' and 3' ends by target gene homology arms, comprising
      (i) a phiC31 serine-integrase attB or attP attachment site,
      (ii) a right-inverted terminal repeat (ITR) element specific for a first transposase,
      (iii) a genetic construction comprising, at least one transcriptional unit comprising a first recombinant site, and
      (iv) a selection marker flanked by ITR elements specific for a second transposase, wherein the second transposase is different than the first transposase,
      wherein the transcriptional unit comprises, in this order,
      (a) an insulator,
      (b) a promoter, and
      (c) the first recombinant site, wherein the first recombinant site is at least one serine-integrase attachment site specific for a serine-integrase different from the phiC31 serine-integrase, and
   (b) removing the selection marker by using the second transposase, thus obtaining a cell genome A comprising elements (i), (ii) and (iii) of the nucleotide sequence A.

2. The method according to claim 1, further comprising the following steps:
   (c) integrating a nucleotide sequence B into the cell genome A by the action of a phiC31 serine-integrase, wherein said nucleotide sequence B comprises
      (i) a phiC31 serine-integrase attachment site complementary to the phiC31 serine-integrase attachment site of the nucleotide sequence A,
      (ii) a right-ITR element specific for the second transposase,
      (iii) a genetic construction comprising, at least one transcriptional unit comprising a second recombinant site, and
      (iv) a selection marker comprising in its 5' end a left-ITR element specific for the first transposase of the nucleotide sequence A, and
   (d) removing the selection marker and the newly created hybrid attR or attL attachment site by the use of the first transposase of the nucleotide sequence A, thus obtaining a cell genome B comprising (i) a hybrid attL or attR attachment site and elements (ii) and (iii) of the nucleotide sequence B, and element (iii) of the nucleotide sequence A.

3. The method according to claim 2, further comprising the following steps:
   (e) integrating a nucleotide sequence C into the cell genome B, by the action of a phiC31 serine-integrase recognizing the hybrid attL or attR attachment site of the cell genome B and a phiC31 recombination directionality factor (RDF), wherein nucleotide sequence C comprises (i) a serine-integrase hybrid attR or attL attachment site complementary to the hybrid attL or attR attachment site of cell genome B,
(ii) a right-ITR element specific for the first transposase of the nucleotide sequence A,
(iii) a genetic construction comprising at least one transcriptional unit comprising a third recombinant site, and
(iv) a selection marker comprising in its 5'end a left-ITR element specific for the second transposase of the nucleotide sequence B, and
(f) removing the selection marker and the newly created attP or attB attachment site by the use of the second transposase of nucleotide sequence B, thus obtaining a cell genome C comprising (i) the serine-integrase attB or attP attachment site and elements (ii) and (iii) of the nucleotide sequence C, element (iii) of the nucleotide sequence B, and element (iii) of the nucleotide sequence A.

4. The method according to claim 3, further comprising:
(g) carrying out step (c) and (d) if one additional recombinant site is going to be inserted into the same target gene of the cell genome, or
(g') carrying out steps (c), (d), (e) and (f) if two additional recombinant sites are going to be inserted into the target gene of the cell genome,
wherein steps (g) or (g') are repeated as many times as recombinant sites are to be inserted into the target gene from the cell genome.

5. The method according to claim 4, wherein the nucleotide sequences A, B and C are integrating circular plasmids or vectors.

6. The method according to claim 1, wherein the cell genome is from a human cell, a Chinese hamster ovary (CHO) cell, or a 3T3 cell.

7. The method according to claim 1, wherein the homologous recombination of step (a) is a transcription activator-like effector (TALEN)-assisted homologous recombination.

8. An isolated cell, comprising at least one recombinant site within its genome, obtained by a method according to claim 1.

9. An in vitro method for loading a gene of interest into a cell genome comprising:

(a) inserting a recombinant site into the cell genome by a method according to claim 1, and
(b) introducing the gene of interest by means of a serine-integrase specific for the serine-integrase attachment site comprised within the transcriptional unit inserted into the cell genome according to step (a).

10. The method according to claim 9, wherein the gene of interest is comprised within a genetic construction comprising, in this order
(a) a serine-integrase attachment site specific for a serine-integrase which recognizes the serine-integrase attachment site comprised within the transcriptional unit,
(b) the gene of interest, and
(c) a selection marker flanked by two ITR elements specific for a non-replicative DNA transposase.

11. An isolated cell obtained by a method according to claim 9.

12. A nucleotide sequence comprising a recombination cassette, flanked at the 5' and 3' ends by target gene homology arms, comprising:
(i) a phiC31 serine-integrase attB or attP attachment site,
(ii) a right-ITR element specific for a first transposase,
(iii) a genetic construction comprising, at least one, Bxb1 integrase attB or attP attachment site, and
(iv) a selection marker flanked by ITR elements specific for a second transposase, wherein the second transposase is different from the first transposase.

13. A circular vector or plasmid comprising a nucleotide sequence according to claim 12.

14. An isolated cell comprising a nucleotide sequence according to claim 12.

15. A nucleotide sequence comprising a recombination cassette comprising:
(i) a phiC31 serine-integrase attP or attB attachment site complementary to a second phiC31 serine-integrase attachment site,
(ii) a right-ITR element specific for a first transposase,
(iii) a genetic construction comprising, at least one, Bxb1 integrase attB or attP attachment site, and
(iv) a selection marker comprising at 5' a left-ITR element specific for a second transposase, wherein the second transposase is different from the first transposase.

* * * * *

```
                              SEQUENCE LISTING

<160> NUMBER OF SEQ ID NOS: 61

<210> SEQ ID NO 1
<211> LENGTH: 27
<212> TYPE: DNA
<213> ORGANISM: Artificial Sequence
<220> FEATURE:
<223> OTHER INFORMATION: Primer GG1-F

<400> SEQUENCE: 1
gcgcgtctag aggatcccga gctcacg                                           27

<210> SEQ ID NO 2
<211> LENGTH: 30
<212> TYPE: DNA
<213> ORGANISM: Artificial Sequence
<220> FEATURE:
<223> OTHER INFORMATION: Primer GG2-F

<400> SEQUENCE: 2
gcgtctagac gtctcacatg cgagctcacg                                        30

<210> SEQ ID NO 3
<211> LENGTH: 30
<212> TYPE: DNA
<213> ORGANISM: Artificial Sequence
<220> FEATURE:
<223> OTHER INFORMATION: Primer GG3-F

<400> SEQUENCE: 3
gcatctagac gtctcaggac cgagctcacg                                        30

<210> SEQ ID NO 4
<211> LENGTH: 30
<212> TYPE: DNA
<213> ORGANISM: Artificial Sequence
<220> FEATURE:
<223> OTHER INFORMATION: Primer GG4-F

<400> SEQUENCE: 4
gcttctagac gtctcaccag cgagctcacg                                        30

<210> SEQ ID NO 5
<211> LENGTH: 29
<212> TYPE: DNA
<213> ORGANISM: Artificial Sequence
<220> FEATURE:
<223> OTHER INFORMATION: Primer GG1-R

<400> SEQUENCE: 5
cgacgcgtca tgtgagacgg cccggatga                                         29

<210> SEQ ID NO 6
<211> LENGTH: 30
<212> TYPE: DNA
<213> ORGANISM: Artificial Sequence
<220> FEATURE:
<223> OTHER INFORMATION: Primer GG2-R

<400> SEQUENCE: 6
```

```
tttacgcgtg tcctgagacg gcccggatga                                    30

<210> SEQ ID NO 7
<211> LENGTH: 30
<212> TYPE: DNA
<213> ORGANISM: Artificial Sequence
<220> FEATURE:
<223> OTHER INFORMATION: Primer GG3-R

<400> SEQUENCE: 7
tttacgcgtc tggtgagacg gcccggatga                                    30

<210> SEQ ID NO 8
<211> LENGTH: 36
<212> TYPE: DNA
<213> ORGANISM: Artificial Sequence
<220> FEATURE:
<223> OTHER INFORMATION: Primer GG4-R

<400> SEQUENCE: 8
ttacgcgtgg cgcgcctatt gctagcgccc ggatga                             36

<210> SEQ ID NO 9
<211> LENGTH: 22
<212> TYPE: DNA
<213> ORGANISM: Artificial Sequence
<220> FEATURE:
<223> OTHER INFORMATION: Primer 480up

<400> SEQUENCE: 9
gactgagttg cagccgggca tg                                            22

<210> SEQ ID NO 10
<211> LENGTH: 24
<212> TYPE: DNA
<213> ORGANISM: Artificial Sequence
<220> FEATURE:
<223> OTHER INFORMATION: Primer 480down

<400> SEQUENCE: 10
accaaccagg atctccctgc tcag                                          24

<210> SEQ ID NO 11
<211> LENGTH: 38
<212> TYPE: DNA
<213> ORGANISM: Artificial Sequence
<220> FEATURE:
<223> OTHER INFORMATION: Primer CCR5-5homUP

<400> SEQUENCE: 11
tatgcggccg cacgcgttcc aggctgcagt gagccatg                           38

<210> SEQ ID NO 12
<211> LENGTH: 43
<212> TYPE: DNA
<213> ORGANISM: Artificial Sequence
<220> FEATURE:
<223> OTHER INFORMATION: Primer CCR5-5homDN

<400> SEQUENCE: 12
cctgctagcg agacgtcatt aaaacacagc caccacccaa gtg                     43

<210> SEQ ID NO 13
<211> LENGTH: 37
<212> TYPE: DNA
```

```
<213> ORGANISM: Artificial Sequence
<220> FEATURE:
<223> OTHER INFORMATION: Primer CCR5-3homUP

<400> SEQUENCE: 13
tatcctgcag gtgcttgtca tggtcatctg ctactcg                              37

<210> SEQ ID NO 14
<211> LENGTH: 29
<212> TYPE: DNA
<213> ORGANISM: Artificial Sequence
<220> FEATURE:
<223> OTHER INFORMATION: Primer CCR5-3homDN

<400> SEQUENCE: 14
tttacgcgtg cttccccagc tctcccagg                                       29

<210> SEQ ID NO 15
<211> LENGTH: 61
<212> TYPE: DNA
<213> ORGANISM: Artificial Sequence
<220> FEATURE:
<223> OTHER INFORMATION: Primer attP-Bxb1-up

<400> SEQUENCE: 15
catgtgtcgt ggtttgtctg gtcaaccacc gcggtctcag tggtgtacgg tacaaaccca     60
g                                                                     61

<210> SEQ ID NO 16
<211> LENGTH: 61
<212> TYPE: DNA
<213> ORGANISM: Artificial Sequence
<220> FEATURE:
<223> OTHER INFORMATION: Primer attP-Bxb1-down

<400> SEQUENCE: 16
ctagctgggt tgtaccgta caccactgag accgcggtgg ttgaccagac aaaccacgac      60
a                                                                     61

<210> SEQ ID NO 17
<211> LENGTH: 21
<212> TYPE: DNA
<213> ORGANISM: Artificial Sequence
<220> FEATURE:
<223> OTHER INFORMATION: Primer CCR5-5for2

<400> SEQUENCE: 17
caggcttccc gcattcaaaa t                                               21

<210> SEQ ID NO 18
<211> LENGTH: 20
<212> TYPE: DNA
<213> ORGANISM: Artificial Sequence
<220> FEATURE:
<223> OTHER INFORMATION: Primer attBphiC31

<400> SEQUENCE: 18
gatgggtgag gtggagtacg                                                 20

<210> SEQ ID NO 19
<211> LENGTH: 21
<212> TYPE: DNA
<213> ORGANISM: Artificial Sequence
<220> FEATURE:
<223> OTHER INFORMATION: Primer CCR5-3rev2
```

```
<400> SEQUENCE: 19
tgtctccttc tacagccaag c                                            21

<210> SEQ ID NO 20
<211> LENGTH: 20
<212> TYPE: DNA
<213> ORGANISM: Artificial Sequence
<220> FEATURE:
<223> OTHER INFORMATION: Primer PURO/tk

<400> SEQUENCE: 20
ggtaatgaca agcgcccaga                                              20

<210> SEQ ID NO 21
<211> LENGTH: 21
<212> TYPE: DNA
<213> ORGANISM: Artificial Sequence
<220> FEATURE:
<223> OTHER INFORMATION: Primer attB-Bxb1-1

<400> SEQUENCE: 21
gcgctagcga attcgtatgt t                                            21

<210> SEQ ID NO 22
<211> LENGTH: 20
<212> TYPE: DNA
<213> ORGANISM: Artificial Sequence
<220> FEATURE:
<223> OTHER INFORMATION: Primer attLphiC31

<400> SEQUENCE: 22
caaccccttg tgtcatgtcg                                              20

<210> SEQ ID NO 23
<211> LENGTH: 20
<212> TYPE: DNA
<213> ORGANISM: Artificial Sequence
<220> FEATURE:
<223> OTHER INFORMATION: Primer attRphiC31

<400> SEQUENCE: 23
ttttcccagg tcagaagcgg                                              20

<210> SEQ ID NO 24
<211> LENGTH: 21
<212> TYPE: DNA
<213> ORGANISM: Artificial Sequence
<220> FEATURE:
<223> OTHER INFORMATION: Primer attxphiC31

<400> SEQUENCE: 24
agtgtgatca cttgggtggt g                                            21

<210> SEQ ID NO 25
<211> LENGTH: 21
<212> TYPE: DNA
<213> ORGANISM: Artificial Sequence
<220> FEATURE:
<223> OTHER INFORMATION: Primer 3'_SB

<400> SEQUENCE: 25
catcacattc ccagtgggtc a                                            21

<210> SEQ ID NO 26
```

```
<211> LENGTH: 22
<212> TYPE: DNA
<213> ORGANISM: Artificial Sequence
<220> FEATURE:
<223> OTHER INFORMATION: Primer cHS4_R

<400> SEQUENCE: 26
gtaattacat ccctgggggc tt                                            22

<210> SEQ ID NO 27
<211> LENGTH: 21
<212> TYPE: DNA
<213> ORGANISM: Artificial Sequence
<220> FEATURE:
<223> OTHER INFORMATION: Primer PB_R

<400> SEQUENCE: 27
tgacgcatgt gttttatcgg t                                             21

<210> SEQ ID NO 28
<211> LENGTH: 23
<212> TYPE: DNA
<213> ORGANISM: Artificial Sequence
<220> FEATURE:
<223> OTHER INFORMATION: Primer SB_R

<400> SEQUENCE: 28
tccctgtctt aggtcagtta gga                                           23

<210> SEQ ID NO 29
<211> LENGTH: 26
<212> TYPE: DNA
<213> ORGANISM: Artificial Sequence
<220> FEATURE:
<223> OTHER INFORMATION: Primer CCR5_Cat_980_UP

<400> SEQUENCE: 29
aagatggatt atcaagtgtc aagtcc                                        26

<210> SEQ ID NO 30
<211> LENGTH: 20
<212> TYPE: DNA
<213> ORGANISM: Artificial Sequence
<220> FEATURE:
<223> OTHER INFORMATION: Primer CCR5_Sang_490_20UP

<400> SEQUENCE: 30
ttaaaagcca ggacggtcac                                               20

<210> SEQ ID NO 31
<211> LENGTH: 20
<212> TYPE: DNA
<213> ORGANISM: Artificial Sequence
<220> FEATURE:
<223> OTHER INFORMATION: Primer cHS4.BQ-F

<400> SEQUENCE: 31
tcatccaact ccaggacgga                                               20

<210> SEQ ID NO 32
<211> LENGTH: 20
<212> TYPE: DNA
<213> ORGANISM: Artificial Sequence
<220> FEATURE:
<223> OTHER INFORMATION: Primer Bxb1.BQ-F

<400> SEQUENCE: 32
```

```
ggacaggtat ccggtaagcg                                              20

<210> SEQ ID NO 33
<211> LENGTH: 17
<212> TYPE: DNA
<213> ORGANISM: Artificial Sequence
<220> FEATURE:
<223> OTHER INFORMATION: Primer Bxb1.BQ1-R

<400> SEQUENCE: 33
cccgtgagct cgcatgt                                                 17

<210> SEQ ID NO 34
<211> LENGTH: 19
<212> TYPE: DNA
<213> ORGANISM: Artificial Sequence
<220> FEATURE:
<223> OTHER INFORMATION: Primer Bxb1.BQ2-R

<400> SEQUENCE: 34
gtgagctcgg tcctgagac                                               19

<210> SEQ ID NO 35
<211> LENGTH: 19
<212> TYPE: DNA
<213> ORGANISM: Artificial Sequence
<220> FEATURE:
<223> OTHER INFORMATION: Primer Bxb1.BQ3-R

<400> SEQUENCE: 35
gtgagctcgc tggtgagac                                               19

<210> SEQ ID NO 36
<211> LENGTH: 21
<212> TYPE: DNA
<213> ORGANISM: Artificial Sequence
<220> FEATURE:
<223> OTHER INFORMATION: Primer Bxb1.BQ4-R

<400> SEQUENCE: 36
agctgcaggt ttaaacagtc g                                            21

<210> SEQ ID NO 37
<211> LENGTH: 21
<212> TYPE: DNA
<213> ORGANISM: Artificial Sequence
<220> FEATURE:
<223> OTHER INFORMATION: Primer NANOG Forward

<400> SEQUENCE: 37
acaactggcc gaagaatagc a                                            21

<210> SEQ ID NO 38
<211> LENGTH: 19
<212> TYPE: DNA
<213> ORGANISM: Artificial Sequence
<220> FEATURE:
<223> OTHER INFORMATION: Primer NANOG Reverse

<400> SEQUENCE: 38
ggttcccagt cgggttcac                                               19

<210> SEQ ID NO 39
<211> LENGTH: 20
<212> TYPE: DNA
```

```
<213> ORGANISM: Artificial Sequence
<220> FEATURE:
<223> OTHER INFORMATION: Primer CRIPTO Forward

<400> SEQUENCE: 39
cggaactgtg agcacgatgt                                                    20

<210> SEQ ID NO 40
<211> LENGTH: 18
<212> TYPE: DNA
<213> ORGANISM: Artificial Sequence
<220> FEATURE:
<223> OTHER INFORMATION: Primer CRIPTO Reverse

<400> SEQUENCE: 40
gggcagccag gtgtcatg                                                      18

<210> SEQ ID NO 41
<211> LENGTH: 20
<212> TYPE: DNA
<213> ORGANISM: Artificial Sequence
<220> FEATURE:
<223> OTHER INFORMATION: Primer REX1 Forward

<400> SEQUENCE: 41
cctgcaggcg gaaatagaac                                                    20

<210> SEQ ID NO 42
<211> LENGTH: 23
<212> TYPE: DNA
<213> ORGANISM: Artificial Sequence
<220> FEATURE:
<223> OTHER INFORMATION: Primer REX1 Reverse

<400> SEQUENCE: 42
gcacacatag ccatcacata agg                                                23

<210> SEQ ID NO 43
<211> LENGTH: 20
<212> TYPE: DNA
<213> ORGANISM: Artificial Sequence
<220> FEATURE:
<223> OTHER INFORMATION: Primer GAPDH Forward

<400> SEQUENCE: 43
gcaccgtcaa ggctgagaac                                                    20

<210> SEQ ID NO 44
<211> LENGTH: 19
<212> TYPE: DNA
<213> ORGANISM: Artificial Sequence
<220> FEATURE:
<223> OTHER INFORMATION: Primer GAPDH Reverse

<400> SEQUENCE: 44
agggatctcg ctcctggaa                                                     19

<210> SEQ ID NO 45
<211> LENGTH: 22
<212> TYPE: DNA
<213> ORGANISM: Artificial Sequence
<220> FEATURE:
<223> OTHER INFORMATION: Primer Trans-OCT4 Forward

<400> SEQUENCE: 45
tggactacaa ggacgacgat ga                                                 22
```

-continued

<210> SEQ ID NO 46
<211> LENGTH: 17
<212> TYPE: DNA
<213> ORGANISM: Artificial Sequence
<220> FEATURE:
<223> OTHER INFORMATION: Trans-OCT4 Reverse

<400> SEQUENCE: 46
caggtgtccc gccatga                                                  17

<210> SEQ ID NO 47
<211> LENGTH: 23
<212> TYPE: DNA
<213> ORGANISM: Artificial Sequence
<220> FEATURE:
<223> OTHER INFORMATION: Primer Trans-SOX2 Forward

<400> SEQUENCE: 47
gctcgaggtt aacgaattca tgt                                           23

<210> SEQ ID NO 48
<211> LENGTH: 14
<212> TYPE: DNA
<213> ORGANISM: Artificial Sequence
<220> FEATURE:
<223> OTHER INFORMATION: Primer Trans-SOX2 Reverse

<400> SEQUENCE: 48
gcccggcggc ttca                                                     14

<210> SEQ ID NO 49
<211> LENGTH: 22
<212> TYPE: DNA
<213> ORGANISM: Artificial Sequence
<220> FEATURE:
<223> OTHER INFORMATION: Primer Trans-KLF4 Forward

<400> SEQUENCE: 49
tggactacaa ggacgacgat ga                                            22

<210> SEQ ID NO 50
<211> LENGTH: 18
<212> TYPE: DNA
<213> ORGANISM: Artificial Sequence
<220> FEATURE:
<223> OTHER INFORMATION: Primer Trans-KLF4 Reverse

<400> SEQUENCE: 50
cgtcgctgac agccatga                                                 18

<210> SEQ ID NO 51
<211> LENGTH: 22
<212> TYPE: DNA
<213> ORGANISM: Artificial Sequence
<220> FEATURE:
<223> OTHER INFORMATION: Primer Trans-c-MYC Forward

<400> SEQUENCE: 51
tggactacaa ggacgacgat ga                                            22

<210> SEQ ID NO 52
<211> LENGTH: 23
<212> TYPE: DNA
<213> ORGANISM: Artificial Sequence
<220> FEATURE:

```
<223> OTHER INFORMATION: Primer Trans-c-MYC Reverse

<400> SEQUENCE: 52
gttcctgttg gtgaagctaa cgt                                              23

<210> SEQ ID NO 53
<211> LENGTH: 24
<212> TYPE: DNA
<213> ORGANISM: Artificial Sequence
<220> FEATURE:
<223> OTHER INFORMATION: Primer Endo-OCT4 Forward

<400> SEQUENCE: 53
gggtttttgg gattaagttc ttca                                             24

<210> SEQ ID NO 54
<211> LENGTH: 18
<212> TYPE: DNA
<213> ORGANISM: Artificial Sequence
<220> FEATURE:
<223> OTHER INFORMATION: Primer Endo-OCT4 Reverse

<400> SEQUENCE: 54
gcccccaccc tttgtgtt                                                    18

<210> SEQ ID NO 55
<211> LENGTH: 20
<212> TYPE: DNA
<213> ORGANISM: Artificial Sequence
<220> FEATURE:
<223> OTHER INFORMATION: Primer Endo-SOX2 Forward

<400> SEQUENCE: 55
caaaaatggc catgcaggtt                                                  20

<210> SEQ ID NO 56
<211> LENGTH: 24
<212> TYPE: DNA
<213> ORGANISM: Artificial Sequence
<220> FEATURE:
<223> OTHER INFORMATION: Primer Endo-SOX2 Reverse

<400> SEQUENCE: 56
agttgggatc gaacaaaagc tatt                                             24

<210> SEQ ID NO 57
<211> LENGTH: 22
<212> TYPE: DNA
<213> ORGANISM: Artificial Sequence
<220> FEATURE:
<223> OTHER INFORMATION: Primer Endo-KLF4 Forward

<400> SEQUENCE: 57
agcctaaatg atggtgcttg gt                                               22

<210> SEQ ID NO 58
<211> LENGTH: 23
<212> TYPE: DNA
<213> ORGANISM: Artificial Sequence
<220> FEATURE:
<223> OTHER INFORMATION: Primer Endo-KLF4 Reverse

<400> SEQUENCE: 58
ttgaaaactt tggcttcctt gtt                                              23
```

```
<210> SEQ ID NO 59
<211> LENGTH: 15
<212> TYPE: DNA
<213> ORGANISM: Artificial Sequence
<220> FEATURE:
<223> OTHER INFORMATION: Primer Endo-c-MYC Forward

<400> SEQUENCE: 59
cgggcgggca ctttg                                                    15

<210> SEQ ID NO 60
<211> LENGTH: 19
<212> TYPE: DNA
<213> ORGANISM: Artificial Sequence
<220> FEATURE:
<223> OTHER INFORMATION: Primer Endo-c-MYC Reverse

<400> SEQUENCE: 60
ggagagtcgc gtccttgct                                                19

<210> SEQ ID NO 61
<211> LENGTH: 11
<212> TYPE: DNA
<213> ORGANISM: Artificial Sequence
<220> FEATURE:
<223> OTHER INFORMATION: Recognition sequence of type IIS endonuclease
      BsmBI
<220> FEATURE:
<221> NAME/KEY: misc_feature
<222> LOCATION: (7)..(11)
<223> OTHER INFORMATION: n is a, c, g, or t

<400> SEQUENCE: 61
cgtctcnnnn n                                                        11
```